(12) United States Patent
Dezar et al.

(10) Patent No.: US 11,873,501 B2
(45) Date of Patent: Jan. 16, 2024

(54) SOYBEAN TRANSGENIC EVENT IND-00410-5

(71) Applicant: Bioceres LLC, Wilmington, DE (US)

(72) Inventors: Carlos Dezar, Rosario (AR); Patricia Miranda, Rosario (AR); Geronimo Watson, Rosario (AR); Mariana Chiozza, Ames, IA (US); Martin Vazquez, Rosario (AR)

(73) Assignee: BIOCERES LLC, Wilmington, DE (US)

( * ) Notice: Subject to any disclaimer, the term of this patent is extended or adjusted under 35 U.S.C. 154(b) by 253 days.

(21) Appl. No.: 17/424,760

(22) PCT Filed: Mar. 28, 2019

(86) PCT No.: PCT/US2019/024548
§ 371 (c)(1),
(2) Date: Jul. 21, 2021

(87) PCT Pub. No.: WO2020/197558
PCT Pub. Date: Oct. 1, 2020

(65) Prior Publication Data
US 2022/0090114 A1  Mar. 24, 2022

(51) Int. Cl.
*C12N 15/82* (2006.01)
*C12Q 1/6853* (2018.01)

(52) U.S. Cl.
CPC ..... *C12N 15/8273* (2013.01); *C12N 15/8205* (2013.01); *C12N 15/8277* (2013.01); *C12Q 1/6853* (2013.01)

(58) Field of Classification Search
None
See application file for complete search history.

(56) References Cited

U.S. PATENT DOCUMENTS

| | | | |
|---|---|---|---|
| 2002/0144305 A1 | 10/2002 | Dellaporta et al. | |
| 2007/0271630 A1* | 11/2007 | Boukharov | C07K 14/4354 800/301 |
| 2008/0085515 A1* | 4/2008 | Remacle | C12Q 1/689 435/6.15 |
| 2009/0119022 A1* | 5/2009 | Timberlake | G16B 30/10 702/20 |
| 2010/0005547 A1 | 1/2010 | Gelvin et al. | |
| 2011/0214199 A1 | 9/2011 | Coffin | |
| 2012/0144528 A1 | 6/2012 | Unkefer et al. | |
| 2013/0263327 A1 | 10/2013 | Chan et al. | |
| 2014/0017684 A1 | 1/2014 | Channabasavaradhya | |

FOREIGN PATENT DOCUMENTS

| | | |
|---|---|---|
| AR | 090110 A1 | 10/2014 |
| AR | 081216 B2 | 5/2015 |

OTHER PUBLICATIONS

Verdeca Petition (17-223-01p) for Determination of Non-regulated Status of HB4 Soybean. OECD Unique Identifier: IND-00410-5. Plant Pesk Risk Assessment. APHIS. (Year: 2018).*
Genbank Locus EL431765. Mickelmore et al. "Texas blueweed ESTs from the Compositae Genome Project". (Year: 2007).*
Duque et al., "Abiotic Stress Responses in Plants: Unraveling the Complexity of Genes and Networks to Survive," Abiotic Stress—Plant Responses and Applications in Agriculture, 2013, pp. 49-101 (55 pages).
Sayed, "Chlorophyll fluorescence as a tool in cereal crop research," Photosynthetica, 2003, pp. 321-330, vol. 41, No. 3 (10 pages).
International Preliminary Report on Patentability (PCT/IB/326 & PCT/IB/373) issued in PCT Application No. PCT/US2019/024548 dated Oct. 7, 2021 (11 pages).
International Search Report (PCT/ISA/210) issued in PCT Application No. PCT/US2019/024548 dated Sep. 17, 2019 (six (6) pages).
Written Opinion (PCT/ISA/237) issued in PCT Application No. PCT/US2019/024548 dated Sep. 17, 2019 (nine (9) pages).
Fazio et al., "Petition for determination of non-regulated status for the new plant variety HB4 soybean (IND-00410-5) intended for environmental release and food and feed use." Nov. 14, 2017 (see Federal Register vol. 82, No. 219 Wednesday, Nov. 15, 2017 for publication date) [Retrieved on May 28, 2019] Retrieved from website URL:https://www.aphis.usda.gov/brs//aphisdocs/17_22301p.pdf pp. 2-380 (379 pages).

* cited by examiner

*Primary Examiner* — Mykola V. Kovalenko
*Assistant Examiner* — David R Byrnes
(74) *Attorney, Agent, or Firm* — Crowell & Moring LLP

(57) ABSTRACT

The invention relates to the fields of plant production, plant breeding and agriculture. More specifically, it relates to soybean transgenic event IND-ØØ41Ø-5, which expresses the gene HaHB4 that confers drought tolerance without affecting other agricultural capabilities. The application also discloses related nucleotide sequences, plants, parts of plants, seeds, cells, agricultural products, and detection and production methods.

3 Claims, 14 Drawing Sheets
Specification includes a Sequence Listing.

a) Binary vector with the T-DNA.

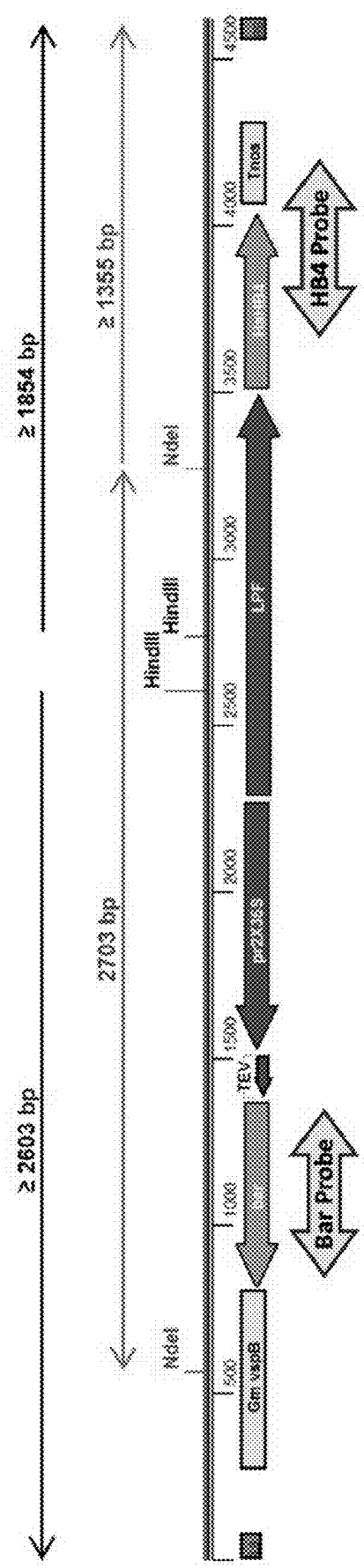
FIGURE 1 (continuation)
b) Detailed portion of pIND2-HB4 T-DNA.

```
                                                                                                                                        INSERT ←|→ SOYBEAN
pIND2-HB4 6600    1   HWI-1KL178:35:C2853ACXX:1:2104:2930:4902/1      GTCAATTTGTTTACACCACAATATATCCTG ATATCTT
pIND2-HB4 6600    2   HWI-1KL178:35:C2853ACXX:1:1211:2771:15845/1     GTCAATTTGTTTACACCACAATATATCCTG ATATCTTTAGTTA
pIND2-HB4 6600    3   HWI-1KL178:35:C2853ACXX:1:2301:2144:45948/1     GTCAATTTGTTTACACCACAATATATCCTG ATATCTTTAGTTAGTTTGGAA
pIND2-HB4 6600    4   HWI-1KL178:35:C2853ACXX:1:2316:1296:42801/1     GTCAATTTGTTTACACCACAATATATCCTG ATATCTTTAGTTAGTTTGGAAAG
pIND2-HB4 6600    5   HWI-1KL178:35:C2853ACXX:1:2115:13502:95101/1    GTCAATTTGTTTACACCACAATATATCCTG ATATCTTTAGTTAGTTTGGAAAGA
pIND2-HB4 6600    6   HWI-1KL178:35:C2853ACXX:1:1113:19014:22369/1    GTCAATTTGTTTACACCACAATATATCCTG ATATCTTTAGTTAGTTTGGAAAGAA
pIND2-HB4 6600    7   HWI-1KL178:35:C2853ACXX:1:2316:19065:48607/1    GTCAATTTGTTTACACCACAATATATCCTG ATATCTTTAGTTAGTTTGGAAAGAATAATTTA
pIND2-HB4 6600    8   HWI-1KL178:35:C2853ACXX:1:2113:14864:18959/1    GTCAATTTGTTTACACCACAATATATCCTG ATATCTTTAGTTAGTTTGGAAAGAATAATTTAGT
pIND2-HB4 6600    9   HWI-1KL178:35:C2853ACXX:1:2108:2906:82396/1     GTCAATTTGTTTACACCACAATATATCCTG ATATCTTTAGTTAGTTTGGAAAGAATAATTTAGTTT
pIND2-HB4 6600   10   HWI-1KL178:35:C2853ACXX:1:1216:16892:95129/1    GTCAATTTGTTTACACCACAATATATCCTG ATATCTTTAGTTAGTTTGGAAAGAATAATTTAGTTTATTT
pIND2-HB4 6600   11   HWI-1KL178:35:C2853ACXX:1:2210:13921:4787/1     GTCAATTTGTTTACACCACAATATATCCTG ATATCTTTAGTTAGTTTGGAAAGAATAATTTAGTTTATTTTCAAGAA
pIND2-HB4 6600   12   HWI-1KL178:35:C2853ACXX:1:1208:16844:51440/1    GTCAATTTGTTTACACCACAATATATCCTG ATATCTTTAGTTAGTTTGGAAAGAATAATTTAGTTTATTTTCAAGAAT
pIND2-HB4 6600   13   HWI-1KL178:35:C2853ACXX:1:2208:19636:50409/1    GTCAATTTGTTTACACCACAATATATCCTG ATATCTTTAGTTAGTTTGGAAAGAATAATTTAGTTTATTTTCAAGAATT
pIND2-HB4 6600   14   HWI-1KL178:35:C2853ACXX:1:2301:11054:65235/1    GTCAATTTGTTTACACCACAATATATCCTG ATATCTTTAGTTAGTTTGGAAAGAATAATTTAGTTTATTTTCAAGAATTT
pIND2-HB4 6600   15   HWI-1KL178:35:C2853ACXX:1:2114:14995:48048/1    GTCAATTTGTTTACACCACAATATATCCTG ATATCTTTAGTTAGTTTGGAAAGAATAATTTAGTTTATTTTCAAGAATTTATT
                  LB
```

JS-9R-32743683

```
pIND2-HB4 -11191   1   HWI-1KL178:35:C2853ACXX:1:2304:14055:23211/1    CGTTTCCCGCCCTTCAGTTAAACTATCAGT ACCCT
pIND2-HB4 -11191   2   HWI-1KL178:35:C2853ACXX:1:1309:18092:53655/1    CGTTTCCCGCCCTTCAGTTAAACTATCAGT ACCCT
pIND2-HB4 -11191   3   HWI-1KL178:35:C2853ACXX:1:1110:18178:97622/1    CGTTTCCCGCCCTTCAGTTAAACTATCAGT ACCCTC
pIND2-HB4 -11191   4   HWI-1KL178:35:C2853ACXX:1:2208:16112:27560/1    CGTTTCCCGCCCTTCAGTTAAACTATCAGT ACCCTCAATCATCT
pIND2-HB4 -11191   5   HWI-1KL178:35:C2853ACXX:1:1306:17316:42797/1    CGTTTCCCGCCCTTCAGTTAAACTATCAGT ACCCTCAATCATCTCACTTCATTATCT
pIND2-HB4 -11191   6   HWI-1KL178:35:C2853ACXX:1:1207:24439:74885/1    CGTTTCCCGCCCTTCAGTTAAACTATCAGT ACCCTCAATCATCTCACTTCATTATCTCCT
pIND2-HB4 -11191   7   HWI-1KL178:35:C2853ACXX:1:2304:2245:47357/1     CGTTTCCCGCCCTTCAGTTAAACTATCAGT ACCCTCAATCATCTCACTTCACTTCATTATCTCCTATATTT
pIND2-HB4 -11191   8   HWI-1KL178:35:C2853ACXX:1:1105:16023:21830/1    CGTTTCCCGCCCTTCAGTTAAACTATCAGT ACCCTCAATCATCTCACTTCACTTCATTATCTCCTATATTTTTATTAA
pIND2-HB4 -11191   9   HWI-1KL178:35:C2853ACXX:1:2102:17291:93541/1    CGTTTCCCGCCCTTCAGTTAAACTATCAGT ACCCTCAATCATCTCACTTCACTTCATTATCTCCTATATTTTTATTAAC
pIND2-HB4 -11191  10   HWI-1KL178:35:C2853ACXX:1:1215:20878:69009/1    CGTTTCCCGCCCTTCAGTTAAACTATCAGT ACCCTCAATCATCTCACTTCACTTCATTATCTCCATATTTTTATTAACTTCTCTTTTAT
pIND2-HB4 -11191  11   HWI-1KL178:35:C2853ACXX:1:2107:2551:89129/1     CGTTTCCCGCCCTTCAGTTAAACTATCAGT ACCCTCAATCATCTCACTTCACTTCATTATCTCCATATTTTTATTAACTTCTCTTTTATACTA
pIND2-HB4 -11191  12   HWI-1KL178:35:C2853ACXX:1:2114:15932:44919/1    CGTTTCCCGCCCTTCAGTTAAACTATCAGT ACCCTCAATCATCTCACTTCACTTCATTATCTCCATATTTTTATTAACTTCTCTTTATACTATTTTAAAA
pIND2-HB4 -11191  13   HWI-1KL178:35:C2853ACXX:1:1212:18583:52229/1    CGTTTCCCGCCCTTCAGTTAAACTATCAGT ACCCTCAATCATCTCACTTCACTTCATTATCTCCATATTTTTATTAACTTCTCTTTATACTATTTTAAAAA
                  RB
```

SOYBEAN TRANSGENIC EVENT IND-00410-5

FIELD OF THE INVENTION

The invention relates to the fields of plant production, plant breeding and agriculture. More specifically, it relates to soybean transgenic event IND-00410-5, nucleotide sequences, plants, parts of plants, seeds, cells, agricultural products, and detection and production methods related to soybean transgenic event IND-00410-5.

BACKGROUND OF THE INVENTION

To improve crop yields and their characteristics has become essential to satisfy food demand. Due to biotechnological developments and their combination with agriculture, new crops have been developed with capacity to adapt to diverse environmental and/or ecological conditions.

During plant growth, plants are exposed to a variety of abiotic stresses: drought, salinity and low temperatures, high temperatures, excessive radiation, low nutrient availability, soil compaction preventing root development, etc. (Duque et al., 2013; Sayed 2003). All of them are capable of affecting at some point plant growth, as well as plant yield. It is reasonable to suppose that some of these environmental factors may occur during crop life cycles at the field. In this instance, complex answer mechanisms are triggered that will reflect in measurements performed as they are the result of the integration of such stress effects.

One of the commonly used techniques to mitigate the negative effects the environment may have on crops is based on transgenic events, i.e., insertion of the genes of interest in the genome of a target crop. However, production and selection of a commercially suitable transgenic event requires extensive investigation, analysis and characterization of a large number of individual transformation events. In this way, it is possible to select an event that has the desired trait and thus develops the phenotypic and agricultural characteristics necessary to be suitable for commercial purposes, without negatively affecting other crop characteristics. Thus, it is possible to select an event that has the desired trait and therefore develops the phenotypic and agricultural characteristics necessary to be commercially suitable, without affecting other crop characteristics.

This process requires generating transgenic events that will be molecularly and phenotypically characterized to identify and select the event expressing the heterologous gene of interest in line with the obtention of the desired phenotype.

Event selection implies stages of laboratory development as well as tests at the field and/or at greenhouse, under controlled conditions. It is necessary to analyze the response to events along the years, in multiple locations and under a variety of environmental conditions to be able to select the event that satisfies the required phenotypic and genetic characteristics as well as commercial ones.

The present invention provides such type of event commercially suitable, which makes room for new advantageous traits in soybean.

There is a large variety of genes that may be used in the elaboration of events with commercial interest. Among them, there are in the market soybean plants expressing genes tolerant to herbicides or genes encoding insecticidal proteins, etc. A gene the expression of which is of interest is the one encoding transcription factor HAHB4.

HAHB4 (*Helianthus annuus* homeobox-4) is a sunflower transcription factor that belongs to the HD-Zip family. The HaHB4 gene expression is regulated at transcriptional level by external environmental factors such as water availability and soil salinity, as well as phytohormones related therewith, abscisic acid and ethylene.

Patent AR81216B2 discloses gene HaHB4 inducible by water deficit and abscisic acid that encodes a sunflower transcription factor type HD-Zip. Said patent discloses gene isolation and characterization, and its introduction in the model plant *Arabidopsis thaliana*. However, neither transgenic plants carrying the event with commercial interest of the present invention are made available to the public, nor their advantageous properties related to abiotic stresses jointly developed in agriculture conditions.

Likewise, there is no mention in patent AR81216B2 concerning the particular selection of an event expressing gene HaHB4 so as to preserve the main trait of interest, i.e., drought tolerance, without affecting other agricultural capabilities.

Furthermore, application AR090110A1 discloses modified gene HaHB4, particularly HaHB4.2, inducible by water deficit and abscisic acid encoding a modified sunflower transcription factor type HD-Zip, particularly mod1HaHB4. Said publication discloses generation and characterization of modified HaHB4.2 expression constructs and its introduction in model plant *Arabidopsis thaliana*. Additionally, this publication generally discloses generation and selection of soybean, wheat and corn transgenic events containing HaHB4.2 gene.

DETAILED DESCRIPTION OF THE INVENTION

The present invention provides abiotic stress-resistant soybean plants containing event IND-00410-5. Said plants present advantages regarding growth in unfavorable environmental conditions allowing a higher yield.

More specifically, the present invention refers to soybean event designed as IND-00410-5, having a representative seed deposited with the American Type Culture Collection (ATCC) with access number PTA-125535 and the progeny derived thereof.

The present invention also includes soybean plants comprising IND-00410-5 represented by SEQ ID NO: 1.

The transgenic insert present in the event of the invention and in registered seed, comprises the following genes: a single copy of the selectable bar marker-gene, and a single copy of the gene conferring abiotic stress-tolerance HaHB4. The bar gene derived from *Streptomyces hygroscopicus*, encodes PAT (Phosphinothricin Acetyl Transferase) protein. Gene HaHB4 derives from sunflower plant, sp. *Helianthus annuus*, and encodes for a protein type HD-Zip I having a protein domain of homeodomain-type associated to a leucine zipper conferring abiotic stress-tolerance, mainly drought. Regulation of genes of interest may be directed by different promoter sequences with different expression levels, sensitivity and tissue specificity. Those skilled in the art know that any promoter or nucleic acid terminator directing or regulating expression of a gene of interest may be used without changing the essence of the invention. Particularly, the event developed in the present invention contains partial duplication of the promoter of cauliflower mosaic virus (CaMV) 35S, 2×35SCaMV version, and terminator vsp for the bar gene conferring resistance to glufosinate ammonium herbicide. Furthermore, the event comprises the greatest length variant of gene HaHB4 promoter (LPF) and nos terminator to regulate the expression of HaHB4 encoding region (FIG. 1).

Other aspects of the invention comprise the progeny of soybean plants, seeds and/or renewable parts of plants, seeds and progeny comprising soybean event IND-00410-5, as well as food products for human or animal consumption derived thereof. The invention also includes parts of plants comprising event IND-00410-5, comprising, without limitation, pollen, ovules, flowers, shoots, roots, leaves, cell vegetative nuclei, and other plant cells comprising event IND-00410-5. The invention also refers to soybean plants comprising soybean event IND-00410-5 having tolerance to multiple abiotic stresses: drought, salinity, low and high temperatures, excess of radiation, low nutrient availability, soil compaction, etc., and combinations thereof.

The present invention refers in part to the cultivation of plants tolerant to abiotic stresses. It also includes a novel event of soybean plant transformation comprising a polynucleotide, as described herein, inserted in a specific site within soybean genome that provides particular genetic and phenotypic characteristics.

In some embodiments, said event/polynucleotide may be "stacked" with other traits including, for example, agronomic traits, and herbicide and/or insect tolerance. However, the present invention includes plants having the individual event, as described herein.

Additional traits may be stacked within plant genome or in the same locus as event IND-00410-5, for example, by means of plant crossing, retransformation of transgenic plant containing event IND-00410-5 or addition of new traits through integration directed by homologous recombination.

In an embodiment, the present invention embraces a soybean chromosomal site located in chromosome 9. In some embodiments, the directed site comprises a heterologous nucleic acid. Soybean chromosomal site is located between flanking sequences set forth in SEQ ID NO: 2 and SEQ ID NO: 3.

In an embodiment, the present invention embraces a method for producing soybean transgenic plants, comprising the insertion of a heterologous nucleic acid in a specific position within chromosome 9.

In particular, the method comprises transforming in a stable form a cell or cell culture with DNA sequences SEQ ID NO: 43 and regenerate the cell originating a new whole plant.

Transformation of said plant cell may be performed through diverse techniques, whether physical, viral, chemical, among them: bio-ballistics, electroporation, bacterial transformation, or a combination thereof. All these techniques are well known by a person skilled in the art.

The invention also presents a microorganism comprising a nucleic acid molecule having a nucleotide sequence selected from the group consisting of SEQ ID NO: 4.

Particularly, the present invention uses *Agrobacterium tumefaciens* transformed with DNA molecule of SEQ ID NO: 43, more precisely transformed with the plasmid pIND2-HB4 (FIG. 1).

Furthermore, the present invention provides tests for detecting the presence of the present event in a soybean sample. Tests can be based on the DNA sequence of the recombinant construct inserted within the soybean genome, and on the genomic sequences flanking the insertion site. Kits and conditions useful for testing are also provided.

Therefore, the present invention in part refers to cloning and analysis of DNA sequences of the whole insert or part thereof and the flanking regions (in transgenic soybean lines). These sequences are unique. Event-specific primers may be generated based on these inserts and flanking (and union) regions. PCR technique evidenced that these events can be identified through the analysis of amplicons generated by these sets of event-specific primers. Therefore, these and other related procedures may be used to identify, in an unequivocal manner, soybean lines comprising the present invention event.

The present invention also refers in part to PCR assays. Among others: quantitative real time PCR or end-point PCR, for detection of IND-00410-5 event, amplicons, and fragments thereof.

The invention also presents DNA molecules comprising a sufficient portion of the contiguous nucleotide sequence of SEQ ID NO: 4 to operate as a DNA probe hybridizing under stringent conditions to a DNA molecule comprising a nucleotide sequence selected from the group consisting of SEQ ID NO: 1 and not hybridizing under stringent conditions to a DNA molecule not comprising a nucleotide sequence selected from the group consisting of SEQ ID NO: 1.

In some instances, the probes used may be labelled with molecules that emit a detectable signal. An example of such molecules are fluorochromes. That is, oligonucleotides presenting fluorochromes at both ends and having a sequence complementary to part of the DNA fragment to be amplified. Non limiting examples are FAM, TET, HEX, JOE, CAL Fluor®, Quasar®, and Pulsar® dyes.

The invention also discloses a pair of DNA molecules consisting of a first DNA molecule and a second DNA molecule different from the first DNA molecule, wherein each of the first and second DNA molecules comprise a sufficient portion of contiguous nucleotides of SEQ ID NO: 1 to operate as DNA probes if used together in an amplification reaction with DNA derived from event IND-00410-5 to produce a DNA amplicon diagnostic for soybean transgenic event IND-00410-5 in a sample.

The invention also describes a method for detecting the presence of DNA obtained from event IND-00410-5 in a sample, said method comprising comparing the sample with the DNA molecules used as probe and primers, subjecting them to the same stringent hybridization conditions, and detecting hybridization of the DNA probe to DNA in the amplified sample with the use of specific primers, wherein said hybridization indicates the presence of DNA derived from soybean transgenic event IND-00410-5 in said sample.

The invention further presents a method for detecting the presence of a DNA molecule obtained from soybean transgenic event IND-00410-5 in a sample, comparing the DNA preparation derived from said sample with a pair of oligonucleotides used as primers to produce an amplification reaction sufficient to produce a DNA amplicon comprising a sequence selected from the group consisting of SEQ ID NO: 1, and detecting the presence of the DNA amplicon in the reaction, wherein the presence of the DNA amplicon in the reaction indicates the presence of a DNA molecule derived from IND-00410-5 in said sample.

The invention further presents a DNA detection kit comprising at least one DNA molecule with sufficient amount of contiguous nucleotides of SEQ ID NO: 1 to operate as primer or specific DNA probe to detect the presence of DNA derived from soybean transgenic event IND-00410-5, wherein DNA detection is diagnostic for the presence of soybean transgenic event IND-00410-5 in a sample.

The invention further presents a soybean plant, seed, cell, or a part of said plant comprising a nucleic acid molecule selected from the group consisting of SEQ ID NO: 1. The invention further presents a soybean plant, seed, cell, or a part plant thereof tolerant to abiotic stresses. The invention further presents a soybean plant, seed, cell or part plant thereof, the genome of which produces an amplicon comprising a DNA molecule selected from the group consisting of SEQ ID NO: 1 when tested with a DNA amplification method.

The invention further presents a soybean plant or seed, wherein the soybean plant or seed is generated from soybean transgenic event IND-ØØ41Ø-5, or is a hybrid or heterozygous having at least one parent derived from soybean transgenic event IND-ØØ41Ø-5.

The invention further presents a nonliving plant material comprising a recombinant DNA molecule selected from the group consisting of SEQ ID NO: 1.

The invention further presents a commodity product produced as a consequence of soybean transgenic event IND-ØØ41Ø-5 and comprises a nucleic acid molecule selected from the group consisting of SEQ ID NO: 1, wherein detection of a nucleotide sequence in a sample derived from de commodity product determines that the commodity product derives from soybean transgenic event IND-ØØ41Ø-5.

The invention further presents a commodity product selected from the group consisting of whole or processed seeds, oil, meal, flour, flakes, biodiesel, biogas, or other biomaterials, etc. The invention also presents a method for producing a commodity product by obtaining a soybean plant or a part thereof comprising the soybean transgenic event IND-ØØ41Ø-5 and producing a soybean commodity product from the soybean plant or a part thereof.

The invention presents a method of producing a soybean plant tolerant to abiotic stresses by crossing a plant with the soybean transgenic event IND-ØØ41Ø-5 comprising a nucleic acid molecule selected from the group consisting of SEQ ID NO: 1 with a second soybean plant, thereby producing seeds, collecting the seeds produced from the cross, growing the seeds to produce a plurality of progeny plants, and selecting a progeny plant that is tolerant to abiotic stresses.

BRIEF DESCRIPTION OF THE DRAWINGS

FIG. 10. Junction Sequence Analysis of event IND-ØØ41Ø-5. A vertical line in the sequence alignment indicates the junction between the T-DNA and the soybean chromosome. Columns from left to right: vector name, position of the JS in the vector, numbers of read supporting JS, name of the read, and the partial sequence. Last row, fourth column in each JS, indicates the element where the JS begins. The insertion site and structure were confirmed by assembling the raw sequence data de novo using the Velvet assembler software (sequences were aligned considering only the last 30 bases of the T-DNA insert; all the Illumina-generated reads were 101 bp long).

BRIEF DESCRIPTION OF THE SEQUENCES

Figure 1:
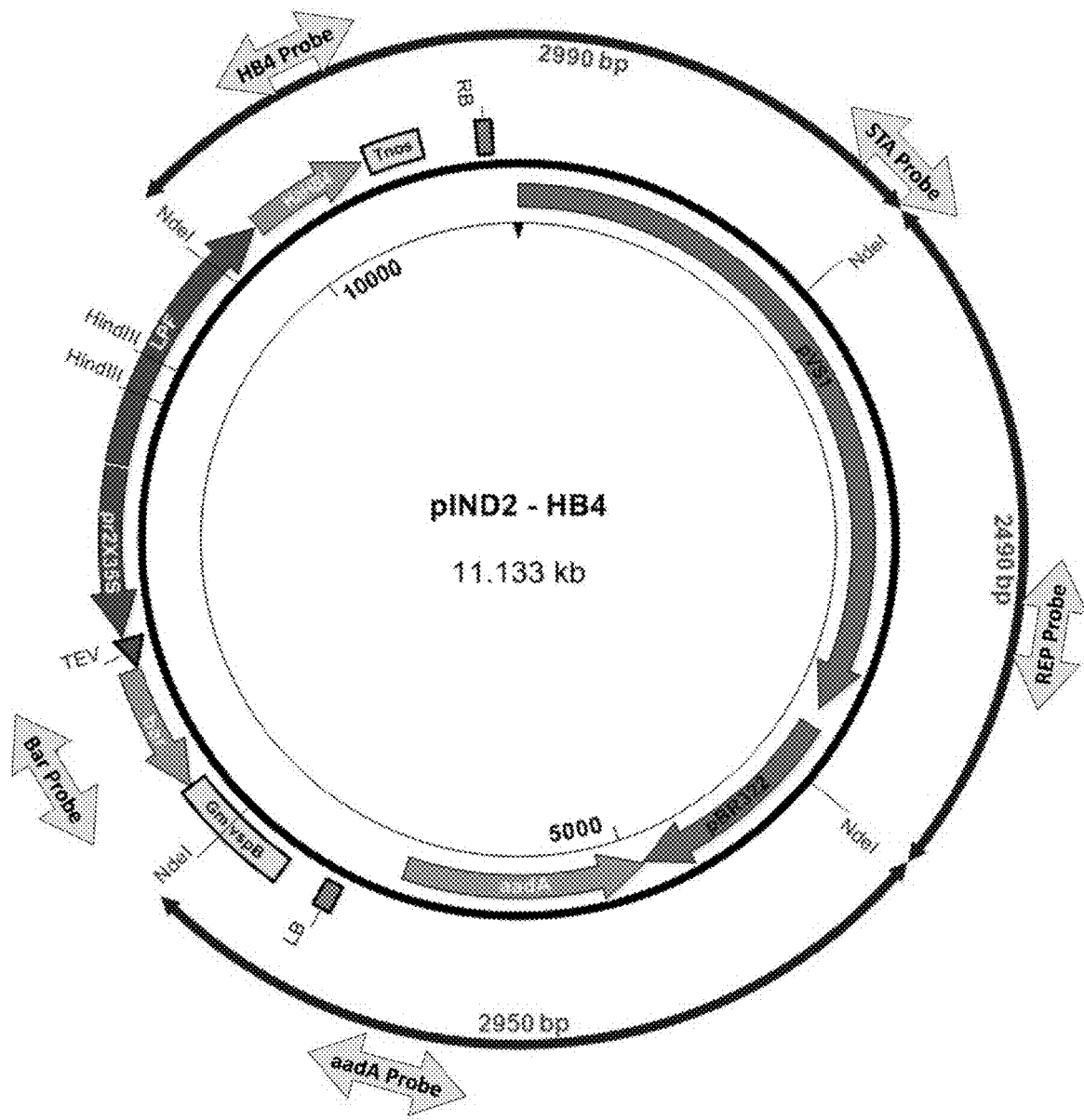
FIG. 1. Map of the plasmid pIND2-HB4. a) Binary vector plasmid with the T-DNA. The fragments resulting from NdeI digestion are indicated as Left Right arrows along with their sizes. LB, left border; RB, right border. Probes are presented in thick Left Right arrows. b) Detailed T-DNA portion of the pIND2-HB4 plasmid. HindIII digest fragments are presented as arrows along with their minimum respective sizes to the LB and RB, respectively. NdeI digest fragments are presented. The expected size of the NdeI internal digest was 2703 bp long.

SEQ ID NO: 1 DNA sequence corresponding to insert and contiguous genomic regions.
SEQ ID NO: 2 DNA sequence corresponding to right flanking sequence.
SEQ ID NO: 3 DNA sequence corresponding to left flanking sequence.
SEQ ID NO: 4 DNA sequence corresponding to insert.
SEQ ID NO: 5 DNA sequence corresponding to primer 750.
SEQ ID NO: 6 DNA sequence corresponding to primer 751.
SEQ ID NO: 7 DNA sequence corresponding to primer 752.
SEQ ID NO: 8 DNA sequence corresponding to primer 753.
SEQ ID NO: 9 DNA sequence corresponding to primer 754.
SEQ ID NO: 10 DNA sequence corresponding to primer 755.
SEQ ID NO: 11 DNA sequence corresponding to primer 756.
SEQ ID NO: 12 DNA sequence corresponding to primer 757.
SEQ ID NO: 13 DNA sequence corresponding to primer 758.
SEQ ID NO: 14 DNA sequence corresponding to primer 759.
SEQ ID NO: 15 DNA sequence corresponding to primer 760.
SEQ ID NO: 16 DNA sequence corresponding to primer 2527.
SEQ ID NO: 17 DNA sequence corresponding to primer 203.
SEQ ID NO: 18 DNA sequence corresponding to primer 378.
SEQ ID NO: 19 DNA sequence corresponding to primer 1970.
SEQ ID NO: 20 DNA sequence corresponding to primer 1747.
SEQ ID NO: 21 DNA sequence corresponding to primer 1748.
SEQ ID NO: 22 DNA sequence corresponding to primer 1745.
SEQ ID NO: 23 DNA sequence corresponding to primer 1746.
SEQ ID NO: 24 DNA sequence corresponding to primer 822.
SEQ ID NO: 25 DNA sequence corresponding to primer 1127.
SEQ ID NO: 26 DNA sequence corresponding to primer 817.
SEQ ID NO: 27 DNA sequence corresponding to primer 818.
SEQ ID NO: 28 DNA sequence corresponding to probe 819.
SEQ ID NO: 29 DNA sequence corresponding to primer 868.
SEQ ID NO: 30 DNA sequence corresponding to primer 752.
SEQ ID NO: 31 DNA sequence corresponding to primer 530.
SEQ ID NO: 32 DNA sequence corresponding to primer 531.
SEQ ID NO: 33 DNA sequence corresponding to probe 532.
SEQ ID NO: 34 DNA sequence corresponding to primer 527.
SEQ ID NO: 35 DNA sequence corresponding to primer 528.
SEQ ID NO: 36 DNA sequence corresponding to probe 529.
SEQ ID NO: 37 DNA sequence corresponding to primer 718.
SEQ ID NO: 38 DNA sequence corresponding to primer 719.
SEQ ID NO: 39 DNA sequence corresponding to probe 720.
SEQ ID NO: 40 DNA sequence corresponding to primer 934.
SEQ ID NO: 41 DNA sequence corresponding to primer 935.
SEQ ID NO: 42 DNA sequence corresponding to probe 936.
SEQ ID NO: 43 DNA sequence corresponding to pIND2-HB4 plasmid.

DETAILED DESCRIPTION

The following definitions and methods are presented to better define the invention and to enable those skilled in the art to reduce the invention to practice. Unless otherwise stated terms are to be construed according to the conventional use by those skilled in the relevant art.

EXAMPLES

Example 1: Construction of Plasmid pIND2-HB4

The plasmid pIND2-HB4 that would be subsequently used for transformation of soybean plants derives from the binary plasmid family pPZP, in particular, is based on the series pPZP200.

The transgenic insert and expression cassette of IND-ØØ41Ø-5 comprise the 2× cauliflower mosaic virus (CaMV) promoter 35S and the vsp terminator for bar marker gene. Additionally, comprise the sunflower gene HaHB4 promoter (Large Promoter Fragment, LPF) and nos terminator for gene HaHB4. The plasmid obtained, pIND2-HB4, is schematized in FIG. 1.

Example 2: Transformation of Soybean Plants and Selection of Event IND-ØØ41Ø-5

Soybean cell may be transformed through a variety of methods. Particularly, *Agrobacterium tumefaciens* strain EHA 101 (Hood et al., 1986), disarmed, transformed with the binary plasmid containing HaHB4 and bar within the T-DNA region (transference DNA) was used. The transformation was made using a modification of the method described by Paz et al., (2004). Briefly, soybean seeds (*Glycine max* cv. Williams 82) were pre-germinated in basal medium in the dark. Cotyledonary nodes were isolated from half-mature seeds, which were infected with *Agrobacterium*. During 5-7 days, the explants were cultured in the dark with the *Agrobacterium* strain. Medium for shoot initiation, elongation and rooting was supplemented with cefoxatime, timentin and vancomycin to inhibit *Agrobacterium* overgrowth. Shoots transformed using ammonium glufosinate (which inhibits the development of shoots not expressing PAT) were selected. The regenerated explants were maintained at 24° C. for two/three weeks under white fluorescent light and with photoperiodic lighting 16:8. During shoot induction, the explants were subcultured several times in shoot induction selective medium (SISM) containing Gamborg basal medium (macronutrients B5 1×, micronutrients B5 1×, vitamins B5 1×, Ferrous 28 mg/L, NaEDTA 38 mg/L), sucrose 30 g/L, MES 0.59 g/L and agar type A 7 g/L, pH 5.7. After medium autoclaving, filtered and sterilized BAP (2 mg/L), IBA (0.2 mg/L), Timentin (50 mg/L), Cefotaxime (100 mg/L), and Vancomycin (50 mg/L), and the selective agent were added. As soon as leaves were visible, their stems were cut and transferred to a shoot elongation selective medium (SESM). The elongated shoots (two nodes) were transferred to a semisolid rooting medium (RM: basal medium modified with Gamborg vitamins MS ½× (macronutrients MS ½×, micronutrients MS ½×, Vitamins B5 ½×, Ferrous 28 mg/L, NaEDTA 38 mg/L), sucrose 20 g/L, MES 0.59 g/L and agar type A 7 g/L, pH 5.6). After medium autoclaving, filtered and sterilized indole-3-butyric acid (IBA, 2 mg/L), and selective agent were added. Rooted plants with normal phenotypic characteristics were transferred to plots containing substrate mixture for seedlings acclimatization, inducing their growth for further analyses.

TABLE 1

Micronutrients and macronutrients composition of Gamborg basal medium B5

| Macronutrients | |
|---|---|
| $(NH_4)_2SO_4$ | 0.134 g/l |
| $KNO_3$ | 2.528 g/l |
| $MgSO_4.7H_2O$ | 0.246 g/l |
| $CaCl_2.aq$ | 0.15 g/l |
| $KH_2PO_4$ | 0.15 g/l |

| Micronutrients | |
|---|---|
| KI | 0.75 mg/l |
| $H_3BO_3$ | 3.0 mg/l |
| $MnSO_4.H_2O$ | 10 mg/l |
| $ZnSO_4.7H_2O$ | 2.0 mg/l |
| $Na_2MoO_4.2H_2O$ | 0.25 mg/l |
| $CuSO_4.5H_2O$ | 0.025 mg/l |
| $CoCl_2.6H_2O$ | 0.025 mg/l |
| $Na_2.EDTA$ | 37.3 mg/l |
| $FeSO_4.7H_2O$ | 27.8 mg/l |

Plants Regeneration and Event Selection

I) Seeds Sterilization:

Seeds were washed in a diluted solution of aqueous detergent for 5 minutes and subsequently washed 6 times with sterilized distilled water. Then, seeds were washed with alcohol (ethanol 70%) for one to two minutes with occasional agitation. After settling of the ethanol solution, seeds were placed in a bell jar desiccator with a stem cover for chlorine gas disinfection. After gaseous disinfection, seeds are imbibed in distilled water for 12 hours to soften their teguments.

II) Seeds Germination:

Seeds were peeled and placed in germination medium (GM: basal medium Murashige & Skoog with salts and vitamins, Sucrose 30 g/l, and agar type A 7 g/l, pH 5.8) for a period of time of 72-96 hours approximately in the dark up to radial elongation. After pre-germination period, roots and hypocotyledonous stem were extracted. Adaxial epidermis was partially removed mechanically from both cotyledons to increase inocula contact with explant cells enhancing efficiency of *Agrobacterium tumefaciens* infection.

III) Transformation Proceedings a) Explants Directly Co-Cultivated with *Agrobacterium tumefaciens* by Infiltration.

Pre-germinated seeds were contacted with an infection medium through vacuum infiltration (VIIM: Gamborg basal medium B5 ¹⁄₁₀× (macronutrients B5 ¹⁄₁₀×, micronutrients B5 ¹⁄₁₀×, vitamins B5 ¹⁄₁₀×, Ferrous 2.8 mg/L, NaEDTA 3.8 mg/L), Sucrose 30 g/L, MES 3.9 g/L, pH 5.4. After medium autoclaving GA3 filtered and sterilized (0.25 mg/L), BAP (2 mg/L), Silwet L-77 (0.03%) and 40 mg/L acetosyringone) containing a bacterial suspension (direct co-culture) were added to this medium. Vacuum was raised to 450 mm Hg. The explants were maintained under vacuum conditions for 5-7 minutes. This process was repeated twice.

b) Seeds Dissection and Indirect Co-Culture of the Same with Transformed *Agrobacterium tumefaciens*

After seed infiltration proceeding, seeds were dried with sterile filter paper and placed on a sterile plane surface (empty plate) for dissection. Cotyledons were broken separately using a sharp sterile scapel and the plumula was removed.

c) Explants Indirectly Co-Cultured

An additional treatment involving dehydration/rehydration of half of seed explants was included to favour bacterial infection. Loss of turgor was induced in half seed explants dissected under laminar flow hood for 30 minutes. Then, explants were rehydrated in infection medium (IM: Gamborg basal medium B5 ¹⁄₁₀× (macronutrients B5 ¹⁄₁₀×, micronutrients B5 ¹⁄₁₀×, vitamins B5 ¹⁄₁₀×, Ferrous 2.8 mg/L, NaEDTA 3.8 mg/L), Sucrose 30 g/L, MES 3.9 g/L, pH 5.4. After autoclaving GA3 filtered and sterilized (0.25 mg/L), BAP (2 mg/L) and 40 mg/L acetosyringone) containing a suspension of *Agrobacterium* (DO 0.7) at 24° C. for 30 minutes were added to this medium. Explants were dried with sterile paper and immediately transferred to co-culture medium (CCM: Gamborg basal medium B5 ¹⁄₁₀× (macronutrients B5 ¹⁄₁₀×, micronutrients B5 ¹⁄₁₀×, vitamins B5 ¹⁄₁₀×, Ferrous 2.8 mg/L, NaEDTA 3.8 mg/L), Sucrose 30 g/L, MES 3.9 g/L and agar type A 4.25 g/L, pH 5.4. After autoclaving GA3 filtered and sterilized (0.25 mg/L), BAP (2 mg/L), cysteine (400 mg/L), dithiothreitol (154.2 mg/L) and 40 mg/L acetosyringone) were added to this medium for 5-7 days in the dark at 24° C.

d) Rinse

Explants were gently steered in sterile water for 10 minutes to remove the bacteria adhered to them, and then were dried with sterile paper filter. Then, explants were submerged in shoot induction washing medium (SIWM: Gamborg basal medium B5 1× (macronutrients B5 1×, micronutrients B5 1×, vitamins B5 1×, Ferrous 28 mg/L, NaEDTA 38 mg/L), Sucrose 30 g/L, y MES 0.59 g/L, pH 5.7. After autoclaving the medium filtered and sterilized BAP (1 mg/L), TDZ (0.1 mg/L), IBA (0.2 mg/L) Timentin (100 mg/L), Cefotaxime (100 mg/L), and Vancomycin (50 mg/L) (25 explants per bottle) were added. Washing continued for 6-12 hours with continuous agitation (100 rpm) at 24° C., with photoperiodic lighting 16:8.

e) Selection and Regeneration of Transformed Explants

Explants were transferred to shoot induction selective medium (SISM) and were maintained at 24° C. for two weeks under white fluorescent light and with photoperiodic lighting 16:8. They were placed with adaxial face upwards on the surface of the selective medium. Petri plates (100×25 mm) were used for selection and regeneration process. Each two weeks, explants were sub-cultured in fresh medium SISM supplemented with phytohormones and antibiotics. When leaves appeared, stems were removed and transferred to plates with selective medium for shoot elongation (SESM: Gamborg basal medium modified with vitamins MS 1× (macronutrients MS 1×, micronuctrients MS 1×, Vitamins B5 1×, Ferrous 28 mg/L, NaEDTA 38 mg/L), Sucrose 30 g/L, MES 0.59 g/L and agar type A 7 g/L, pH 5.7. After autoclaving this medium asparagine (50 mg/L), L-pyroglutamic acid (100 mg/L), IAA (0.1 mg/L), GA3 (0.5 mg/L), Zeatin-R (1 mg/L), IBA (0.2 mg/L), Timentin (50 mg/L), Cefotaxime (100 mg/L), Vancomycin (50 mg/L) were added.

f) Rooting of Transgenic Shoots

Elongated shoots (two nodes) were transferred to culture flasks (1 plant/250×25 mm flask) containing semisolid rooting medium (RM).

Then, the transgenic plants were transferred to plots in an environment subjected to growing conditions to induce greater selection and perform their phenotypic and molecular characterization.

Selection was made based on the presence of a "wild" phenotype in normal growing conditions and a higher tolerance to environmental stress, expressed through a greater production in agricultural zones with less favourable conditions for cultivation.

Event Preliminary Selection

Soybean transgenic events were generated by Agrobacterium-mediated protocol in the cultivar Williams 82. T1 seeds were obtained for 35 independent events using three different expression cassettes and strategies. The first multiplication was conducted in a greenhouse and ten T1 individuals derived from each event were sampled for a Mendelian segregation test by PCR determination. After this analysis the lines with not Mendelian segregation were discarded. Lines derived from selfings of individuals from selected events (3:1 Mendelian segregation in T1) were sowed. Off-type phenotypes with penalties were identified throughout the growing season and discarded. During the vegetative stages, plants were sampled for PCR analysis to identify homozygous lines. Seed increase (T3 seed) of homozygous and null lines was conducted in a greenhouse.

To continue with the event selection, fifteen HB4 soybean selected transgenic events and control lines were evaluated under field conditions. Two levels (low and high) of irrigation regime were applied. For low irrigation regime the water supply was suspended from R1 to R6 developmental soybean stages. Therefore, this regime consisted of only two water applications, one at the beginning of the season and the other one at the end.

Homozygous transgenic events lines within or between constructions, and within the same line, had higher yield than the not transgenic lines. There were significant yield differences between transgenic and not transgenic lines for two inducible transgenic events, one (b) (pIND2:HB4) and one (c) (pIND3:HB4), within the same line. Furthermore, two constitutive (a) (pIND1:HB4) transgenic events had higher yield than its not transgenic counterparts. These four events were selected to continue with the deeper characterization that would allow the selection of an event.

Soybean Transgenic Events and Genetic Constructs

Figure 2:
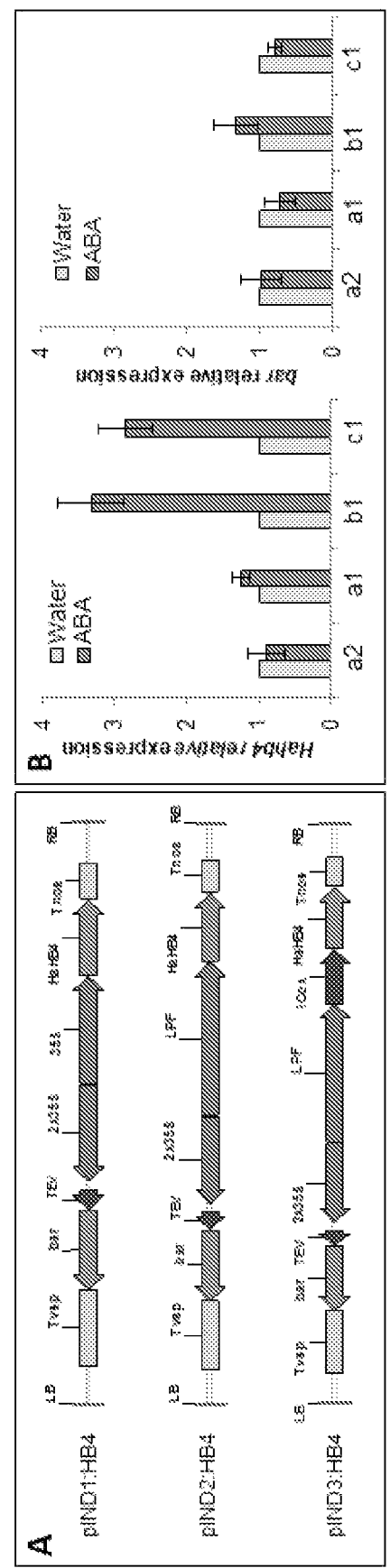
FIG. 2. Transformation constructs and expression levels of HB4 events. A—Genetic description of the regulatory elements in the three different plasmids (a, b and c) used for obtaining the (pIND1:HB4=a), (pIND2:HB4=b) and (pIND3:HB4=c) transgenic events. B—Hahb-4 and bar genes relative expression levels. Relative values referred to water control treatment.

Williams 82 soybean genotype was used for transformation with *Agrobacterium tumefaciens* strain EHA101. Transformation vectors consisted on binary plasmids derivatives from pPZP200 series (Hajdukiewicz et al., 1994). The bar gene from *Streptomyces hygroscopicus*, present in the plasmids, was used as selectable marker (Thompson et al., 1987). In order to evaluate the effect of different levels of expression on growth and tolerance response, three different promoters were used for Hahb-4 expression. A constitutive expression of the Hahb-4 TF was obtained using the Cauliflower mosaic (CaMV) 35s promoter and, an inducible expression was obtained using two different Hahb-4 promoter regions. The difference between the inducible promoters is the presence or absence of the COX5c intron (FIG. 2A). Constructs were similar to the described in Cabello et al. (2007). Transgenic plants from the first generation (T0) were selected using herbicide (ammonium glufosinate) sprays. The following generations (T1 and T2) were selected by detection of the HaHb-4 cDNA and regulatory sequences using PCR. Several homozygous lines were obtained and, after a preliminary analysis, four transgenic independent events (a1, a2, b1 and c1) were selected for further evaluation. Preliminary analysis consisted on visual observations and selection of events with phenotype without altered morphology.

HaHB4 and Bar Genes Transcriptional Expression Analysis

The HaHB4 and bar genes expression levels on homozygous lines were evaluated by transcriptional expression analysis. Seedlings of each transgenic event were treated either with a solution of ABA 100 μM for 1-hour or with water as the control treatment. The experiment was conducted three times and five seedlings were sampled at each individual experiment. After treatment period, total biomass of seedlings was harvested and immediately placed in liquid nitrogen. From the samples, RNA for quantitative RT-PCR was isolated using TriPure reagent (ROCHE). RNA (1 μg) was incubated with RQ1 DNAse (Promega, Madison, WI, USA) according to manufacturer's instructions and then used for reverse transcription reactions using the Transcriptor First Strand cDNA Synthesis Kit (ROCHE). Quantitative PCRs were conducted using the LightCylcer® 480 II apparatus (ROCHE) in a 20 μl final volume using LightCycler® 480 SYBR Green I Master kit. Fluorescence was measured at 80-84° C. during 40 cycles. Primers used for quantification procedures were designed to work at 60° C. of annealing temperature and melting curves were analyzed for detecting unspecific amplification products. In every case, gene expression analysis was performed by triplicate and the relative expression level of transcripts was calculated using the Ct values obtained for each sample as described by Pfaffl (2001).

Water Stress Under Controlled Condition Experiments

The experiment consisted on five genotypes (transgenic events a1, a2, b1, c1, and Williams 82), two water treatments (well-watered and water-stress), three stress onset periods: second node (V2), full bloom (R2) and full pod (R4) (Fehr and Caviness, 1977), and 15 replications. Pots (5-L) were filled with commercial GrowMix MultiPro (Terrafertil SA, AR). Three seeds were planted in each individual pot. At emergence, plants were thinned to one plant per pot. Water stress was imposed from V2, R2, and R4 developmental stages by completely withholding watering. The remaining control pots were maintained at field capacity until maturity.

After first appearance of wilting symptoms in the Hahb-4 plants, pots were watered until field capacity. A recovery rate (%), after a 7-days recovery period, for each genotype and developmental stage was calculated as the number of plants without symptoms of wilting divided by the total number of plants at the beginning of the experiment.

Ethylene Sensitivity Experiments

Soybean leaves (15 leaves per genotype) of a1 and b1 transgenic events and control plants (Williams 82) were detached from plants growing under controlled conditions at V4 developmental stage. Detached leaves were placed in Petri dishes and incubated with: a—water and left under normal light conditions (control treatment); b—water and covered with aluminum foil (darkness treatment) and, c—with a solution of 2-chloroethilphosfonic acid 100 μM (Ethephon treatment) (Tifón, Gleba, AR). After a 7-days treatment period, pigments extraction and quantification were conducted on the recovered leaves.

For chlorophyll (A and B) and photosynthesis-related carotenoid determinations, leaves were grinded in liquid nitrogen and left overnight on darkness in a solution with ethanol 99.9%. An aliquot of the ethanol solution was used for further UV/Vis spectroscopy quantification. Serial dilutions were conducted from each aliquot to avoid outliers in the absorption spectrum. Visible electronic absorption spectra of chlorophyll A and B and carotenoids were recorded at 15° C. using a JASCO V-550 spectrophotometer (Jasco Analytical Instruments, MD, USA). A spectral scanning between wavelength of 350 nm and 750 nm was conducted for each sample. The values of the entire experiment are the average of three independent experiments. In order to evaluate one of the "triple response" morphological effects of ethylene, soybean seeds of the a1, b1 and control genotypes were placed in germination trays with filter paper with either water or a solution of 25 μM of 2-chloroethilphosfonic acid. A total of 3 trays (20 seeds each) per genotype and treatment were used. Trays were covered with aluminum foil for 48 hours. After hypocotyl emergence, a quantification of seeds with hook formation was conducted.

Water Loss Experiment

Three plants of each soybean transgenic event (a1, a2, b1 and c1) and the non-transgenic control (Williams 82) were grown in 5-L pots with GrowMix MultiPro soil under normal watering conditions. At the beginning of bloom (R1) (Fehr and Caviness, 1977), 10 leaves of each plant were detached and immediately weighted in an air-isolated analytical balance at intervals of 1 hour for 10 hours.

Field Experiments Under Rainfed Field Conditions

Transgenic events a1, a2, b1, c1, and the wild-type (Williams 82) were evaluated for yield and yield components in 12 environments during the 2012-13 growing season. Environments were defined as a combination of location and planting date, since for some of the locations two planting dates were sowed. Field trials locations were Monte Buey (Córdoba), Chilibroste (Córdoba), Corral de Bustos (Córdoba), Villa Saboya (Buenos Aires), Carmen de Areco (Buenos Aires), San Agustin (Buenos Aires), Landeta (Santa Fe), Hughes (Santa Fe) y Aranguren (Entre Rios). At San Agustin, Carmen de Areco and Aranguren, two planting dates were planted. Environments were grouped based on yield of the wild-type genotype (environmental index). Three environmental index (low, medium and high) were defined considering different criteria: 1) allowing for event selection maximizing the yield difference between the events and the non-transgenic control; 2) representing the Argentina national yield average (upper limit for the low environmental index) and the average yield of the two most productive areas of Argentina (lower limit for the high environmental index) at the year of event selection (Bolsa de Cereales, Panorama *Agricola* Semanal 2013, May 30); 3) balance the number of environments within each group. Thus, low environmental index comprise environments where wild-type yield was lower than 2500 kg ha$^{-1}$ (San Agustin, both planting dates, Aranguren, both planting dates and Landeta); medium environmental index encompass environments where wild-type yield was between 2500-3500 kg ha$^{-1}$ (Carmen de Areco, both planting dates and, Villa Saboya); and finally, high environmental index include environments where wild-type yield was higher than 3500 kg ha$^{-1}$ (Corral de Bustos, Hughes, Monte Buey and Chilibroste). Event selection was performed based on seed yield and yield components (seed number per square meter and 100-seed weight) relative performance of the transgenic events and the wild-type. The transgenic relative performance to the wild-type was calculated as a relative difference between the transgenic event and the wild type.

Field trials were planted using a randomized complete block design with 4 to 7 replications, depending on the site considered. Plots consisted on 4-rows, 5 to 6 meters in length and 0.4 to 0.7 meters between rows. The middle two rows of each plot were harvested at full maturity (R8) (Fehr and Caviness, 1977). Yield was expressed on a 13% moisture base. Seed number per square meter was calculated based on 100-seed weight and yield. Seed yield, seed number and seed weight were analyzed with ANOVA using SAS software. The statistical model included environmental index, environment nested within environmental index, block nested within environment, genotype, and the interaction terms (genotype by environmental index and environment by genotype).

After event selection, additional field testing was performed in six environments during the 2013-14 growing season. Field trials locations were Monte Buey (Córdoba), Aranguren (Entre Rios), Rolden (Santa Fe) and Villa Saboya (Buenos Aires). At Aranguren, two experiments were sowed that differ in fertilization treatment at planting: a) 100 kg ha-1 Monoammonium phosphate fertilizer and, b) 0 kg ha-1 Monoammonium phosphate. At Rolden, two planting dates were planted (December and January). Experimental design for the 2013-14 field trials was the same as 2012-13. Data from the two years were pooled and all environments were analyzed together for the comparison between b1 transgenic event and the non-transgenic control. Field trials within the low environmental index were Aranguren, two fertilization conditions. Field trials with medium environmental index were Monte Buey and Roldán (two planting dates). Finally, Villa Saboya was classified as the medium environmental index trial. Data were analyzed using the same statistical model as the previous data set.

Library Construction and Illumina Sequencing

Leaf tissue of Williams 82 and b1 transgenic event were collected from three plants at two different water treatments (well-watered and water-stressed plants), as described in the "Water stress experiment under controlled conditions" section. Tissue samples were collected at R2 stage. Total RNA extraction from leaf tissue was conducted as described in the "Hahb-4 and bar genes expression levels" section, using the SV Total RNA Isolation System (Promega, Madison, WI, USA). RNA quality was evaluated using Agilent 2100 Bioanalyzer Eukaryote Total RNA Nano (Agilent, Santa Clara, California, USA), and RNA concentration was determined using Quant-iT RiboGreen RNA Assay Kit (Thermo Fisher Scientific, Waltham, Massachusetts, USA).

RNAseq differential expression assay was designed using a single factor scheme, two levels (water stressed and well-watered) and three biological replicates for each factor level. RNA-seq libraries were constructed using TruSeq RNA Library Prep Kit v2 according to the manufacturer's recommendations (Illumina, San Diego, CA, USA). Library quality check were performed using Agilent 2100 Bioanalyzer DNA 1000 chip (Agilent, Santa Clara, California, USA). Libraries were quantified using KAPA Library Quantification Kits for Illumina platforms (KAPA Biosystems, Wilmington, Massachusetts, USA), pooled, diluted and loaded for further sequencing in an Illumina HiSeq 1500 RR 2×100 pb lane. All samples were sequenced using the next-generation sequencing facilities at Instituto de Agrobiotecnología Rosario (Rosario, Republica Argentina).

Mapping, Differential Expression and Gene Ontology (GO) Enrichment analysis

Raw data quality check was performed using FastQC v0.11.4 (Andrews, S. 2010). Trimming and adapter removal was performed using Trimmomatic v0.33. Paired-end RNA-seq reads were mapped to the *Glycine max* reference genome (phytozome Gmax_275_Wm82.a2.v1) using Bowtie2 v2.2.6 (Langmead and Salzberg, 2012) included in TopHat v2.1.0 (Trapnell et al., 2009) using the default parameters. Cufflinks v2.2.1 (Trapnell et al., 2012) was used for transcripts assembly, abundance estimation was measured using the fragments per kilobase of transcript per million mapped reads (FPKM) and differential expression analysis (FDR=0.05) was done using cuffdiff. The differentially expressed genes were annotated with gene ontology (GO) terms. A Singular Enrichment Analysis (SEA) (Fisher's exact test; 0.05 significance level) was done using the agriGO web server (Zhou D., et al, 2010) with *Glycine max* Wm82.a2.v1 genes as background. To get a broad overview of the transcripts functions we mapped the GO terms to GO slims plant categories using the GOSlimViewer tool. The genes ID were obtained using the phytozome 11.0v repository.

Selection of Event Between Two Constitutive Transgenic Events (a1 and a2) and Two Inducible Transgenic Events, (b) and (c)

Four independent transgenic lines (a1, a2, b1, and c1), belonging to three different constructs, were evaluated for HaHB4 relative expression levels (FIG. 2B). As expected, transgenic events b1 and c1 with the inducible promoter showed higher levels of HaHB4 expression when exposed to abscisic acid (ABA) compared to control plants without phytohormone exposure. On the contrary, transgenic events a1 and a2 with constitutive promoter showed similar HaHB4 expression for both treatments. The expression levels for the bar gene remained similar at both conditions as expected.

Figure 3:
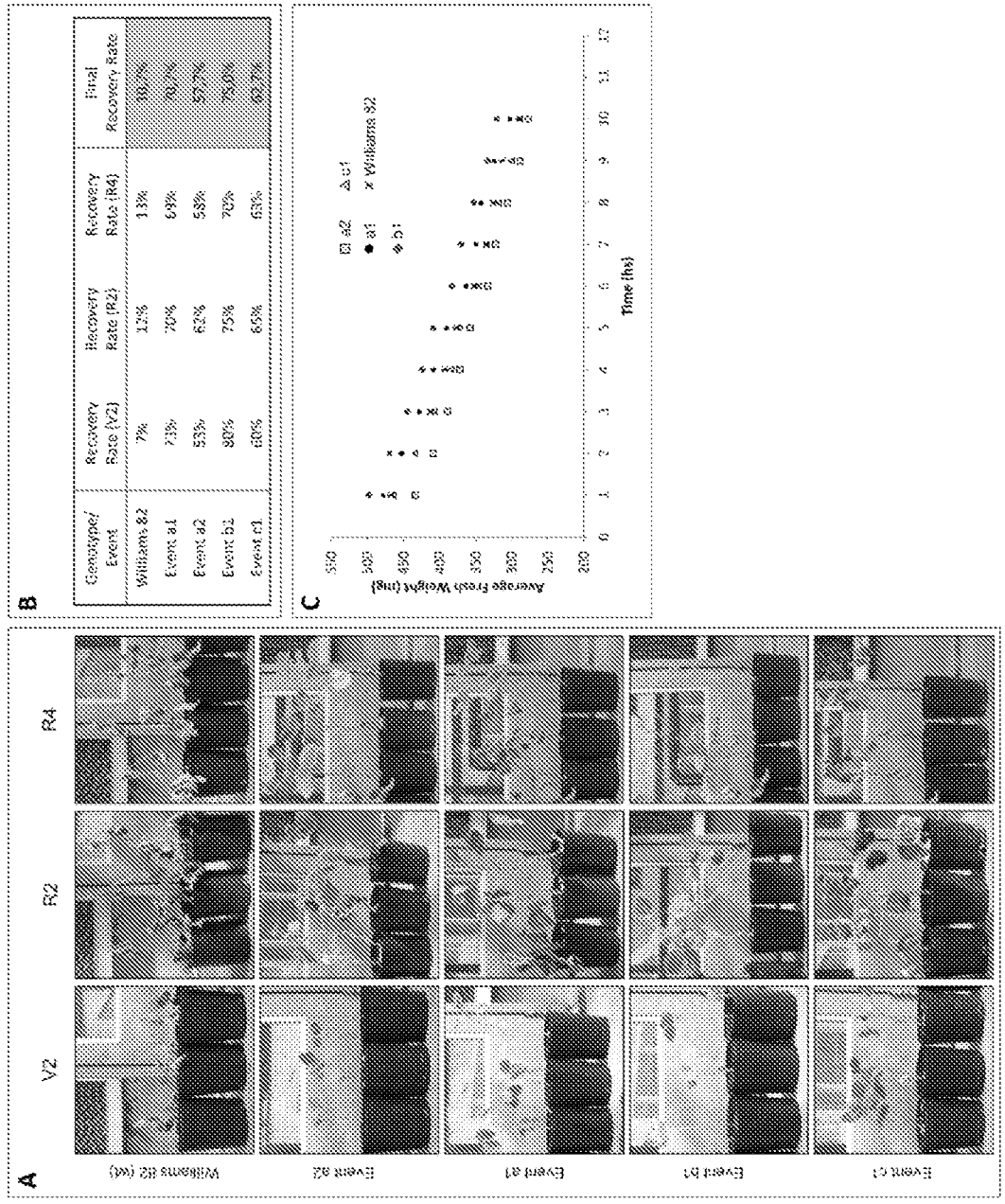
FIG. 3. Water stress tolerance under controlled conditions. A—Representative plants after a period of water deprivation during V2, R2 and R4 developmental stages. B—Recovery rate as the number of plants without wilting symptoms after a period of water restoration, from the total plants used in the experiment. C—Water loss measured at 1-hour intervals for a period of 10 hours, from detached leaves of each transgenic event and the non-transgenic control.

Following expression analysis, drought tolerance experiments were conducted under controlled conditions. Thus, drought tolerance at three different developmental stages was evaluated in the four independent transgenic lines (a1, a2, b1, and c1). After a period of water deprivation, all transgenic lines showed fewer wilted plants compared to non-transgenic plants (Williams 82) (FIG. 3A). Observations of wilting recovery (recovery rate) after a period of water deprivation following irrigation were conducted for each independent transgenic line (FIG. 3B). At V2, second node of developmental stage (Fehr and Caviness, 1977), only 7% of control plants showed tissue recovery while average recovery rate for the transgenic events was 67%. Similar results were found at R2, full bloom, and R4, full pod, developmental stages (Fehr and Caviness, 1977), where recovery rate for control plants was 12% and 13% while transgenic events showed values of 68% and 65%, respectively. A recovery rate averaged across developmental stages (final recovery rate) was calculated to estimate the average performance of each transgenic event. Results showed some differences among transgenic events, with a1 and b1 events showing higher values of final recovery than a2 and c1 events (FIG. 3B).

On the other hand, the rate of water loss from plant-detached soybean leaves was measured at 1-hour intervals during 10-hours to test whether stomata closure regulation contributes to transgenic lines stress tolerance. Results showed that water loss of all independent lines and the wild type were similar, (FIG. 3C) demonstrating that earlier stomata closure is not a mechanism involved in drought tolerance mediated by HaHB4.

Ethylene Sensitivity and Delayed Senescence Evaluations on HaHB4 Transgenic Plants A lower ethylene sensitivity and a consequent delayed senescence would be the main mechanisms conferring higher drought tolerance in HaHB4 *Arabidopsis* transgenic plants (Manavella et al., 2006; Cabello et al., 2007). To evaluate this physiological mechanism in soybean, two independent transgenic lines with different promoters, a1 constitutive and b1 inducible, were selected for evaluation.

Figure 4:
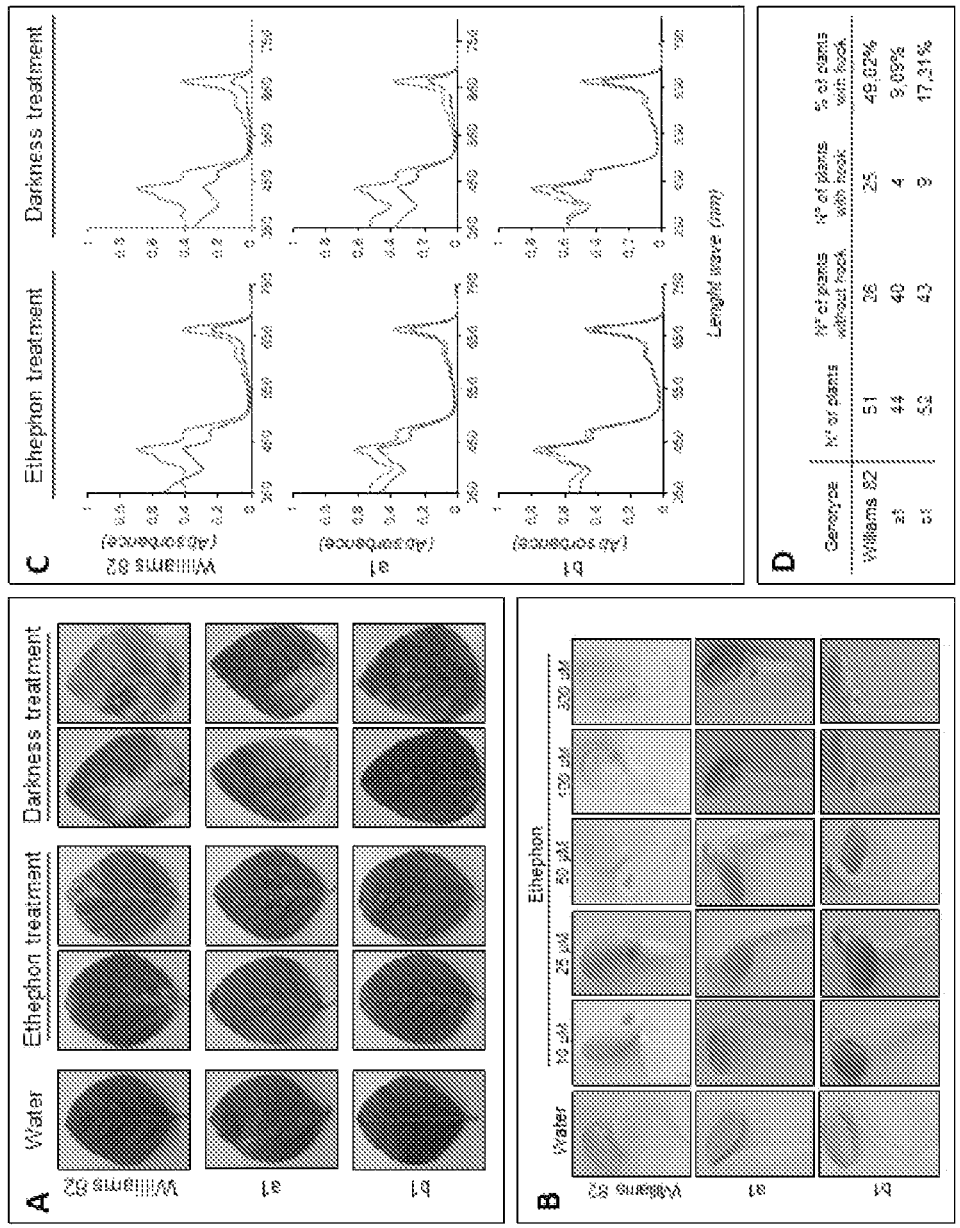
FIG. 4. Ethylene sensitivity and darkness treatment. A—Stay green phenotype on leaves after ethephon and darkness treatments. Stay green phenotype in water treated leaves, as the negative control, is also shown. B—Hypocotyl hook as part of the ethylene triple response, at five ethephon concentrations. C—UV/Vis absorption spectrums from the leaves presented in A. Photosynthesis related carotenoids (pike at 480 nm) and the photosynthetic pigments chlorophyll A and B (pikes at 665 nm and 649 nm respectively) for each genotype. The lines correspond to samples collected from the water treatment and the lines correspond to samples collected from the ethylene/darkness treatments. D—Quantification of seedlings with hypocotyl hook formation at a 25 µM Ethephon solution.

Transgenic line b1 maintained photosynthetic activity longer than the non-transgenic control (Williams 82) when both were exposed to either Ethephon (2-chloroethyl phosphoric acid) exogenous applications or darkness to trigger tissue senescence. Leaves of transgenic line b1 treated with Ethephon or under darkness showed similar abundance of chlorophyll, A and B, and photosynthesis related-carotenoids than non-stressed leaves (FIG. 4C). On the contrary, the non-transgenic control genotype showed lower levels of chlorophyll, A and B and carotenoids when leaves were treated with ethephon or darkness, compared to non-stressed leaves. An intermediate response was found for the transgenic event with a constitutive response (a1). Longer delayed senescence was also observed in transgenic b1 leaves when exposed to ethephon or darkness (FIG. 4A). Thus, while transgenic b1 leaves showed stay-green phenotype, the non-transgenic line showed yellowing symptoms under these treatments.

On the other hand, ethylene application to seedlings results in the pronounced curvature of the apical hook. This effect, known as the "triple response", causes stem elongation inhibition, stem radial swelling, and absence of normal geotropic response (Guzman and Ecker, 1990). FIG. 4B shows the lower sensibility to ethephon in transgenic lines a1 and b1 compared to the non-transgenic line, indicating differences in the timing of ethephon sensing in soybean. In addition, seedlings of the transgenic lines exposed to different Ethephon concentrations showed hypocotyl hook formation at higher concentrations than the non-transgenic line. At the same time, first symptoms of hook formation for transgenic lines were observed at 25 µM Ethephon concentration while a concentration of 10 µM was sufficient for hook formation in the non-transgenic control. In the same way, transgenic lines showed a 17% (b1 line) and a 9% (a1 line) of seedlings with hook formation at concentration of 25 µM ethephon, while in the non-transgenic control almost 50% of the seedlings presented hook formation as this concentration (FIG. 4D).

Therefore, the lower ethylene sensitivity of soybean transgenic events compared to the non-transgenic control is demonstrated by the maintenance of chlorophyll levels and the observation of higher hypocotyls without hook formation under Ethephon and darkness treatments.

Independent HaHB4 Transgenic Events Performance Under Rainfed Field Conditions

Figure 5:
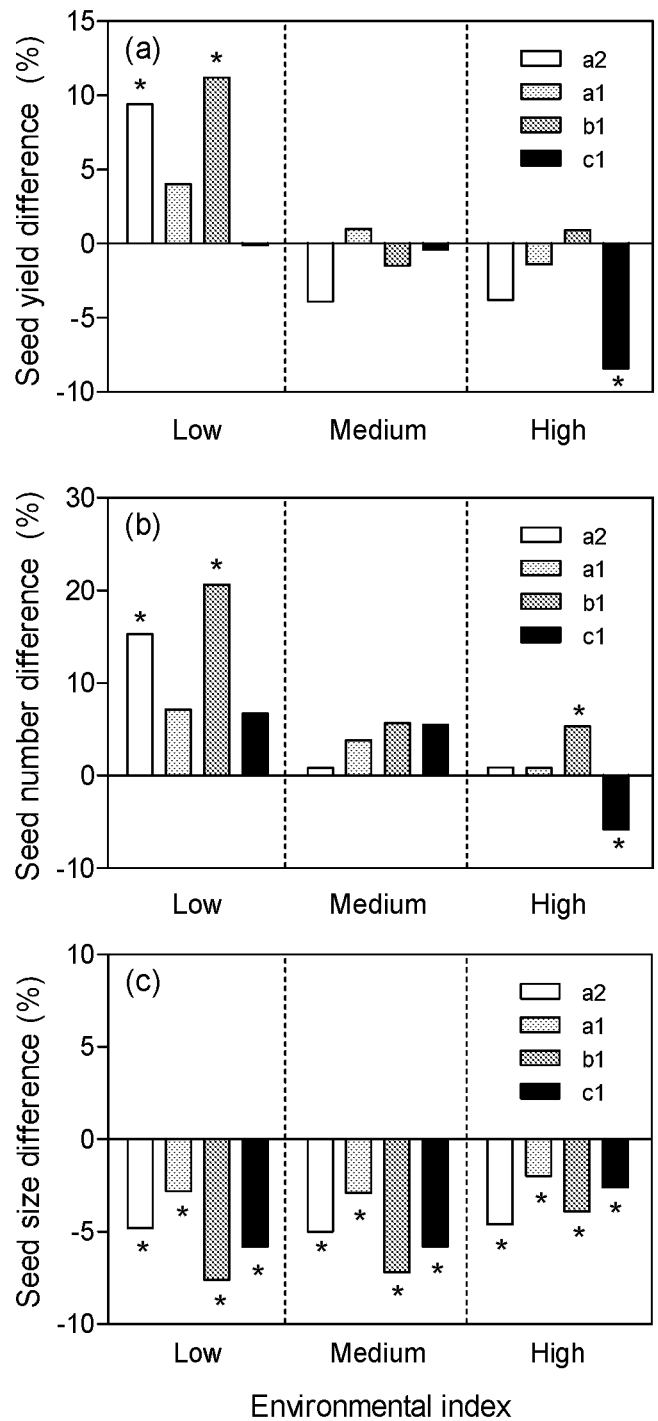
FIG. 5. Yield and yield components differences across environmental index for 4 independent transgenic events. Seed yield (a), seed number (b) and seed size (c) differences (%) between transgenic events and the non-transgenic control at low (L<2500 kg ha-1), medium (M=2500-3500 kg ha-1) and high (H>3500 kg ha-1) yield environments. Stars indicate statistically significant differences at $p<0.05$ for the mean values.

Four independent transgenic events were initially evaluated under field conditions in 12 trials during the 2012-2013 growing season. The trials were grouped as low, medium and high yield environments based on the non-transgenic control yield. All transgenic events showed lower 100-seed weight than the non-transgenic control (genotype main effect: p<0.0001). On the other hand, seed number per square meter and seed yield showed a significant genotype-environment interaction (p=0.013 for seed yield and p=0.033 for seed number). Seed yield of the a2 and b1 events was significantly higher than the control in the low yield environment (FIG. 5A). Seed yield was 9.4% for a2 and 11.2% for b1 higher than the non-transgenic control. These performance differences at the low yield environment were a consequence of a significant increase in seed number lesser than proportional reduction in seed weight. The a2 transgenic event showed a 15.3% increase in seed number (FIG. 5B) and a −4.8% decrease in seed weight (FIG. 5C) whereas the transgenic event b1 showed a 20.6% increase in seed number (FIG. 5B) and a −7.6% decrease in seed weight (FIG. 5C). For the medium and high yield environments, there was no difference in seed yield for any of the events except c1. Transgenic event c1 showed a significant seed yield reduction (−8.4%) (FIG. 5A) explained by significant reductions in seed number (−5.8%) (FIG. 5B) and seed weight (−2.6%) (FIG. 5C). Based on the better performance of the b1 event in the low yield environment and the absence of seed yield penalty in the high yield environment, the b1 event was selected for further field testing.

Further evaluation of the selected transgenic event b1 in an expanded set of environments during the 2013-14 growing season showed consistent results compared to the previous year. A combined analysis of the b1 event and the non-transgenic control for both growing seasons showed statistically significant genotype-environment interaction for seed yield (p=0.048) and seed number (p=0.050), whereas seed weight showed a significant genotype main effect (p<0.0001). Seed yield was significantly different between the two genotypes at the low yield environment (FIG. 6A). Seed number increase (23.3%) was proportionally higher than the seed weight decrease (−6.7%) resulting in significant seed yield increase (14.9%) (FIG. 6A, B, C). For medium and high yield environments, there was a compensation between seed weight and seed number. Seed weight decreases (−6.8% and −4.2% for medium and high yield environments, respectively) (FIG. 6C) were of similar magnitude that seed number increases (7.3% and 6.2% for medium and high yield environments, respectively) (FIG. 6B).

Classification and Identification of Differentially Expressed Genes

In order to evaluate the changes to transcriptional level conferring drought tolerance in the soybean transgenic b1 event, RNA-Seq transcriptomic analysis, using Illumina technology, was conducted in the b1 event and in the non-transgenic control (Williams 82). A first approach comparing irrigated vs. drought treatments identified 1931 differentially expressed (DE) genes (FC>=+/−2) in HaHB4 genotype. A similar number of DE genes were found for the wild type genotype, with 2215 DE genes (FC>=+/−2) in response to water stress. 866 DE genes were shared between the two genotypes (FIG. 7B). A second approach, comparing genotypes within treatments was conducted to identify DE genes associated to the HaHB4 transgene. As expected, due to the inducible character of the HaHB4 promoter, only 298 DE genes (FC>=+/−2) were observed when transgenic and non-transgenic plants were compared in irrigated plants.

Figure 7:
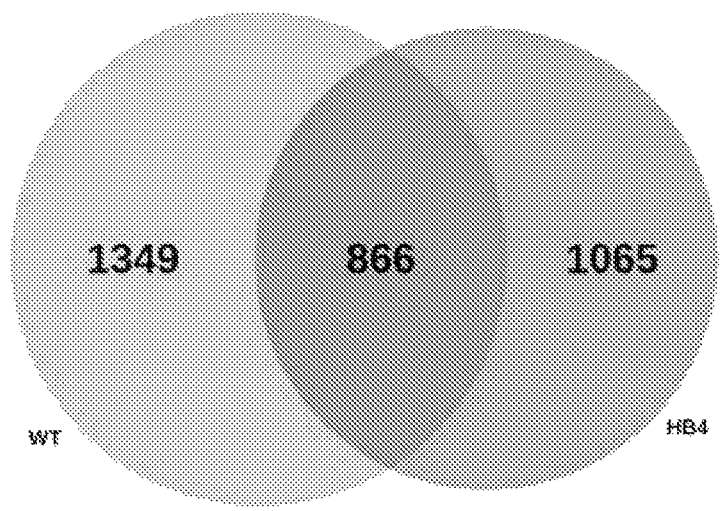
Figure 8:
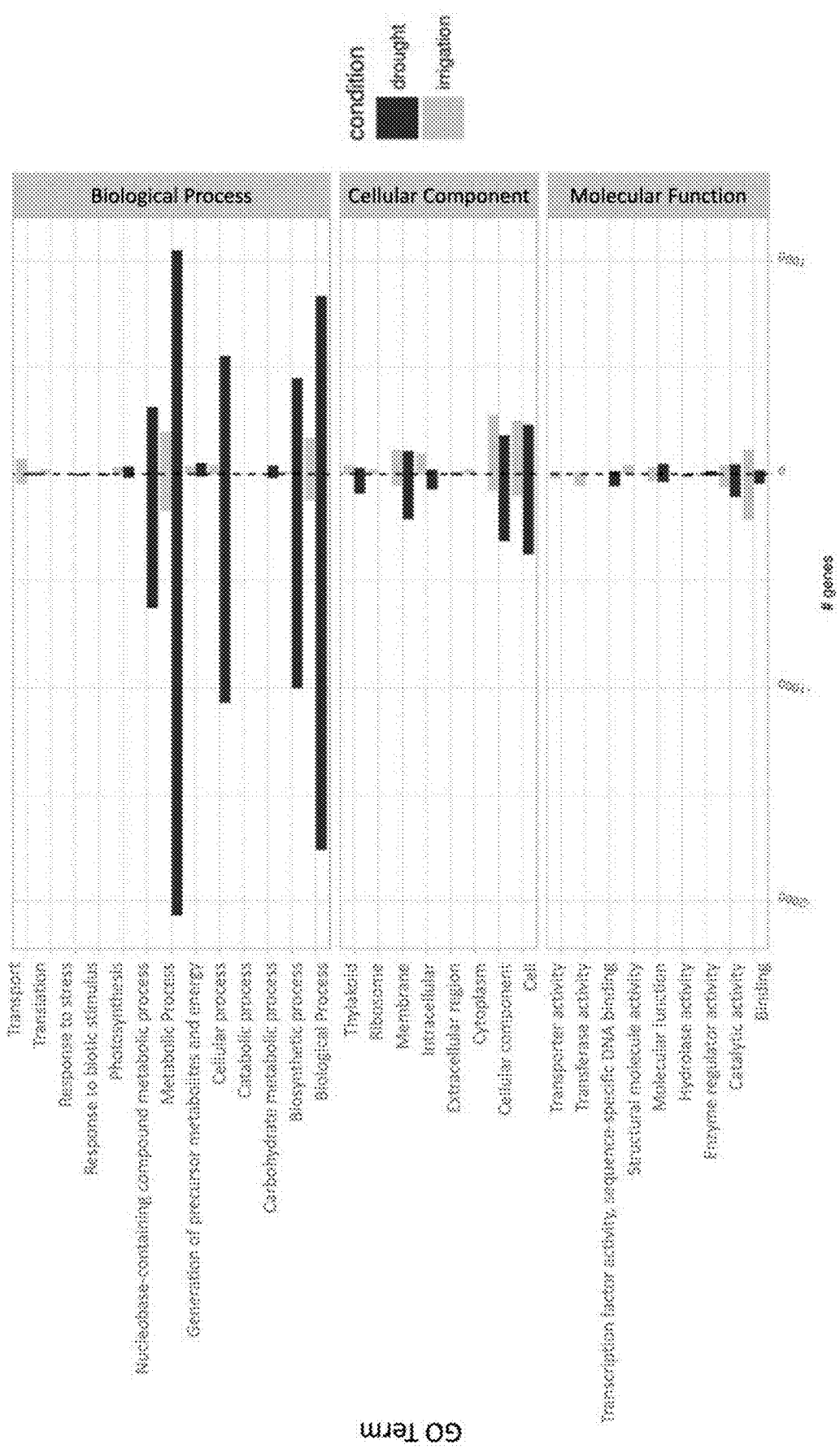
FIG. 8. Comparison of GO enrichment in DE genes. The results are summarized in biological process, cellular component and molecular function. The y-axis indicates the gene ontology categories; the x-axis indicates the number of DE genes.

The enriched Gene Ontology (GO) annotation comparing genotypes under irrigated conditions identified 941 GO terms associated to DE genes in the biological processes category, while 9931 GO terms in DE genes were identified under drought treatment (FIG. 7). In addition, the largest proportion of DE genes under water stress corresponds to metabolic and biological processes while cellular and biosynthetic processes also showed a considerable number of DE genes between genotypes (FIG. 8). Within the biological processes main group, DE genes under water stress were mostly involved in photosynthesis, plant defense response, transcription factors, and signal transduction (Table 2). Within the mentioned category, a second selection of DE genes was conducted based on fold change values. Values of either FC<=−2 (down regulated) or FC>=2 (up regulated) were selected for further identification and analysis.

A total of 12 photosynthesis-related genes were down regulated, with 9 of them exclusively associated to photosystem II (PSII) reaction center proteins, specifically down-regulation of genes encoding for Photosystem II reaction center proteins A, B, C, D, E and M was detected (Tikkanen et al., 2014). Regarding genes involved in plant defense response to stresses, lipoxygenase 1 (LOX1), lipoxygenase 2 (LOX2) and beta-1,3-glucanase 1 genes were up regulated when comparing transgenic and non-transgenic plants under water stress conditions. In addition, a set of genes involved in water transport were also DE. In that sense, three Aquaporin-like superfamily proteins were considerably repressed in the transgenic plants (Johansson et al., 2000; Sade and Moshelion, 2017).

Soybean transcription factors (Wang et al., 2010) differentially expressed between transgenic and non-transgenic genotypes under drought, involved genes playing important roles both in developmental processes and in response to environmental stresses, were observed (Table 2). In that sense, some members of the K-box region and MADS-box (Shu et al., 2013), Squamosa promoter-binding protein-like (Tripathi et al., 2017), basic helix-loop-helix (Hudson and Hudson, 2015) and Myb like transcription factors (Du et al., 2012) were downregulated while others were upregulated when comparing genotypes under water stress. On the other hand, salt tolerance zinc finger (Yuan et al., 2018), WRKY DNA-binding protein (Yin et al., 2013; Yang et al., 2017), basic leucine-zipper (Zhanq et al., 2018) and, the *Arabidopsis* homologous of GBF's pro-rich region-interacting factor 1 (Tokumaru et al., 2017) and the Integrase-type DNA-binding superfamily proteins (Licausi et al., 2010; Yan, 2014), were upregulated.

Finally, genes coding for proteins involved in signal transduction (Ahanger et al., 2018), showed changes when comparing genotypes under water stress conditions. Particularly, these genes are Calcium-binding EF-hand family, phosphatase and kinase proteins, whose expression was considerable higher in HaHB4 compared to control genotype under water stress (Table 2).

TABLE 2

Fold change (fc) value of a selection of differentially expressed genes between transgenic and non-transgenic genotypes under water stress.

| Gene ID | Gene Annotation | log2 (Fc) | p-val |
|---|---|---|---|
| Glyma.09G160500 | Aquaporin-like superfamily protein | −6.3460 | 0.0120505 |
| Glyma.10G174400 | Aquaporin-like superfamily protein | −6.0696 | 0.0114654 |
| Glyma.16G210000 | Aquaporin-like superfamily protein | −5.8523 | 0.0010792 |
| Glyma.01G058600 | photosynthetic electron transfer B | −5.3466 | 0.0010792 |
| Glyma.11G114700 | photosystem II reaction center protein C | −5.1418 | 0.0064869 |
| Glyma.06G269700 | thiazole biosynthetic enzyme, chloroplast (ARA6) (THI1) (THI4) | −4.4050 | 0.0010792 |
| Glyma.04G095000 | photosystem II reaction center protein D | −4.1302 | 0.0010792 |
| Glyma.11G162200 | photosystem II reaction center protein A | −4.1066 | 0.0010792 |
| Glyma.13G028200 | photosystem II reaction center protein A | −4.0988 | 0.0010792 |
| Glyma.06G217900 | photosystem II reaction center protein D | −3.8959 | 0.0010792 |
| Glyma.01G153500 | photosystem II reaction center protein D | −3.6724 | 0.0064869 |
| Glyma.12G232700 | photosystem II reaction center protein E | −3.6514 | 0.0281353 |
| Glyma.08G281300 | photosystem II reaction center protein B | −3.0341 | 0.0137509 |
| Glyma.05G074900 | photosystem II reaction center protein C | −2.6759 | 0.0010792 |
| Glyma.12G232900 | photosynthetic electron transfer A | −2.3801 | 0.0058037 |
| Glyma.08G189500 | lipoxygenase 1 | 2.1110 | 0.0180400 |
| Glyma.12G054700 | lipoxygenase 2 | 2.7721 | 0.0010792 |
| Glyma.03G132900 | beta-1,3-glucanase 1 | 2.2403 | 0.0010792 |
| Glyma.19G034500 | K-box region and MADS-box transcription factor family protein | −3.6906 | 0.0028364 |
| Glyma.04G197100 | Squamosa promoter-binding protein-like (SBP domain) transcription factor family protein | −3.2700 | 0.0356172 |
| Glyma.05G200900 | basic helix-loop-helix (bHLH) DNA-binding superfamily protein | −2.5748 | 0.0058037 |
| Glyma.07G074300 | Myb like DNA-binding domain | −2.4033 | 0.0175182 |
| Glyma.13G368500 | basic helix-loop-helix (bHLH) DNA-binding superfamily protein | −2.3053 | 0.0010792 |
| Glyma.12G226000 | squamosa promoter-binding protein-like 12 | −2.2374 | 0.0010792 |
| Glyma.17G156000 | basic helix-loop-helix (bHLH) DNA-binding superfamily protein | −2.0947 | 0.0422725 |
| Glyma.17G236200 | salt tolerance zinc finger | 2.0543 | 0.0010792 |
| Glyma.U025800 | squamosa promoter-binding protein-like 12 | 2.0921 | 0.0312612 |
| Glyma.20G153700 | K-box region and MADS-box transcription factor family protein | 2.2592 | 0.0043799 |
| Glyma.17G097900 | WRKY DNA-binding protein 72 | 2.3047 | 0.0338911 |
| Glyma.02G126100 | basic leucine-zipper 42 | 2.3690 | 0.0253887 |
| Glyma.17G099800 | myb domain protein 94 | 2.3812 | 0.0276823 |
| Glyma.15G063000 | basic helix-loop-helix (bHLH) DNA-binding superfamily protein | 2.5315 | 0.0058037 |
| Glyma.12G206600 | GBF\'s pro-rich region-interacting factor 1 | 2.7909 | 0.0010792 |
| Glyma.17G047300 | Integrase-type DNA-binding superfamily protein | 2.2879 | 0.0064869 |
| Glyma.09G072000 | Integrase-type DNA-binding superfamily protein | 2.5876 | 0.0010792 |
| Glyma.13G112400 | Integrase-type DNA-binding superfamily protein | 2.6309 | 0.0010792 |
| Glyma.15G180000 | Integrase-type DNA-binding superfamily protein | 3.2130 | 0.0078017 |
| Glyma.09G210900 | phosphoribulokinase | 2.0034 | 0.0281353 |
| Glyma.06G159400 | Small GTP-binding protein | 2.0098 | 0.0010792 |
| Glyma.12G227800 | sodium/calcium exchanger family protein/calcium-binding EF hand family protein | 2.0401 | 0.0010792 |
| Glyma.14G157700 | wall-associated kinase 2 | 2.0668 | 0.0294783 |
| Glyma.06G081800 | Protein kinase superfamily protein | 2.1118 | 0.0225366 |
| Glyma.13G296200 | Concanavalin A-like lectin protein kinase family protein | 2.1834 | 0.0096839 |
| Glyma.14G040200 | CBL-interacting protein kinase 3 | 2.1869 | 0.0258477 |
| Glyma.11G157100 | calmodulin-like 41 | 2.2133 | 0.0164572 |
| Glyma.03G001600 | HAD superfamily, subfamily IIIB acid phosphatase | 2.2990 | 0.0442716 |
| Glyma.02G044600 | protein kinase family protein | 2.4190 | 0.0285838 |
| Glyma.08G200100 | HAD superfamily, subfamily IIIB acid phosphatase | 5.7805 | 0.0010792 |
| Glyma.17G112000 | Calcium-binding EF-hand family protein | inf. | 0.0010792 |

Groups of genes correspond, from top to bottom, to (A) aquaporin-related genes, (B) photosynthesis related genes, (C) plant defense response genes, (D) transcriptior factors and (D) signal transduction.

Figure 6:
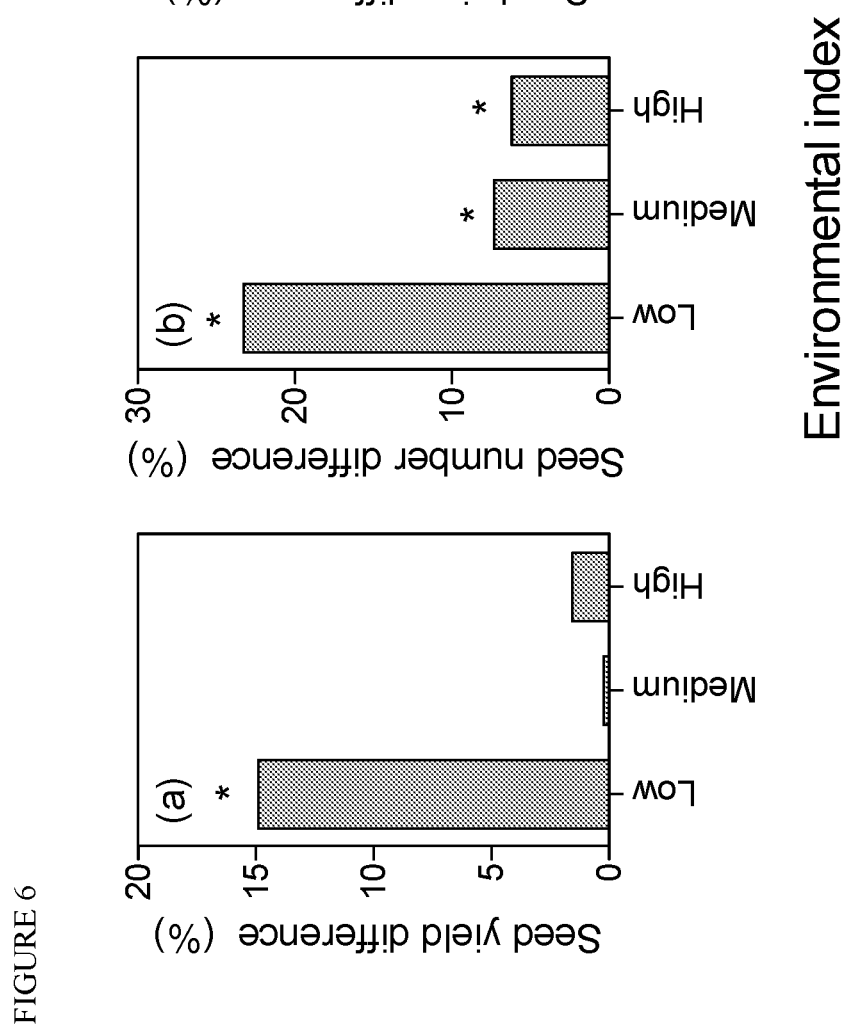
FIG. 6. Yield and yield components differences across environmental index for the selected event (b1). Seed yield (a), seed number (b) and seed size (c) differences (%) between b1 transgenic event and the non-transgenic control for al low (L<2500 kg ha-1), medium (M=2500-3500 kg ha-1) and high (H>3500 kg ha-1) yield environments. Stars indicate statistically significant differences at $p<0.05$ for the mean values FIG. 7. Venn diagram of differentially expressed genes. A—Number of differentially expressed genes between water stressed and well-watered treatments for the b1 transgenic event and the non-transgenic control genotype.

Differences between efficacy of the transgenic events in the low yield environment and the existence of yield penalty in the high yield environment suggest that the promoter type (inducible or constitutive) and HaHB4 expression level contribute to the final response to environmental conditions and performance. Our results in the selected transgenic event b1 with inducible promoter showed that the physiological responses induced by HaHB4 could be translated into higher yield in low yield environments with no yield penalty in high yield ones (FIG. 6).

Example 3: Soybean Event IND-ØØ41Ø-5 DNA Sequences Characterization

Soybean event IND-ØØ41Ø-5 inserted in genomic DNA of the plant was characterized, as well as flanking genomic sequences, through molecular techniques.

To this end, sequencing of DNA of event IND-ØØ41Ø-5 was performed, the number of transgenic inserts was determined (number of integration sites within soybean genome), also the integrity and stability of the sequence over six generations were determined.

Besides, next generation sequencing (NGS) technology was used in parallel with conventional technologies to describe the event IND-ØØ41Ø-5. NGS was used to determine: the whole-genome sequence of IND-ØØ41Ø-5; this includes the T-DNA sequence; and the junction sequences (JS) between the T-DNA and the native soybean genome. The flanking sequences allowed further monitoring of the stability and the integrity of the T-DNA insertion across six self-fertilized generations, as well as in plants resulting from out crossing with another soybean variety.

DNA was isolated from leaf tissues of homozygous plants for the event IND-ØØ41Ø-5 (from greenhouse or field grown) or from soybeans plants Williams-82 variety for Southern blot analysis. For whole-genome sequencing and segregation analysis in F2 plants, DNA was extracted from embryonic tissue.

A commercially available soybean cultivar, Bio 6.5 (Bioceres Semillas S. A., Ocampo 210 bis, Rosario, Argentina), was used for crossing of plants carrying the event IND-ØØ41Ø-5.

In general, prior to extraction, leaf tissue frozen in liquid nitrogen was processed to a fine powder in a mortar with a pestle or in tubes in a "96 mill" for minipreps.

The following techniques were used to extract plant DNA, depending on the amounts of DNA needed for experimental purposes:

CTAB Method (hexadecyltrimethylammonium bromide or cetyltrimethylammonium bromide):

Said method was used to extract genomic DNA from plant samples (Variabilidad genotípica de aislados de *Phytophthora capsici* en Guanajuato," Guerrero-Aguilar et al. May 2, 2022, *Mexican Journal of Agricultural Sciences*, Vol. 13, No. 1 Texcoco). 600 µl of CTAB buffer (2% w/v CTAB, 100 mM Tris HCl, 20 mM EDTA, 1.4 M NaCl, and (3-mercaptoethanol) and 5 µg RNaseA were added to approximately 100 mg of ground leaf tissue and homogenate was incubated at 55-60° C. for 15-20 minutes with intermittent mixing. 600 µL of chloroform was added to the samples and mixed by hand for 2-3 minutes, then centrifuged at 10,000 rpm for 8 minutes. The upper aqueous phase was placed into a clean microtube and the DNA was precipitated with 400 µL of isopropanol. The sample was centrifuged at 12,500 rpm for 10 minutes to pellet the precipitated DNA. The DNA pellets were washed with 300 µl of 70% ethanol by centrifuging the samples at 12,500 rpm (5 minutes). The DNA pellets were air-dried, then resuspended in 100 µl of TE buffer (10 mM Tris HCl, 1 mM EDTA, pH 8.0). All extracted DNA was stored in a 4° C. refrigerator or a −20° C. freezer.

Kit DNeasy Plant Maxi by Qiagen (Valencia, CA) for large preparations (Southern blot analyses) or QIAprep® Miniprep (Qiagen Inc.) for small preparations.

DNA isolated from embryonic tissue was used por Illumina-based sequencing, and for segregations studies of F2 progeny from IND-ØØ41Ø-5 crosses and Bio 6.5. Prior to the extraction, seeds carrying the event IND-ØØ41Ø-5, Williams 82 and F2 were incubated in water at 37° C. to facilitate the disruption of the seeds. The embryonic tissues were then separated from the cotyledons and their DNA extracted following the CTAB method. The DNA was quantified either using a Quant-iT™ PicoGreen® (Invitrogen, Carlsbad, CA) or by QuBit fluorometer (Invitrogen) and the Quant-iT™ dsDNA BR Assay Kit (Invitrogen). Then, the DNA was stored at 4° C. or at −20° C.

The DNA was sawed on 0.8% (w/v) agarose gels to assess the integrity of the samples. The gel was prepared with TAE 1× buffer (40 mM Tris, 20 mM acetic acid and 1 mM EDTA) and run at 120 v. DNA samples were diluted in loading buffer 6× (Glycerol 30% and bromophenol blue) and Gel-Red™ Nucleic Acid Gel Stain 200× (Biotium, Inc., Hayward, CA).

Agarose gels of 1.5% (w/v) were used for resolving amplicons with lengths between 200 bp to 1500 bp, while 1% (w/v) agarose gels were used for larger DNA fragments. The electrophoresis was performed in TAE 1× buffer and run at 120 v. The samples were processed as described above. Molecular Weight Markers 100 bp (from 100 to 2080 bp) and/or Lambda BstII (from 117 bp to 14140 bp) (P-BL, Argentina) were selected according to the amplicon size to be resolved.

The standard PCR reactions performed in most of the studies were conducted using 100 ng of genomic DNA template in a 40 µl reaction volume with final concentrations of: 1.8 mM $MgCl_2$, 2 mM DMSO, 0.4 µM of each primer, 50 µM of each dNTP and 1 U of FastStart High Fidelity (Roche, Indianapolis, IN). The following cycling program was applied for amplicons with intended sizes comprised between 400 bp and 700 bp:

1 cycle at 95° C. for 30 seconds;
35 cycles at 95° C. for 30 seconds, 55° C. for 30 seconds, 72° C. for 30 seconds;
final extension: 1 cycle at 72° C. for 10 minutes.

For the generation of amplicons with sizes of 1100 bp to 1300 bp the duration of the extension step at 72° C. was increased from 30 seconds to 60 seconds.

In the case of the whole insert amplification with the Expand Long Range polymerase, final concentrations of 2.5 mM $MgCl_2$, 6% DMSO, 0.3 µM of each primer, 500 µM of each dNTP, and 3.5 U of Expand Long Range (Roche, Indianapolis, IN) were used. The amplification was performed under the following conditions:

1 cycle at 92° C. for 2 minutes;
10 cycles at 92° C. for 10 seconds, 55° C. for 15 seconds, 68° C. for 10 minutes;
25 cycles at 92° C. for 10 seconds, 55° C. for 15 seconds, 68° C. for 10 minutes increasing the time of this final step for 20 seconds for each cycle;
1 cycle at 68° C. for 7 minutes.

Amplicons for determining the sequence of the T-DNA insertion were produced using Phusion® High-Fidelity DNA Polymerase from New England BioLabs (Ipswich, MA).

All sequenced PCR products were resolved by agarose gel electrophoresis as described above and further purified using Illustra GFX PCR DNA and Gel Band Purification Kit (GE, Piscataway, NJ).

Amplicons were cloned (TOPO TA Cloning® kit by Invitrogen) for determination of the T-DNA sequence by Sanger method.

TABLE 3

The list of primers used to determine insert sequence in the event IND-ØØ41Ø-5 through Sanger conventional sequencing method.

| Primer name | SEQ ID NO: | Primer sequence 5'-3' |
|---|---|---|
| 750 | 5 | ACGCAACTGAACTCAGACCA |
| 751 | 6 | AAGTGGCGATATGGTTCCAG |

TABLE 3-continued

The list of primers used to determine insert sequence in the event IND-ØØ41Ø-5 through Sanger conventional sequencing method.

| Primer name | SEQ ID NO: | Primer sequence 5'-3' |
|---|---|---|
| 752 | 7 | GGCTGCAAGTTTTGGTCAAT |
| 753 | 8 | TTCGGCTACATTTCTCAGCA |
| 754 | 9 | AGCCAATGAATCCTCACCAG |
| 755 | 10 | ATTAGGCGAGTAGGCAGCAA |
| 756 | 11 | CAACACACCTACAAACGTGTCA |
| 757 | 12 | GGGTGGGGGCTACTACTTTT |
| 758 | 13 | CTTCAGCAGGTGGGTGTAGAG |
| 759 | 14 | AGTCGACCGTGTACGTCTCC |
| 760 | 15 | GTTGGGTCAGCCTGAGTGAT |

Clones were then purified following the QIAprep Spin Miniprep Kit by Qiagen (Valencia, CA). Plasmid DNA was sent for sequencing to Davis Sequencing (Davis, CA). Sequences were analyzed using the software SeqMan Pro from DNASTAR (Madison, WI). At least three clones were sequenced for each amplicon.

a) Southern Blot Analysis

Figure 9:
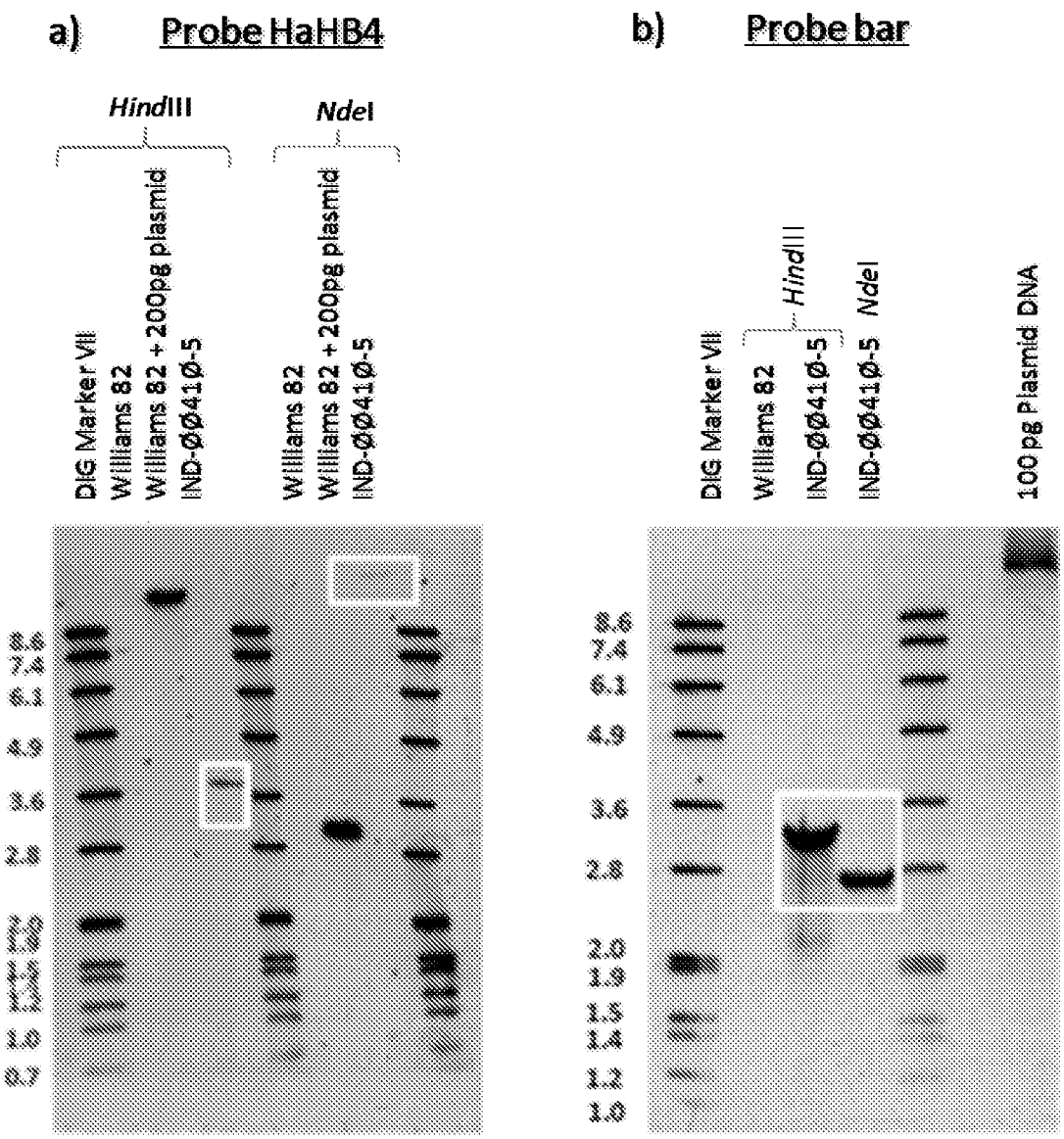
FIG. 9. Southern blots of T5 IND-ØØ41Ø-5 plant DNA digested with HindIII and NdeI. Blots were hybridized with DIG-labeled probes for a) HaHB4 and b) bar detection, respectively. DNA bands in IND-ØØ41Ø-5 digests hybridizing to indicated probes are highlighted in white boxes. Williams 82+200 pg plasmid DNA and 100 pg plasmid DNA were used as positive controls. DIG-labeled Marker VII ladder band sizes are indicated on the left of the blots in kb.

The number of T-DNA inserts was determined in homozygous T5 IND-ØØ41Ø-5 plants by Southern blot analysis. The DNA from this event was digested with two enzymes: HindIII and NdeI. There were two sites for HindIII in the T-DNA, located near each other (FIGS. 1A and 1B). Assuming the occurrence of a single, intact T-DNA in the genome of IND-ØØ41Ø-5, the minimum fragment size detected by hybridization of the HaHB34 probe would be 1.85 kb. The probe for the selectable bar gene, on the other hand, would detect digests extending over the left border into the soybean genome. These fragments should be longer than 2.6 kb (FIG. 1B). In the Southern blot presented in FIG. 9, the highlighted fragments have the expected sizes and were consistent with a single T-DNA insert.

There are four NdeI restriction sites in the construct (FIG. 1Aa), two within the T-DNA and two in the binary vector. Complete NdeI digestion in the T-DNA should release a DNA segment precisely 2703 bp long that contains the binding target for the bar probe. The HaHB4 probe was expected to detect a DNA fragment of a minimum size of 1.35 kb, assuming a single, intact T-DNA. The hybridizing band in the NdeI digest was longer than 8.6 kb (FIG. 9A), which is consistent with the presence of a single, intact T-DNA insert.

One gram of leaf tissue from either IND-ØØ41Ø-5 or Williams 82 was flash frozen using liquid nitrogen and ground into fine powder using a pre-chilled pestle and mortar. DNA was extracted with Qiagen DNeasy Maxi Prep Kit following manufacturer's protocol. After elution, the DNA was precipitated by adding 1/10 volume of 3M sodium acetate and 2-3 volumes of 100% ethanol. The pellet was washed with 70% ethanol and suspended in 80 μl of 1×TE buffer. The DNA was quantified using a QuBit fluorometer. The concentration of DNA for IND-ØØ41Ø-5 was 1120 ng/μl and that of Williams 82 was 800 ng/μl.

To obtain the fragments digested with restriction enzymes, for each 50 μl digestion reaction, 5 μg genomic DNA was mixed with either Hind/l enzyme or NdeI enzyme at concentrations of 10 U/μg of DNA. The samples were digested overnight (~16 hours) at 37° C. For digests of the plasmid control, 100-200 picograms of plasmid DNA were used.

The digested fragments of IND-ØØ41Ø-5 and Williams 82 genomic DNA were loaded into a 0.7% agarose gel along with DIG labeled Molecular Weight Marker VII (Roche Cat No. 1669940910). The samples were run at 50 V overnight. The gel was incubated in denaturing buffer twice for 30 minutes each time. The denatured gel was washed in transfer buffer for 15 minutes prior to alkaline transfer.

Molecular probes for HaHB4 and bar genes (Table 4) were synthesized following the procedure outlined in the Roche PCR DIG Probe Synthesis Kit (Cat. No. 11636090910).

TABLE 4

List of primers used for the preparation of the probes used in Southern blot analyses.

| Probe | Size (pb) | Location on vector | Hybridization (° C.) | Primer type | Primer Number | Sequence |
|---|---|---|---|---|---|---|
| HB4 | 226 | 10159 . . . 10510 | 45 | Forward | 2527 (SEQ ID NO: 16) | CGCTTGCGTCTAAATCCGAGTCTC |
| | | | | Reverse | 203 (SEQ ID NO: 17) | CAAGACCGGCAACAGGATTC |
| Bar | 448 | 7267 . . . 7714 | 55 | Forward | 378 (SEQ ID NO: 18) | ATATGGCGCTGATCTCTGCT |
| | | | | Reverse | 1970 (SEQ ID NO: 19) | GGCGGTCTGCACCATCGTCA |
| STA | 357 | 1229 . . . 1585 | 54 | Forward | 1747 (SEQ ID NO: 20) | AAGACGACCATCGCAACCCATCTA |
| | | | | Reverse | 1748 (SEQ ID NO: 21) | TAGCCTTCCATCCGTGACCTCAAT |

TABLE 4-continued

List of primers used for the preparation
of the probes used in Southern blot analyses.

| Probe | Size (pb) | Location on vector | Hybridization (° C.) | Primer type | Primer Number | Sequence |
|---|---|---|---|---|---|---|
| REP | 258 | 2979 . . . 3236 | 50 | Forward | 1745 (SEQ ID NO: 22) | AGCTGATTGGATGTACCGCGAGAT |
|  |  |  |  | Reverse | 1746 (SEQ ID NO: 23) | TTCAAATCGTACTCCGGCAGGTCA |
| aadA | 229 | 5935 . . . 6163 | 50 | Forward | 822 (SEQ ID NO: 24) | ATCAAACATCGACCCACGGCGTAA |
|  |  |  |  | Reverse | 1127 (SEQ ID NO: 25) | GATCAATTCGGGCACGAACCCAGT |

Alkaline transfer of DNA from the agarose gel was performed using Turboblotter-Rapid downward transfer system (Whatman). The DNA was transferred to a 12×21 cm Nylon membrane (Nytran™ SuPerCharge, Sigma-Aldrich Co., St. Louis, MO) for 4 hours. The membrane was washed in neutralizing buffer (0.2M sodium phosphate, pH6.8). The DNA was permanently cross-linked to the membrane by Ultraviolet Gross linker (CL-1000) with 2 exposures of 1500 mJ.

The membrane was incubated in 50 ml of Roche DIG EasyHyb hybridization buffer (Cat. no. 11 603 558 001) at pre-calculated hybridization temperatures (45° C., 55° C. for bar gene and HaHB4 gene probes respectively) on an orbital shaker.

Aliquots of 35 µl and 45 µl bar and HaHB4 probes, were diluted by adding 65 and 55 µl, respectively, of 1×TE buffer. The probe solutions were incubated at 95° C. for 10 min and cooled to 4° C. for 2 min. They were added to 8.75 ml of DIG hybridization buffer and poured to the bottom of the hybridization bottle. The membranes were incubated at the described hybridization temperatures for 16 hours in a hybridization oven (VWR scientific products) with an orbital shaker.

After hybridization, the membranes were washed with washing buffer according to instructions provided with the Roche, DIG Luminescent Detection Kit. After 1 hour blocking with 1× blocking reagent, the membrane were incubated for 30 min in a solution containing 50 ml of 1× blocking reagent and 5 µl of anti-digoxigenin-AP. The membrane was washed twice with washing buffer for 30 minutes each time and finally treated with detection buffer for 5 minutes. At this point the membrane was placed in a KPL Hybridization Bag (KPL Cat. No. 60-00-51). 5 ml of CSPD solution from the DIG Luminescent Detection Kit was applied evenly across the membrane. The membrane was incubated with CSPD solution for 5 minutes at room temperature. The hybridization bag with the membrane was heat sealed and incubated at 37° C. for 15 minutes. The hybridization bag was placed in a cassette with Kodak Biomax Light Film (Cat. No. 178 8207) in dark room and exposed for 20 minutes. The films were developed at dark using a Konika QX-60A X-ray film processor. Subsequent exposures were made at 1 hour or 2 hours as required.

b) Junction Sequence Analysis (JSA) and of T-DNA Sequence of Event IND-ØØ41Ø-5

The Junction Sequence Analysis (JSA) of IND-ØØ41Ø-5 using the Illumina-generated sequence data was consistent with the integration or a single copy of the insert at a single locus. This result was supported by the finding of only two junction sequences in the sequenced whole-genome containing event IND-ØØ41Ø-5. The Junction Sequences (JS) were named after the chromosome in which the T-DNA is integrated. The positions in the soybean genome according to SoyBase data are JS-9L-32743826 and JS-9R-32743683. JSA are presented in FIG. 10.

The complete sequence of the T-DNA insert and its flanking soybean sequences (SEQ ID NO: 1) were assembled de novo from the Illumina-generated DNA sequence reads.

It was verified that the sequence of the T-DNA insert in event IND-ØØ41Ø-5 was identical to the sequence of T-DNA in the binary plasmid, with a single copy of each gene and each regulatory element, except for the almost complete lack of RB (FIG. 11B). Conventional Sanger sequencing of multiple amplicons covering the whole insertion and its flanking sequences corroborated the JSA analysis of the Illumina-generated sequence. In addition, it was possible to generate a single amplicon of 4710 bp, using Expand Long Range PCR, with a set of primers complementary to the flanking sequences. The amplicons obtained using IND-ØØ41Ø-5 or Williams 82 DNA as templates were of the expected sizes and the DNA sequence of this IND-ØØ41Ø-5 amplicon was identical to the T-DNA sequence derived from whole-genome sequencing.

c) Localization of IND-ØØ41Ø-5 T-DNA in the Soybean Genome.

Figure 11:
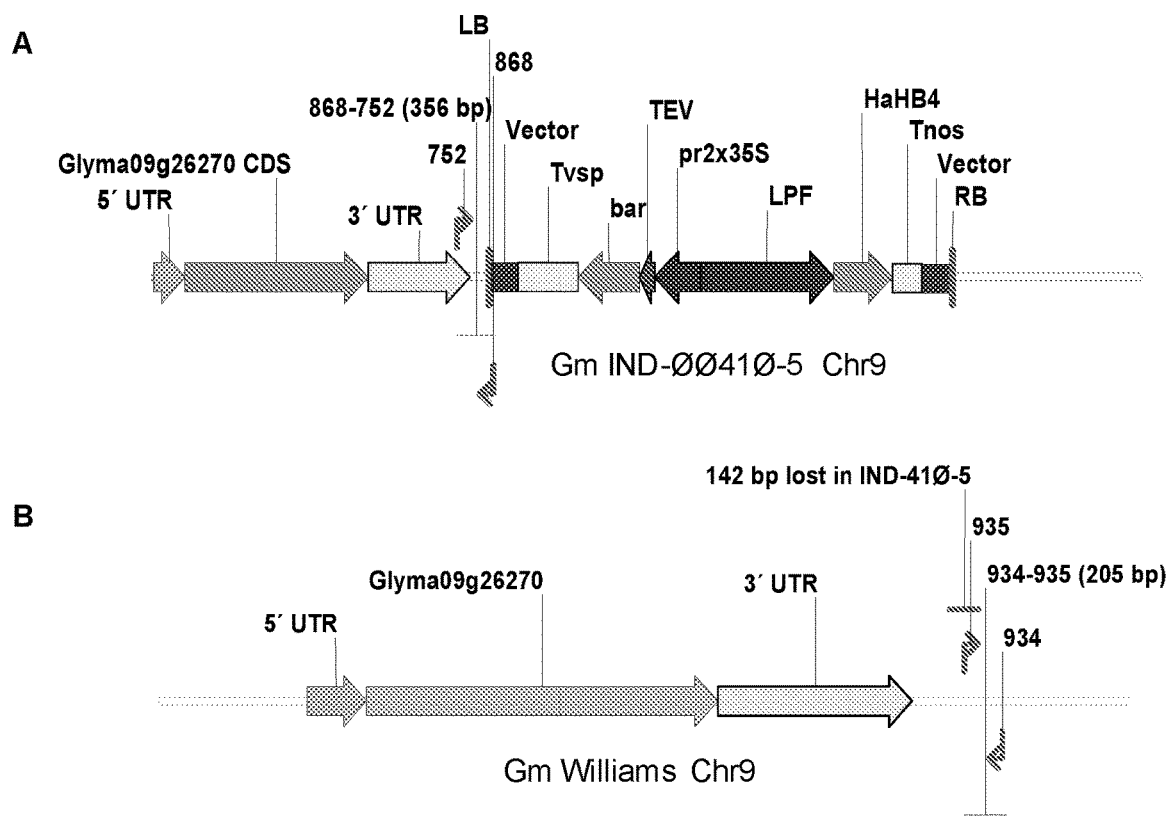
FIG. 11. Schematic representation of IND-ØØ41Ø-5 insertion locus and native allele. A) Scheme of the insertion in IND-ØØ41Ø-5 showing the elements present in T-DNA and primers used for analysis of segregation in F2 plants. The labeled primers 868 and 752 were used to assay for the presence of the Left Border Junction. B) Scheme of native allele showing the elements present in insertion region (without the T-DNA) and primers used for PCR test of segregation in F2 plants. Primers 934 and 935 were used to assay for the presence of the native allele. Gm: *Glycine max*, Chr9: chromosome 9, UTR: untranslated region, CDS: coding sequence.

The flanking sequences were mapped to the soybean genome by homology search using BLASTN (Altschul et al. 1990). The insertion of the T-DNA occurred in a single location of chromosome 9. The insertion was located 752 bp downstream of the last exon (Exon number 5) of F-box At1g60400-like putative gene (corresponding to Glyma.09g142000 in the reference genome (Williams 82), formerly known as Glyma09g26270), and 405,138 bp upstream of the nearest confirmed gene, an ATL6-like E3 ubiquitin ligase. It should be noted that a 142 bp fragment of the soybean chromosome was lost at the T-DNA insertion site. The insertion did not disrupt any genes or any other known annotated feature in the soybean genome (FIG. 11).

d) Absence of Transgenic Binary Plasmid Elements:

In principle, *Agrobacterium* should only transfer into the host cells its T-DNA the portion of the plasmid contained between the left border (LB) and right border (RB) sequences. However, it has been reported that *Agrobacterium* can also transfer a portion of the binary plasmid, not corresponding to the T-DNA, or even the whole of it (De Buck et al. 2000). Assays for the presence of said unintended DNA in the IND-ØØ41Ø-5 soybean genome were negative.

The whole genome was sequenced using Illumina NGS technology to determine unequivocally the absence of remains of sequences of the plasmid in event IND-ØØ41Ø-5. Additionally, Southern blot assays were performed to provide a second assay to prove the absence of remains of vector sequences. None of the probes specific for plasmid sequences foreign to the T-DNA (aadA, STA, and REP) hybridized to the genomic DNA of IND-ØØ41Ø-5.

e) Insertion Locus Stability in IND-ØØ41Ø-5 and T-DNA Integrity:

The position of the IND-ØØ41Ø-5 T-DNA across six generations was monitored. A set of PCR primer pairs was selected to provide overlapping amplicons across the insertion locus of the IND-ØØ41Ø-5 T-DNA, inclusive of the soybean chromosome 9 flanking sequences. Sequences of the contigs assembled from these overlapping PCR products suggested that the T-DNA was intact and stable. The organization of the genetic elements in the IND-ØØ41Ø-5 soybean event was the same as the one present in the binary plasmid T-DNA used in transformation to obtain this transgenic line. No changes in DNA sequence were detected across six tested generations.

f) T-DNA Segregation Over Sexual Transfer:

Segregation of the T-DNA was assessed in F2 progeny plants from crosses between IND-ØØ41Ø-5 and a commercial soybean cultivar (Bio 6.5) using PCR. A set of PCR reactions, diagnostic of the T-DNA junction at the Left Border and of the native soybean allele, clearly showed that the T-DNA segregated as a single locus.

A homozygous IND-ØØ41Ø-5 transgenic plant was crossed with Bio 6.5 to produce the F1 progeny. Four F1 plants were self-pollinated to produce F2 seeds that were used for the segregation analysis. The DNA isolation and the corresponding experiments were conducted using 73 F2 seeds. F2 plants were scored as homozygous for the IND-ØØ41Ø-5 T-DNA (I) when the amplicon for the Left Border Junction was present and the amplicon for the native allele was absent. F2 plants were scored as hemizygous (H) when both amplicons described above were present. F2 plants were scored as homozygous for the native Williams 82 cultivar allele when the amplicon for the Left Border Junction was absent and the amplicon for the native allele was present (W).

These results support the conclusion that the IND-ØØ41Ø-5 T-DNA resides at a single locus within the soybean genome and is inherited according to Mendelian inheritance principles.

The selected transgenic event IND-ØØ41Ø-5 differs from the parental Williams 82 by a single T-DNA. This T-DNA carries a single copy of the selectable marker-gene bar and a single copy of the HaHB4 gene along with their regulatory sequences. The T-DNA was integrated in chromosome 9 between two native genes coding for an F-box At1g60400-like protein and an AtL6-like E3 ubiquitin ligase. The integration did not disrupt any known gene or annotated sequence but caused the loss of a 142 base pair sequence corresponding to an intergenic region. The locus of the insertion and the T-DNA structure were stable over six generations of self-pollination. The T-DNA insertion was shown to segregate in a Mendelian fashion. No sequences outside the T-DNA border were integrated into the IND-ØØ41Ø-5 event.

Example 4: Useful Methods for Identification of IND-ØØ41Ø-5 in a Sample

The following example describes the detection system event-specific useful to identify DNA of event IND-ØØ41Ø-5 in a soybean sample. This method is site-specific, therefore, only amplifies sequences of one of the insertion sites of event IND-ØØ41Ø-5.

Multiplex qPCR for HaHB4 and Le1 (reference soybean gene Lecithin 1) was performed using specific oligonucleotides and different fluorescent probes attached to FAM and HEX for HaHB4 and Le1, respectively. Multiplex qPCR technique was also used for RB of event IND-ØØ41Ø-5 and bar transgene using probes marked with FAM and HEX respectively. On the other hand, LB of the event was detected through end-point PCR, and qPCR was used for detection of the wild allele (WT) using a probe marked with HEX.

Figure 12:
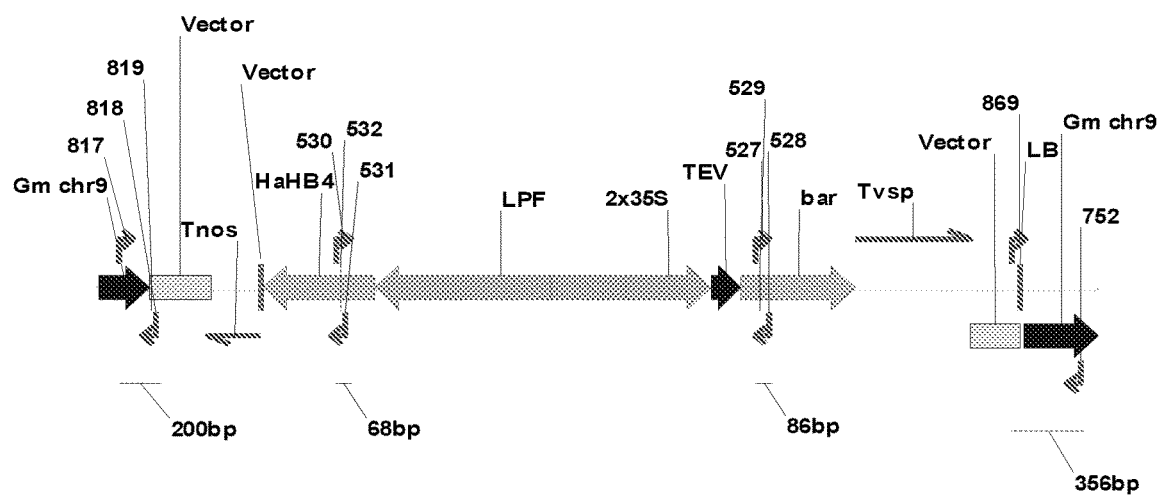
FIG. 12. Schematic representation of the insertion in IND-ØØ41Ø-5. The scheme shows 4 detection systems from different elements of the insert in the event IND-ØØ41Ø-5. Three of them correspond to TaqMan detection systems (HaHB4, bar and flank to RB) while one corresponds to an end-point PCR system (flank to LB).

FIG. 12 shows a scheme of the insertion in IND-ØØ41Ø-5 and of oligonucleotides positions and probes used for detection of different elements of the construct.

Detection of Insertion Site Towards RB

Great part of RB (T-DNA right border) was lost during the insertion process; there are only 3 pb left. It is mentioned with the purpose of being aware of the insert with respect to the original construct.

The oligonucleotides 817 (SEQ ID NO:) and 818 (SEQ ID NO:) amplify a 200 pb quimeric fragment formed by the left flanking sequences (soybean genome "Gm chr9") and a part of the inserted construct.

Oligonucleotides and Probe:

```
817 (SEQ ID NO: 26):
5 GCAACTGAACTCAGACCACTG 3

818 (SEQ ID NO: 27):
5 GAGCTTGAGCTTGGATCAGA 3

819 (SEQ ID NO: 28):
5-FAM-TTGTCGTTTCCCGCCTTCAGTTTAA-BHQ1-3
```

QPCR Protocol:

| | |
|---|---|
| 2 ul | Genomic DNA (100 ng/ul) |
| 5.9 ul | mqH2O |
| 10 ul | qPCR SuperMix Roche (2X) |
| 0.5 ul | Probe (10 uM) |
| 0.8 ul | Primer F (10 uM) |
| 0.8 ul | Primer R (10 uM) |
| 20 ul | |

Amplification Program:

| Temp. (° C.) | Time (min) | Variation (° C./s) | |
|---|---|---|---|
| 95 | 5 | 4.4 | Denaturation |

| Temp. (° C.) | Time (s) | Variation (° C./s) | |
|---|---|---|---|
| 95 | 10 | 4.4 | 35 cycles-qPCR |
| 55 | 30 | 2.2 | |
| 72 | 10 | 4.4 | |

| Temp. (° C.) | Time (min) | Variation (° C./s) | |
|---|---|---|---|
| 10 | 5 | 2.2 | Cooling |

Detection of Insertion Site Towards LB

The oligonucleotides 868 (SEQ ID NO: 29) and 752 (SEQ ID NO: 30) amplify a 356 pb quimeric fragment formed by the right flanking sequences (soybean genome "Gm chr9") and part of the event IND-ØØ41Ø-5.

Oligonucleotides:

```
868 (SEQ ID NO: 29):
5 CCGCAATGTGTTATTAAGTTGTC 3

752 (SEQ ID NO: 30):
5 GGCTGCAAGTTTTGGTCAAT 3
```

PCR Protocol:

| | |
|---|---|
| 2 ul | Genomic DNA (100 ng/ul) |
| 2 ul | PCR buffer solution 10X |
| 1.6 ul | MgCl2 (25 mM) |
| 1 ul | Primer F (10 uM) |
| 1 ul | Primer R (10 uM) |
| 0.4 ul | dNTPs (10 mM) |
| 0.1 ul | Taq |
| 11.9 ul | mqH2O |
| 20 ul | |

Amplification Program:

| | |
|---|---|
| 94° C. 4 min | |
| 94° C. 30 seg | |
| 55° C. 30 seg | 35 cycles |
| 72° C. 30 seg | |
| 4° C. 2 min | |

HaHB4 Detection

Oligonucleotides 530 (SEQ ID NO: 31) and 531 (SEQ ID NO: 32) amplify a 68 pb fragment within HaHb4 transgene.

Oligonucleotides and Robe:

```
530 (SEQ ID NO: 31):
5 CGCCACTTGACGAGGATGA 3

531 (SEQ ID NO: 32):
5 CGAGACCCGAGTTAAGGATGAAAC 532 (SEQ ID NO: 33):
5-FAM-AGCCCGAGTTTATGTGCCAACTGGT-BHQ1-3
```

QPCR Protocol:

| | |
|---|---|
| 2 ul | Genomic DNA (100 ng/ul) |
| 5.9 ul | mqH2O |
| 10 ul | Roche SuperMix qPCR (2X) |
| 0.5 ul | Probe (10 uM) |
| 0.8 ul | Primer F (10 uM) |
| 0.8 ul | Primer R (10 uM) |
| 20 ul | |

Amplification Program:

| Temp. (° C.) | Time (min) | Variation (° C./s) | |
|---|---|---|---|
| 95 | 5 | 4.4 | Denaturation |

| Temp. (° C.) | Time (s) | Variation (° C./s) | |
|---|---|---|---|
| 95 | 10 | 4.4 | qPCR-35 cycles |
| 55 | 30 | 2.2 | Bar detection |
| 72 | 1 | 4.4 | Oligonucleotides 527 (SEQ ID NO: 34) and 528 (SEQ ID NO: 35) amplify a 84 pb fragment within bar transgene. |

| Temp. (° C.) | Time (min) | Variation (° C./s) | |
|---|---|---|---|
| 10 | 5 | 2.2 | Cooling |

Oligonucleotides and Probe:

```
527 (SEQ ID NO: 34):
5 CTGCACCATCGTCAACCACTAC 3

528 (SEQ ID NO: 35):
5 GGTCGTCCGTCCACTCCTG 3

529 (SEQ ID NO: 36):
5'-HEX-TCGAGACAAGCACGGTCAACTTCC-BHQ1-3'
```

QPCR Protocol:

| | |
|---|---|
| 2 ul | Genomic DNA (100 ng/ul) |
| 5.9 ul | mqH2O |
| 10 ul | qPCR SuperMix Roche (2X) |
| 0.5 ul | Probe (10 uM) |
| 0.8 ul | Primer F (10 uM) |
| 0.8 ul | Primer R (10 uM) |
| 20 ul | |

Amplification Program:

| Temp. (° C.) | Time (min) | Variation (° C./s) | |
|---|---|---|---|
| 95 | 5 | 4.4 | Denaturation |

| Temp. (° C.) | Time (s) | Variation (° C./s) | |
|---|---|---|---|
| 95 | 10 | 4.4 | qPCR-35 cycles |
| 55 | 30 | 2.2 | |
| 72 | 1 | 4.4 | |

-continued

| Temp. (° C.) | Time (min) | Variation (° C./s) | |
|---|---|---|---|
| 10 | 5 | 2.2 | Cooling |

In the case that HaHB4 and bar detection were necessary, it may be performed simultaneously by multiplex qPCR with the last two systems. The HaHB4 probe has a FAM fluorophore while Bar probe has a HEX fluorophore, enabling detection of both amplifications with different filters.

Furthermore, HaHB4 as well as bar (separately) can be simultaneously detected with endogenous control through multiplex qPCR, provided that said control has a fluorophore different from that of the gene of interest. An example of endogenous control is soybean-specific Lecithin gene. Protocol and amplification program for multiplex PCR are detailed below.

Multiplex qPCR Protocol:

| | |
|---|---|
| 2 ul | Genomic DNA (100 ng/ul) |
| 3.8 ul | dd(H2O) |
| 10 ul | Roche SuperMix qPCR (2X) |
| 0.5 ul | Gen 1 probe (10 uM) |
| 0.8 ul | Gen 1 primer F(10 uM) |
| 0.8 ul | Gen 1 primer R (10 uM) |
| 0.5 ul | Gen 2 probe (10 uM) |
| 0.8 ul | Gen 2 primer F (10 uM) |
| 0.8 ul | Gen 2 primer R (10 uM) |
| 20 ul | |

Amplification Program:

| Temp. (° C.) | Time (min) | Variation (° C./s) | |
|---|---|---|---|
| 95 | 5 | 4.4 | Denaturation |

| Temp. (° C.) | Time (s) | Variation (° C./s) | |
|---|---|---|---|
| 95 | 10 | 4.4 | qPCR-35 cycles |
| 55 | 30 | 2.2 | |
| 72 | 1 | 4.4 | |

| Temp. (° C.) | Time (min) | Variation (° C./s) | |
|---|---|---|---|
| 10 | 5 | 2.2 | Cooling |

Ie1 Detection

Oligonucleotides 718 (SEQ ID NO: 37) and 719 (SEQ ID NO: 38) amplify a 118 pb fragment within Lecithin 1 gene.

Oligonucleotides and Probe:

```
718 (SEQ ID NO: 37):
5 CTACTGACCAGCAAGGCAAA 3

719 (SEQ ID NO: 38):
5 TCACAATAGCGTCTCCTTGG 3

720 (SEQ ID NO: 39):
5'-HEX-TCGTGCCGAAGCAACCAAACA-BHQ1-3'
``` qPCR Protocol:

| | |
|---|---|
| 2 ul | Genomic DNA (100 ng/ul) |
| 5.9 ul | dd (H2O) |
| 10 ul | Roche Supermix qPCR (2X) |
| 0.5 ul | Probe (10 uM) |
| 0.8 ul | Primer F (10 uM) |
| 0.8 ul | Primer R (10 uM) |
| 20 ul | |

Amplification Program:

| Temp. (° C.) | Time (min) | Variation (° C./s) | |
|---|---|---|---|
| 95 | 5 | 4.4 | Denaturation |

| Temp. (° C.) | Time (s) | Variation (° C./s) | |
|---|---|---|---|
| 95 | 10 | 4.4 | qPCR-35 cycles |
| 55 | 30 | 2.2 | |
| 72 | 1 | 4.4 | |

| Temp. (° C.) | Time (min) | Variation (° C./s) | |
|---|---|---|---|
| 10 | 5 | 2.2 | Cooling |

Detection of Heterozygous Individuals

Event insertion is contiguous to 3'UTR region of gene Glyma.09g142000, formerly known as Glyma09g26270. Using oligonucleotides hybridizing in the flanking sequences of the insertion sites it was possible to differentiate the wild allele (they amplify a 205 pb fragment) from the allele having the insert of IND-0041∅-5 (in this case, they amplify 4710 pb).

For the detection of heterozygous individuals, detection of event IND-00410-5 was performed in first place by means of any of the 2 event-specific systems previously mentioned and then a qPCR was conducted to detect the wild allele.

Oligonucleotides 934 (SEQ ID NO: 40) and 935 (SEQ ID NO: 41) amplify a 205 pb fragment formed by the flanking sequences of the IND-0041∅-5 event insertion site and a part of 142 pb lost during transformation (absent in event IND-0041∅-5).

Oligonucleotides and Probe:

```
934 (SEQ ID NO: 40):
5 AGACCACTGAAATAGAGAGAAAG 3

935 (SEQ ID NO: 41):
GGAGTTCTGATAATTGTTATCGTC 936 (SEQ ID NO: 42):
5 HEX-TGAAGTGAGATGATTGAGGGTGGG-BHQ1 3
```

PCR Protocol:

| | |
|---|---|
| 2 ul | Genomic DNA (100 ng/ul) |
| 5.9 ul | mq(H2O) |
| 10 ul | SuperMix qPCR (2X) |
| 0.5 ul | Probe (10 uM) |
| 0.8 ul | Primer F (10 uM) |
| 0.8 ul | Primer R (10 uM) |
| 20 ul | |

Amplification Program:

| Temp. (° C.) | Time (min) | Variation (° C./s) | |
|---|---|---|---|
| 95 | 5 | 4.4 | Denaturation |

| Temp. (° C.) | Time (s) | Variation (° C./s) | |
|---|---|---|---|
| 95 | 10 | 4.4 | qPCR-35 cycles |
| 55 | 30 | 2.2 | |
| 72 | 10 | 4.4 | |

| Temp. (° C.) | Time (min) | Variation (° C./s) | |
|---|---|---|---|
| 40 | 5 | 1.9 | Cooling |

Example 5: Susceptibility to Abiotic Stress Factors and Yield

The environments in which event IND-ØØ41Ø-5 and control were assessed were different with respect to their potential yield probably due to the combination of stress factors such as drought, salinity and low temperatures (osmotic stresses), high temperatures, excess of radiation, low nutrient availability, soil compaction preventing root development, etc. The efficacy of the transgenic event was assessed over three growing seasons in different locations and in different sowing dates, a total of 16 sites were assessed.

The set of these stress factors combined allowed the separation of the environments in categories of high, medium, and low yield potential.

With the transgenic event a yield higher that control was obtained with a level of statistical significance of 10% (p=0.09) for sites with yields lower than 2000 kg ha-1 (W1, W2, P, I1 y J1). Yield difference was 12% favourable to the transgenic event. For higher yield categories no significant differences were found between the event and control, showing the absence of penalty in conditions of medium (2000-3000 Kg ha-1) (I2, G1, G2, J2 y K) or high yield potential (>3000 Kg ha-1) (D2, C, Q2, L, A y F) (Table 5).

sons in different locations and in different sowing dates, a total of 16 sites were assessed Twelve out of sixteen sites correspond to the growing season 2012-2013, wherein all agronomic parameters, both in the transgenic event and control, as well as in the varieties used as reference were measured. In said growing season, the yields of the Northern and Southern core areas were largely higher than in the previous ones, furthermore, historical yields never obtained before were observed in isolated lots of land (Bolsa de Cereales, 2013). The four remaining sites correspond to assays performed in previous growing seasons to determine the efficacy of the event as compared to control. These four assays correspond to the following locations: Hughes, Santa Fe (Site L, 2011-2012), Quimili, Santiago del Estero (2009-2010, Site K) and Liborio Luna, San Luis (2009-2010) with two hydrological conditions: low availability (J1) and high availability (J2). Data were analyzed by analysis of variance using sites and genotypes as factors and evaluating the significance of genotype-environment interaction. "A posteriori" comparisons were made using a least significant differences (LSD) test.

Figure 13:
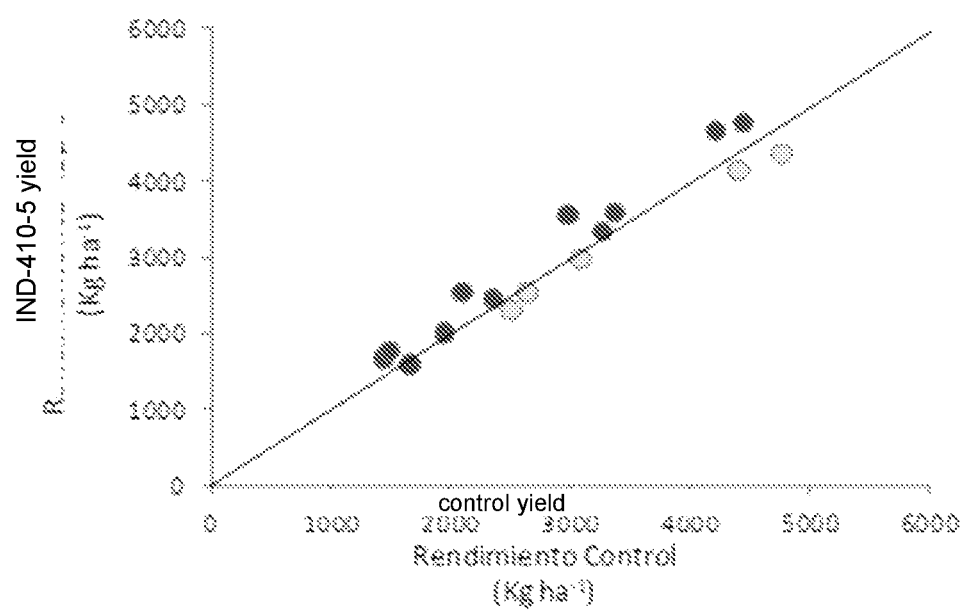
FIG. 13. Transgenic event and control yield for 16 evaluated sites. Darker Solid Circles indicate the sites for which transgenic event had higher yield than control and lighter circles are the sites for which the event had lower yield than control.

Results confirmed the presence of genotype-environment interaction (p=0.02) for the evaluated sites. The transgenic event had a higher yield in eleven out of sixteen sites, with an average difference of 11% for the sites with positive differences (FIG. 13).

The introduced gene response in terms of yield was also evaluated with respect to control in sites grouped by yield categories. Grouping sites with similar ranks allows the evaluation of the event response under different potential yield conditions. A higher yield was obtained with the transgenic event with respect to control with a significance level of 10% (p=0.09) for sites with yields lower than 2000 kg ha-1 (W1, W2, P, I1, and J1). Yield difference was 12% in favor of the transgenic event. For higher yield categories, no significative differences were found between event and control, showing the absence of penalty in conditions of medium (2000-3000 Kg ha-1) (I2, G1, G2, J2 y K) or high (>3000 Kg ha-1) (D2, C, Q2, L, A y F) (Table 5) yield potential.

TABLE 5

Mean yields for transgenic event and control for low, medium, and high yield potential environments.

| | Mean (SEM) | | | | |
|---|---|---|---|---|---|
| Environments | IND-ØØ41Ø-5 | | Williams 82 | | Sites |
| Low potential | 1900.4 | (86.6) | 1699.1 | (80) | * W1, W2, P, I1, J1 |
| Medium potential | 2646 | (104.2) | 2649.3 | (82.5) | NS G1, G2, I2, J2, K |
| High potential | 4209.6 | (131) | 4117.4 | (123.8) | NS C, D2, Q2, A, F, L |

*indicates significant differences ($\alpha = 0.1$)
NS: non significant differences These results confirmed the presence of an expected genotype-environment interaction (p=0.02) due to the different combination of abiotic stresses specific to each site or environment and showed that susceptibility to these factors in the transgenic event is specifically associated to the characteristics related to the gene mode of action.

The yields observed for event IND-ØØ41Ø-5 and its control were analyzed in individual sites as specific environment conditions play a key rol in the expression of the phenotype associated to the introduced gene. The efficacy of the introduced gene was assessed over three growing sea-

SEQUENCE LISTING

<110> BIOCERES, INC.
  Chiozza, Mar iana
  Dezar, Carlos
  Miranda, Patricia
  Vazquez, Martin
  Watson, Geronimo
<120> SOYBEAN TRANSGENIC EVENT IND-00410-5
<130> SOYBEAN TRANSGENIC EVENT IND-00410-5
<160> 43
<170> PatentIn version 3.5

<210> 1
<211> 4623
<212> DNA
<213> Artificial Sequence
<220>
<223> Insert and flanking regions
<400> 1
tggcaggata tattgtggtg taaacaaatt gacgcttaga caacttaata aca-
cattgcg 60
gacgttttta atgtactgaa ttaacgccga attgctctag cattcgccat
tcaggctgcg 120
caactgttgg gaagggcgat cggtgcgggc ctcttcgcta ttacgccagc
tggcgaaagg 180
gggatgtgct gcaaggcgat taagttgggt aacgccaggg ttttcccagt
cacgacgttg 240
taaaacgacg gccagtgcca agctaattcg cttcaagacg tgctcaaatc act-
atttcca 300
caccccctata tttctattgc actcccttt aactgttttt tattacaaaa atgccctgga
360
aaatgcactc ccttttgtg tttgtttttt tgtgaaacga tgttgtcagg taatttattt
420
gtcagtctac tatggtggcc cattatatta atagcaactg tcggtccaat
agacgacgtc 480
gattttctgc atttgtttaa ccacgtggat tttatgacat tttatattag ttaatttgta
540
aaacctaccc aattaaagac ctcatatgtt ctaaagacta atacttaatg
ataacaattt 600
tcttttagtg aagaaaggga taattagtaa atatggaaca agggcagaag att-
tattaaa 660
gccgcggtaa gagacaacaa gtaggtacgt ggagtgtctt aggtgactta
cccacataac 720
ataaagtgac attaacaaac atagctaatg ctcctatttg aatagtgcat atcag-
catac 780
cttattacat atagatagga gcaaactcta gctagattgt tgagcagatc
tcggtgacgg 840
gcaggaccgg acgggcggt accggcaggc tgaagtccag ctgccagaaa
cccacgtcat 900
gccagttccc gtgcttgaag ccggccgccc gcagcatgcc gcgggggggca
tatccgagcg 960
cctcgtgcat gcgcacgctc gggtcgttgg gcagcccgat gacagcgacc 40
acgctcttga 1020
agccctgtgc ctccagggac ttcagcaggt gggtgtagag cgtggagccc
agtcccgtcc 1080
gctggtggcg ggggagacg tacacggtcg actcggccgt ccagtcgtag
gcgttgcgtg 1140
ccttccaggg gcccgcgtag gcgatgccgg cgacctcgcc gtccacctcg
gcgacgagcc 1200
agggatagcg ctcccgcaga cggacgaggt cgtccgtcca ctcctgcggt
tcctgcggct 1260
cggtacggaa gttgaccgtg cttgtctcga tgtagtggtt gacgatggtg 50
cagaccgccg 1320
gcatgtccgc ctcggtggca cggcggatgt cggccgggcg tcgttctggg
ctcatggtag 1380
atcccccgtt cgtaaatggt gaaaattttc agaaaattgc ttttgcttta
aaagaaatga 1440
ttttaaattgc tgcaatagaa gtagaatgct tgattgcttg agattcgttt
gttttgtata 1500
tgttgtgttg agaattaatt ctcgaggtcc tctccaaatg aaatgaactt cct-
tatatag 1560
aggaagggtc ttgcgaagga tagtgggatt gtgcgtcatc ccttacgtca gtg-
gagatat 1620
cacatcaatc cacttgcttt gaagacgtgg ttggaacgtc ttcttttcc
acgatgctcc 1680
tcgtgggtgg ggtccatct ttgggaccac tgtcggtaga ggcatcttga
acgatagcct 1740
ttccttttatc gcaatgatgc catttgtagg agccaccttc cttttccact atctt-
cacaa 1800 taaagtgaca gatagctggg caatggaatc cgaggaggtt tccggatatt
acccttttgtt 1860
gaaaagtctc aattgcccttt tggtcttctg agactgtatc tttgatatttt ttg-
gagtaga 1920
caagtgtgtc gtgctccacc atgttatcac atcaatccac ttgctttgaa
gacgtggttg 1980
gaacgtcttc ttttccacg atgctcctcg tgggtggggg tccatctttg ggac-
cactgt 2040
cggcagaggc atcttcaacg atggcctttc ctttatcgca atgatggcat
ttgtaggagc 2100
cacccttcctt ttccactatc ttcacaataa agtgacagat agctgggcaa
tggaatccga 2160
ggaggtttcc ggatattacc ctttgttgaa aagtctcaat tgcccttttgg tcttct-
gaga 2220
ctgtatcttt gatatttttg gagtagacaa gtgtgtcgtg ctccaccatg
ttgacctgca 2280
ggtcgacacc tggcacatcg tatcttatct cttttgtcgt ttccaacaca
ccacaacaca 2340
cctacaaacg tgtcaattca cacttcacca atttcatttc cttttagtca atcatat-
taa 2400
aagtagtagc ccccacccc atttgttacc taccatttcc cacttaata atcacc-
cacg 2460
ctatgtccac ttgtactttt gtttgcacac aactcttccc ataaaatatc aaac-
caaatt 2520
tttttttagtg gaaaacaaat tccccaaata gaatactaac gaaattcatc
gcatcagaat 2580
acactcatct ctgaacagtg gcgaagcttg acgttttcga cggggggtcg
gaaaacgtat 2640
gtacccgaaa tttctataga atcggggggt cgaaaacgta tacccccaaa
attctatac 2700
gaaaactaca tatataacac tactgagcaa aaagttcggg ggttcgggcg
ccccctcccgg 2760
ccccttcaaa gcttcgccaa tgtctctgaa ccgaagaaaa ccctcactcg
tctactagcc 2820
aatgaatcct caccaggaa aaccctcact cgtcttactg gactattggc gcttc-
caaat 2880
ggactacttg cgaaattcac cacattggga tacactcgtc tactgcggtg
aggtaaaacc 2940
cgcttggttc aaggatcgaa ctagcgattg ctgcctactc gcctaatctc ccat-
catcaa 3000
caggtgccgc cgaaacaaaa tgctggggc gggagttgaa cctaggtcca
gtgacgcacc 3060
catgaatttt ttttctaggg atgcgaacga gtggtttaac catactttta
agaggtgcga 3120
tcggaaattt tacctataaa atacactaaa aaagtccaa gggtccaccc
accccttaac 3180
ctaagtccgc ctttgtctgg atcacgtgaa acatcaggtc tctcccttac
cagtccagct 3240
acgactcatt gacaaaatat caaaaccata tgatttgag ttttatctca
accgaaagtg 3300
acatcatgac agagaatcga cataaccaaa acgtgtaaac gtacaactca
ccattggctt 3360
gaaaaggaca aaacaggtag gattcttgtc aaattcaacg cgtacacctg 55
tgcttcatct 3420
aaacccccata cttttaagaa cctttataaa gaccactcac tatatatatca
catatataat 3480
atcacttatc aaaccctcgg atccaccatg tctcttcaac aagtaacaac
caccaggaag 3540
aaccgaaacg agggggcgag acgatttacc gacaaacaaa taagtttcct
agagtacatg 3600
tttgagacac agtcgagacc cgagttaagg atgaaacacc agttggcaca
taaactcggg 3660
cttcatcctc gtcaagtggc gatatggttc cagaacaaac gcgcgcgatc
aaagtcgagg 3720
cagattgagc aagagtataa cgcgctaaag cataactacg agacgcttgc
gtctaaatcc 3780 gagtctctaa agaaagagaa tcaggccta ctcaatcaat tggaggtgct gagaaatgta 3840
gccgaaaagc atcaagagaa aactagtagt agtggcagcg gtgaagaatc ggatgatcgg 3900
tttacgaact ctccggacgt tatgtttggt caagaaatga atgttccgtt ttgcgacggt 3960
tttgcgtacc ttgaagaagg aaacagtttg ttggagattg aagaacaact gccagacctt 4020
caaaagtggt gggagttcta agagctcgaa tttccccgat cgttcaaaca tttggcaata 4080
aagttcttta agattgaatc ctgttgccgg tcttgcgatg attatcatat aatttctgtt 4140
gaattacgtt aagcatgtaa taattaacat gtaatgcatg acgttattta tgagatgggt 4200
ttttatgatt agagtcccgc aattatacat ttaatacgcg atagaaaaca aaatatagcg 4260
cgcaaactag gataaattat cgcgcgcggt gtcatctatg ttactagatc gggaattcgt 4320
aatcatgtca tagctgtttc ctgtgtgaaa ttgttatccg ctcacaattc cacacacat 4380
acgagccgga agcataaagt gtaaagcctg gggtgcctaa tgagtgagct aactcacatt 4440
aattgcgttg cgctcactgc ccgctttcca gtcgggaaac ctgtcgtgcc agctgcatta 4500
atgaatcggc caacgcgcgg ggagaggcgg tttgcgtatt ggagcttgag cttggatcag 4560
attgtcgttt cccgccttca gtttaaacta tcagtgtttg acaggatata ttggcgggta 4620
aac 4623

<210> 2
<211> 139
<212> DNA
<213> Artificial sequence
<220>
<223> Right Junction Sequence
<400> 2
tgacaggata tattggcggg taaacctaag agaaaagagc gtttattaga ataatcggat 60
atttaaaagg gcgtgaaaag gtttatccgt tcgtccattt gtatgtgcat gccaaccaca 120
gggttcccct cgggatcaa 139

<210> 3
<211> 268
<212> DNA
<213> Artificial sequence
<220>
<223> Left Junction sequence
<400> 3
cgaattgatc acaggcagca acgctctgtc atcgttacaa tcaacatgct accctccgcg 60
agatcatccg tgtttcaaac ccggcagctt agttgccgtt cttccgaata gcatcggtaa 120
catgagcaaa gtctgccgcc ttacaacggc tctcccgctg acgccgtccc ggactgatgg 180
gctgcctgta tcgagtggtg atttgtgcc gagctgccgg tcggggagct gttggctggc 240
tggtggcagg atatattgtg gtgtaaac 268

<210> 4
<211> 4573
<212> DNA
<213> Artificial sequence
<220>
<223> Insert sequence
<400> 4
aaattgacgc ttagacaact taataacaca ttgcggacgt ttttaatgta ctgaattaac 60
gccgaattgc tctagcattc gccattcagg ctgcgcaact gttgggaagg gcgatcggtg 120
cgggcctctt cgctattacg ccagctggcg aaaggggat gtgctgcaag gcgattaagt 180
tgggtaacgc caggggtttc ccagtcacga cgttgtaaaa cgacggccag tgccaagcta 240
attcgcttca agacgtgctc aaatcactat ttccacaccc ctatatttct attgcactcc 300
cttttaactg tttttatta caaaaatgcc ctggaaaatg cactccctt ttgtgtttgt 360
tttttgtga aacgatgttg tcaggtaatt tatttgtcag tctactatgg tggccatta 420
tattaatagc aactgtcggt ccaatagacg acgtcgattt tctgcatttg tttaaccacg 480
tggattttat gacatttat attagttaat ttgtaaaacc tacccaatta aagacctcat 540
atgttctaaa gactaatact taatgataac aattttcttt tagtgaagaa agggataatt 600
agtaaatatg gaacaagggc agaagattta ttaaagccgc ggtaagagac aacaagtagg 660
tacgtggagt gtcttaggtg acttacccac ataacataaa gtgacattaa caaacatagc 720
taatgctcct atttgaatag tgcatatcag catacctat tacatataga taggagcaaa 780
ctctagctag attgttgagc agatctcggt gacgggcagg accggacggg gcggtaccgg 840
caggctgaag tccagctgcc agaaaccac gtcatgccag ttcccgtgct tgaagccggc 900
cgcccgcagc atgccgcggg gggcatatcc gagcgcctcg tgcatgcgca cgctcgggtc 960
gttgggcagc ccgatgacag cgaccacgct cttgaagccc tgtgcctcca gggacttcag 1020
caggtgggtg tagagcgtgg agcccagtcc cgtccgctgg tggcgggggg agacgtacac 1080
ggtcgactcg gccgtccagt cgtaggcgtt gcgtgccttc caggggcccg cgtaggcgat 1140
gccggcgacc tcgccgtcca cctcggcgac gagccaggga tagcgctccc gcagacggac 1200
gaggtcgtcc gtccactcct gcggttcctg cggctcggta cggaagttga ccgtgcttgt 1260
ctcgatgtag tggttgacga tggtgcagac cgccggcatg tccgcctcgg tggcacggcg 1320
gatgtcggcc gggcgtcgtt ctgggctcat ggtagatccc ccgttcgtaa atggtgaaaa 1380
ttttcagaaa attgctttg cttaaaaga aatgatttaa attgctgcaa tagaagtaga 1440
atgcttgatt gcttgagatt cgtttgtttt gtatatgttg tgttgagaat taattctcga 1500
ggtcctctcc aaatgaaatg aacttcctta tatagaggaa gggtcttgcg aaggatagtg 1560
ggattgtgcg tcatccctta cgtcagtgga gatatcacat caatccactt gctttgaaga 1620
cgtggttgga acgtcttctt ttttccacgat gctcctcgtg ggtgggggtc catctttggg 1680
accactgtcg gtagaggcat cttgaacgat agccttttcct ttatcgcaat gatggcattt 1740
gtaggagcca ccttcctttt ccactatctt cacaataaag tgacagatag ctgggcaatg 1800
gaatccgagg aggttccgg atattcccct ttgttgaaaa gtctcaattg cccttttggtc 1860
ttctgagact gtatcttga tattttggga gtagacaagt gtgtcgtgct ccaccatgtt 1920
atcacatcaa tccacttgct tgaagacgt ggttggaacg tcttcttttt ccacgatgct 1980
cctcgtgggt ggggtccat ctttgggacc actgtcggca gaggcatctt caacgatggc 2040
ctttcctttt atcgcaatgat ggcatttgta ggagccacct tcctttttcca ctatcttcac 2100 aataaagtga cagatagctg ggcaatggaa tccgaggagg tttccggata ttacccttg 2160 ttgaaaagtc tcaattgccc tttggtcttc tgagactgta tctttgatat ttttggagta 2220
gacaagtgtg tcgtgctcca ccatgttgac ctgcaggtcg acacctggca catcgtatct 2280
tatctctttt gtcgtttcca acacaccaca acacacctac aaacgtgtca attcacactt 2340
caccaatttc atttcctttt agtcaatcat attaaaagta gtagcccccca cccccatttg 2400 ttacctacca tttcccactt taataatcac ccacgctatg tccacttgta cttttgtttg 2460
cacacaactc ttcccataaa atatcaaacc aaatttttt tagtggaaaa caaattcccc 2520
aaatagaata ctaacgaaat tcatcgcatc agaatacact catctctgaa cagtggcgaa 2580
gcttgacgtt ttcgacgggg ggtcggaaaa cgtatgtacc cgaaatttct atagaatcgg 2640
ggggtcgaaa acgtatatac ccaaaatttc tatacgaaaa ctacatatat aacactactg 2700
agcaaaaagt tcggggttc gggcgcccct cccggcccct tcaaagcttc gccaatgtct 2760
ctgaaccgaa gaaaaccctc actcgtctac tagccaatga atcctcacca gggaaaaccc 2820
tcactcgtct tactggacta ttggcgcttc caaatggact acttgcgaaa ttcaccacat 2880
tgggatacac tcgtctactg cggtgaggta aaacccgctt ggttcaagga tcgaactagc 2940
gattgctgcc tactcgccta atctcccatc atcaacaggt gccgccgaaa caaaatgctg 3000
ggggcgggag ttgaacctag gtccagtgac gcacccatga attttttttc taggatgcg 3060 aacgagtggt ttaaccatac ttttaagagg tgcgatcgga aattttacct ataaaatca 3120 ctaaaaaagt tccaagggtc cacccacccc ttaacctaag tccgccttg tctgatcac 3180 gtgaaacatc aggtctctcc cttaccagtc cagctacgac tcattgacaa aatatcaaaa 3240
ccatatgatt ttgagttta tctcaaccga aagtgacatc atgacagaga atcgacataa 3300
ccaaaacgtg taaacgtaca actcaccatt gcgttgaaaa ggacaaaaca ggtaggattc 3360
ttgtcaaatt caacgcgtac acctgtgctt catctaaacc ccatactttt aagaaccttt 3420
ataaagacca ctcactatat atacacatat ataatatcac ttatcaaacc ctcgatcca 3480 ccatgtctct tcaacaagta acaaccacca ggaagaaccg aaacgagggg cggagacgat 3540
ttaccgacaa acaaataagt ttcctagagt acatgtttga gacacagtcg agacccgagt 3600
taaggatgaa acaccagttg gcacataaac tcgggcttca tcctcgtcaa gtggcgatat 3660
ggttccagaa caaacgcgcg cgatcaaagt cgaggcagat tgagcaagag tataacgcgc 3720
taaagcataa ctacgagacg cttgcgtcta aatccgagtc tctaaagaaa gagaatcagg 3780
ccctactcaa tcaattggag gtgctgagaa atgtagccga aaagcatcaa gagaaaacta 3840
gtagtagtgg cagcggtgaa gaatcggatg atcggtttac gaactctccg gacgttatgt 3900
ttggtcaaga aatgaatgtt ccgttttgcg acggttttgc gtaccttgaa gaaggaaaca 3960
gtttgttgga gattgaagaa caactgccag accttcaaaa gtggtgggaa ttctaagagc 4020
tcgaatttcc ccgatcgttc aaacatttgg caataaagtt tcttaagatt gaatcctgtt 4080
gccggtcttg cgatgattat catataattt ctgttgaatt acgttaagca tgtaataatt 4140
aacatgtaat gcatgacgtt atttatgaga tgggttttta tgattagagt cccgcaatta 4200
tacatttaat acgcgataga aaacaaaata tagcgcgcaa actaggataa attatcgcgc 4260
gcggtgtcat ctatgttact agatcgggaa ttcgtaatca tgtcatagct gtttcctgtg 4320
tgaaattgtt atccgctcac aattccacac aacatacgag ccggaagcat aaagtgtaaa 4380
gcctggggtg cctaatgagt gagctaactc acattaattg cgttgcgctc actgcccgct 4440
ttccagtcgg gaaacctgtc gtgccagctg cattaatgaa tcggccaacg cgcggggaga 4500
ggcggtttgc gtattggagc ttgagcttgg atcagattgt cgtttcccgc cttcagttta 4560
aactatcagt gtt 4573

<210> 5
<211> 20
<212> DNA
<213> Artificial sequence
<220>
<223> Primer 750
<400> 5
acgcaactga actcagacca 20

<210> 6
<211> 20
<212> DNA
<213> Artificial sequence
<220>
<223> Primer 751
<400> 6
aagtggcgat atggttccag 20

<210> 7
<211> 20
<212> DNA
<213> Artificial sequence
<220>
<223> Primer 752
<400> 7
ggctgcaagt tttggtcaat 20

<210> 8
<211> 20
<212> DNA
<213> Artificial sequence
<220>
<223> Primer 753
<400> 8
ttcggctaca tttctcagca 20

<210> 9
<211> 20
<212> DNA
<213> Artificial sequence
<220>
<223> Primer 754
<400> 9
agccaatgaa tcctcaccag 20

<210> 10
<211> 20
<212> DNA
<213> Artificial sequence
<220>
<223> Primer 755
<400> 10
attaggcgag taggcagcaa 20

<210> 11
<211> 22
<212> DNA
<213> Artificial sequence
<220>
<223> Primer 756
<400> 11
caacacacct acaaacgtgt ca 22
<210> 12
<211> 20
<212> DNA
<213> Artificial sequence
<220>
<223> Primer 757
<400> 12
gggtgggggc tactactttt 20
<210> 13
<211> 21
<212> DNA
<213> Artificial sequence
<220>
<223> Primer 758
<400> 13
cttcagcagg tgggtgtaga g 21
<210> 14
<211> 20
<212> DNA
<213> Artificial sequence
<220>
<223> Primer 759
<400> 14
agtcgaccgt gtacgtctcc 20
<210> 15
<211> 20
<212> DNA
<213> Artificial sequence
<220>
<223> Primer 760
<400> 15
gttgggtcag cctgagtgat 20
<210> 16
<211> 24
<212> DNA
<213> Artificial sequence
<220>
<223> Primer 2527
<400> 16
cgcttgcgtc taaatccgag tctc 24
<210> 17
<211> 20
<212> DNA
<213> Artificial sequence
<220>
<223> Primer 203
<400> 17
caagaccggc aacaggattc 20
<210> 18
<211> 20
<212> DNA
<213> Artificial sequence
<220>
<223> Primer 378
<400> 18
atatggcgct gatctctgct 20
<210> 19
<211> 20
<212> DNA
<213> Artificial sequence
<220>
<223> Primer 1970
<400> 19
ggcggtctgc accatcgtca 20
<210> 20
<211> 24
<212> DNA
<213> Artificial sequence
<220>
<223> Primer 1747
<400> 20
aagacgacca tcgcaaccca tcta 24
<210> 21
<211> 24
<212> DNA
<213> Artificial sequence
<220>
<223> Primer 1748
<400> 21
tagccttcca tccgtgacct caat 24
<210> 22
<211> 24
<212> DNA
<213> Artificial sequence
<220>
<223> Primer 1745
<400> 22
agctgattgg atgtaccgcg agat 24
<210> 23
<211> 24
<212> DNA
<213> Artificial sequence
<220>
<223> Primer 1746
<400> 23
ttcaaatcgt actccggcag gtca 24
<210> 24
<211> 24
<212> DNA
<213> Artificial sequence
<220>
<223> Primer 822
<400> 24
atcaaacatc gacccacggc gtaa 24
<210> 25
<211> 24
<212> DNA
<213> Artificial sequence
<220>
<223> Primer 1127
<400> 25
gatcaattcg ggcacgaacc cagt 24
<210> 26
<211> 21
<212> DNA
<213> Artificial sequence
<220>
<223> Primer 817
<400> 26
gcaactgaac tcagaccact g 21
<210> 27
<211> 20
<212> DNA
<213> Artificial sequence
<220>
<223> Primer 27

<400> 27
gagcttgagc ttggatcaga 20
<210> 28
<211> 25
<212> DNA
<213> Artificial sequence
<220>
<223> Probe 819
<400> 28
ttgtcgtttc ccgccttcag tttaa 25
<210> 29
<211> 23
<212> DNA
<213> Artificial sequence
<220>
<223> Primer 868
<400> 29
ccgcaatgtg ttattaagtt gtc 23
<210> 30
<211> 20
<212> DNA
<213> Artificial sequence
<220>
<223> Primer 752
<400> 30
ggctgcaagt tttggtcaat 20
<210> 31
<211> 19
<212> DNA
<213> Artificial sequence
<220>
<223> Primer 530
<400> 31
cgccacttga cgaggatga 19
<210> 32
<211> 24
<212> DNA
<213> Artificial sequence
<220>
<223> Primer 531
<400> 32
cgagacccga gttaaggatg aaac 24
<210> 33
<211> 25
<212> DNA
<213> Artificial sequence
<220>
<223> Probe 532
<400> 33
agcccgagtt tatgtgccaa ctggt 25
<210> 34
<211> 22
<212> DNA
<213> Artificial sequence
<220>
<223> Primer 527
<400> 34
ctgcaccatc gtcaaccact ac 22
<210> 35
<211> 19
<212> DNA
<213> Artificial sequence
<220>
<223> Primer 528
<400> 35
ggtcgtccgt ccactcctg 19
<210> 36
<211> 24
<212> DNA
<213> Artificial sequence
<220>
<223> Probe 529
<400> 36
tcgagacaag cacggtcaac ttcc 24
<210> 37
<211> 20
<212> DNA
<213> Artificial sequence
<220>
<223> Primer 718
<400> 37
ctactgacca gcaaggcaaa 20
<210> 38
<211> 20
<212> DNA
<213> Artificial sequence
<220>
<223> Primer 719
<400> 38
tcacaatagc gtctccttgg 20
<210> 39
<211> 21
<212> DNA
<213> Artificial sequence
<220>
<223> Probe 720
<400> 39
tcgtgccgaa gcaaccaaac a 21
<210> 40
<211> 23
<212> DNA
<213> Artificial sequence
<220>
<223> Primer 934
<400> 40
agaccactga aatagagaga aag 23
<210> 41
<211> 24
<212> DNA
<213> Artificial sequence
<220>
<223> Primer 935
<400> 41
ggagttctga taattgttat cgtc 24
<210> 42
<211> 24
<212> DNA
<213> Artificial sequence
<220>
<223> Probe 936
<400> 42
tgaagtgaga tgattgaggg tggg 24
<210> 43
<211> 11133
<212> DNA
<213> Artificial sequence
<220>
<223> DNA plasmid
<400> 43
agtactttga tccaacccct ccgctgctat agtgcagtcg gcttctgacg 
ttcagtgcag 60
ccgtcttctg aaaacgacat gtcgcacaag tcctaagtta cgcgacaggc 
tgccgccctg 120 cccttttcct ggcgttttct tgtcgcgtgt tttagtcgca taaagtagaa
tacttgcgac 180 tagaaccgga gacattacgc catgaacaag agcgccgccg ctggcctgct
gggctatgcc 240 cgcgtcagca ccgacgacca ggacttgacc aaccaacggg ccgaactgca
cgcggccggc 300 tgcaccaagc tgttttccga gaagatcacc ggcaccaggc gcgaccgccc
ggagctggcc 360 aggatgcttg accacctacg ccctggcgac gttgtgacag tgaccaggct
agaccgcctg 420 gcccgcagca cccgcgacct actggacatt gccgagcgca tccaggaggc
cggcgcgggc 480 ctgcgtagcc tggcagagcc gtgggccgac accaccacgc cggccggccg
catggtgttg 540 accgtgttcg ccggcattgc cgagttcgag cgttccctaa tcatcgaccg
cacccggagc 600 gggcgcgagg ccgccaaggc ccgaggcgtg aagtttggcc cccgccctac
cctcaccccg 660 gcacagatcg cgcacgcccg cgagctgatc gaccaggaag gccgcaccgt
gaaagaggcg 720 gctgcactgc ttggcgtgca tcgctcgacc ctgtaccgcg cacttgagcg
cagcgaggaa 780 gtgacgccca ccgaggccag gcggcgcggt gccttccgtg aggacgcatt
gaccgaggcc 840 gacgccctgg cggccgccga gaatgaacgc caagaggaac aagcatgaaa
ccgcaccagg 900 acggccagga cgaaccgttt ttcattaccg aagagatcga ggcggagatg
atcgcggccg 960 ggtacgtgtt cgagccgccc gcgcacgtct caaccgtgcg gctgcatgaa
atcctggccg 1020 gtttgtctga tgccaagctg gcggcctggc cggccagctt ggccgctgaa
gaaaccgagc 1080 gccgccgtct aaaaaggtga tgtgtatttg agtaaaacag cttgcgtcat
gcggtcgctg 1140 cgtatatgat gcgatgagta aataaacaaa tacgcaaggg gaacgcatga
aggttatcgc 1200 tgtacttaac cagaaaggcg ggtcaggcaa gacgaccatc gcaacccatc
tagcccgcgc 1260 cctgcaactc gccggggccg atgttctgtt agtcgattcc gatccccagg
gcagtgcccg 1320 cgattgggcg gccgtgcggg aagatcaacc gctaaccgtt gtcggcatcg
accgcccgac 1380 gattgaccgc gacgtgaagg ccatcggccg cgcgacttc gtagtgatcg
acggagcgcc 1440 ccaggcgcg gacttggctg tgtccgcgat caaggcagcc gacttcgtgc
tgattccggt 1500 gcagccaagc ccttacgaca tatgggccac cgccgacctg gtggagctgg
ttaagcagcg 1560 cattgaggtc acggatggaa ggctacaagc ggcctttgtc gtgtcgcggg
cgatcaaagg 1620 cacgcgcatc ggcggtgagg ttgccgaggc gctggccggg tacgagctgc
ccattcttga 1680 gtcccgtatc acgcagcgcg tgagctaccc aggcactgcc gccgccggca
caaccgttct 1740 tgaatcagaa cccgagggca cgctgcccg cgaggtccag gcgctggccg
ctgaaattaa 1800 atcaaaactc atttgagtta atgaggtaaa gagaaaatga gcaaaagcac
aaacacgcta 1860 agtgccggcc gtccgagcgc acgcagcagc aaggctgcaa cgttggccag
cctggcagac 1920 acgccagcca tgaagcgggt caactttcag ttgccggcgg aggatcacac
caagctgaag 1980 atgtacgcgg tacgccaagg caagaccatt accgagctgc tatctgaata
catcgcgcag 2040 ctaccagagt aaatgagcaa atgaataaat gagtagatga attttagcgg
ctaaaggagg 2100 cggcatggaa aatcaagaac aaccaggcac cgacgccgtg gaatgcccca
tgtgtggagg 2160 aacgggcggt tggccaggcg taagcggctg ggttgtctgc cggccctgca
atggcactgg 2220 aaccccaag cccgaggaat cggcgtgagc ggtcgcaaac catccggccc
ggtacaaatc 2280 ggcgcggcgc tgggtgatga cctggtggag aagttgaagg ccgcgcaggc
cgcccagcgg 2340 caacgcatcg aggcagaagc acgccccgt gaatcgtggc aagcggccgc
tgatcgaatc 2400 cgcaaagaat cccggcaacc gccggcagcc ggtgcgccgt cgattaggaa
gccgcccaag 2460 ggcgacgagc aaccagattt tttcgttccg atgctctatg acgtgggcac ccgc-
gatagt 2520 cgcagcatca tggacgtggc cgttttccgt ctgtcgaagc gtgaccgacg
agctggcgag 2580 gtgatccgct acgagcttcc agacgggcac gtagaggttt ccgcagggcc
ggccggcatg 2640 gccagtgtgt gggattacga cctggtactg atggcggttt cccatctaac
cgaatccatg 2700 aaccgatacc gggaagggaa gggagacaag cccgccgcg tgttccgtcc
acacgttgcg 2760 gacgtactca agttctgccg gcgagccgat ggcggaaagc agaaagacga
cctggtagaa 2820 acctgcattc ggttaaacac cacgcacgtt gccatgcagc gtacgaagaa
ggccaagaac 2880 ggccgcctgg tgacggtatc cgagggtgaa gccttgatta gccgctacaa
gatcgtaaag 2940 agcgaaaccg ggcggccgga gtacatcgag atcgagctag ctgattggat
gtaccgcgag 3000 atcacagaag gcaagaaccc ggacgtgctg acggttcacc ccgattactt ttt-
gatcgat 3060 cccggcatcg gccgttttct ctaccgcctg gcacgccgcg ccgcaggcaa
ggcagaagcc 3120 agatggttgt tcaagacgct acgaacgc agtggcagcg ccggagagtt
caagaagttc 3180 tgtttcaccg tgcgcaagct gatcgggtca aatgacctgc cggagtacga ttt-
gaaggag 3240 gaggcgggc aggctggccc gatcctagtc atgcgctacc gcaacctgat
cgagggcgaa 3300 gcatccgccg gttcctaatg tacggagcag atgctagggc aaattgccct
agcagggaa 3360 aaaggtcgaa aaggtctctt tcctgtggat agcacgtaca ttgggaaccc
aaagccgtac 3420 attgggaacc ggaacccgta cattgggaac ccaaagccgt acattgggaa
ccggtcacac 3480 atgtaagtga ctgatataaa agagaaaaaa ggcgattttt ccgcctaaaa ctctt-
taaaa 3540 cttattaaaa ctcttaaaac ccgcctggcc tgtgcataac tgtctggcca
gcgcacagcc 3600 gaagagctgc aaaaagcgcc tacccttcgg tcgctgcgct ccctacgccc
cgccgcttcg 3660 cgtcggccta tcgcggccgc tggccgctca aaaatggctg gcctacggcc
aggcaatcta 3720 ccagggcgcg gacaagccgc gccgtcgcca ctcgaccgcc ggcgcccaca
tcaaggcacc 3780 ctgcctcgcg cgtttcggtg atgacggtga aaacctctga cacatgcagc
tcccggagac 3840 ggtcacagct tgtctgtaag cggatgccgg gagcagacaa gcccgtcagg
gcgcgtcagc 3900 gggtgttggc gggtgtcggg gcgcagccat gacccagtca cgtagcgata
gcggagtgta 3960 tactggctta actatgcggc atcagagcag attgtactga gagtgcacca
tatgcggtgt 4020 gaaataccgc acagatgcgt aaggagaaaa taccgcatca ggcgctcttc
cgcttcctcg 4080 ctcactgact cgctgcgctc ggtcgttcgg ctgcggcgag cggtatcagc tcactcaaag 4140
gcggtaatac ggttatccac agaatcaggg gataacgcag gaaagaacat gtgagcaaaa 4200
ggccagcaaa aggccaggaa ccgtaaaaag gccgcgttgc tggcgttttt ccataggctc 4260
cgcccccctg acgagcatca caaaaatcga cgctcaagtc agaggtggcg aaacccgaca 4320
ggactataaa gataccaggc gtttccccct ggaagctccc tcgtgcgctc tcctgttccg 4380
accctgccgc ttaccggata cctgtccgcc tttctccctt cgggaagcgt ggcgctttct 4440
catagctcac gctgtaggta tctcagttcg gtgtaggtcg ttcgctccaa gctgggctgt 4500
gtgcacgaac cccccgttca gcccgaccgc tgcgccttat ccggtaacta tcgtcttgag 4560
tccaacccgg taagacacga cttatcgcca ctggcagcag ccactggtaa caggattagc 4620
agagcgaggt atgtaggcgg tgctacagag ttcttgaagt ggtggcctaa ctacggctac 4680
actagaagga cagtatttgg tatctgcgct ctgctgaagc cagttacctt cggaaaaaga 4740
gttggtagct cttgatccgg caaacaaacc accgctggta gcggtggttt ttttgtttgc 4800
aagcagcaga ttacgcgcag aaaaaaagga tctcaagaag atcctttgat cttttctacg 4860
gggtctgacg ctcagtggaa cgaaaactca cgttaaggga ttttggtcat gcatgatata 4920
tctcccaatt tgtgtagggc ttattatgca cgcttaaaaa taataaaagc agacttgacc 4980
tgatagtttg gctgtgagca attatgtgct tagtgcatct aacgcttgag ttaagccgcg 5040
ccgcgaagcg cgctcggctt gaacgaattt ctagctagac attatttgcc gactaccttg 5100
gtgatctcgc ctttcacgta gtggacaaat tcttccaact gatctgcgcg cgaggccaag 5160
cgatcttctt cttgtccaag ataagcctgt ctagcttcaa gtatgacggg ctgatactgg 5220
gccggcaggc gctccattgc ccagtcggca gcgacatcct tcggcgcgat tttgccggtt 5280
actgcgctgt accaatgcg ggacaacgta agcactacat ttcgctcatc gccagcccag 5340
tcgggcggcg agttccatag cgttaaggtt tcatttagcg cctcaaatag atcctgttca 5400
ggaaccggat caaagagttc ctccgccgct ggacctacca aggcaacgct atgttctctt 5460
gcttttgtca gcaagatagc cagatcaatg tcgatcgtgg ctggctcgaa gatacctgca 5520
agaatgtcat tgcgctgcca ttctccaaat tgcagttcgc gcttagctgg ataacgccac 5580
ggaatgatgt cgtcgtgcac aacaatggtg acttctacag cgcggagaat ctcgctctct 5640
ccaggggaag ccgaagtttc caaaaggtcg ttgatcaaag ctcgccgcgt tgtttcatca 5700
agccttacgg tcaccgtaac cagcaaatca atatcactgt gtggcttcag gccgccatcc 5760
actgcggagc cgtacaaatg tacggccagc aacgtcggtt cgagatggcg ctcgatgacg 5820
ccaactacct ctgatagttg agtcgatact tcggcgatca ccgcttcccc catgatgttt 5880
aactttgttt tagggcgact gccctgctgc gtaacatcgt tgctgctcca taacatcaaa 5940
catcgaccca cggcgtaacg cgcttgctgc ttggatgccc gaggcataga ctgtaccca 6000 aaaaacagt cataacaagc catgaaaacc gccactgcgc cgttaccacc gctgcgttcg 6060
gtcaaggttc tggaccagtt gcgtgacggc agttacgcta cttgcattac agcttacgaa 6120
ccgaacgagg cttatgtcca ctgggttcgt gccccgaattg atcacaggca gcaacgctct 6180
gtcatcgtta caatcaacat gctaccctcc gcgagatcat ccgtgtttca aacccggcag 6240
cttagttgcc gttcttccga atagcatcgg taacatgagc aaagtctgcc gccttacaac 6300
ggctctcccg ctgacgccgt cccggactga tgggctgcct gtatcgagtg tgatttgt 6360 gccgagctgc cggtcgggga gctgttggct ggctggtggc aggatatatt gtggtgtaaa 6420
caaattgacg cttagacaac ttaataacac attgcggacg ttttaatgt actgaattaa 6480 cgccgaattg ctctagcatt cgccattcag gctgcgcaac tgttgggaag ggcgatcggt 6540
gcgggcctct tcgctattac gccagctggc gaaaggggga tgtgctgcaa ggcgattaag 6600
ttgggtaacg ccagggtttt cccagtcacg acgttgtaaa acgacggcca gtgccaagct 6660
aattcgcttc aagacgtgct caaatcacta tttccacacc cctatatttc tattgcactc 6720
ccttttaact gttttttatt acaaaaatgc cctggaaaat gcactccctt tttgtgttg 6780 tttttttgtg aaacgatgtt gtcaggtaat ttatttgtca gtctactatg gtggcccatt 6840
atattaatag caactgtcgg tccaatagac gacgtcgatt ttctgcattt gtttaaccac 6900 gtggattta tgacatttta tattagttaa tttgtaaaac ctacccaatt aaagacctca 6960
tatgttctaa agactaatac ttaatgataa cattttctt ttagtgaaga aagggataat 7020
tagtaaatat ggaacaaggg cagaagattt attaaagccg cggtaagaga caacaagtag 7080
gtacgtggag tgtcttaggt gacttaccca cataacataa agtgacatta acaaacatag 7140
ctaatgctcc tatttgaata gtgcatatca gcataccta ttacatatag atagagcaa 7200 actctagcta gattgttgag cagatctcgg tgacgggcag gaccggacgg ggcggtaccg 7260
gcaggctgaa gtccagctgc cagaaaccca cgtcatgcca gttcccgtgc ttgaagccgg 7320
ccgcccgcag catgccgcgg ggggcatatc cgagcgcctc gtgcatgcgc acgctcgggt 7380
cgttgggcag cccgatgaca gcgaccacgc tcttgaagcc ctgtgcctcc agggacttca 7440
gcaggtgggt gtagagcgtg gagcccagtc ccgtccgctg gtggcggggg gagacgtaca 7500
cggtcgactc ggccgtccag tcgtaggcgt tgcgtgcctt caggggccc gcgtaggcga 7560 tgccggcgac ctcgccgtcc acctcggcga cgagccaggg atagcgctcc cgcagacgga 7620
cgaggtcgtc cgtccactcc tgcggttcct gcggctcggt acggaagttg accgtgcttg 7680
tctcgatgta gtggttgacg atggtgcaga ccgccggcat gtccgcctcg gtggcacggc 7740
ggatgtcggc cgggcgtcgt tctgggctca tggtagatcc cccgttcgta aatggtgaaa 7800
attttcagaa aattgctttt gctttaaaag aaatgattta aattgctgca atagaagtag 7860
aatgcttgat tgcttgagat tcgtttgttt tgtatatgtt gtgttgagaa ttaattctcg 7920
aggtcctctc caaatgaaat gaacttcctt atatagagga agggtcttgc gaaggatagt 7980
gggattgtgc gtcatccctt acgtcagtgg agatatcaca tcaatccact gctttgaag 8040 acgtggttgg aacgtcttct ttttccacga tgctcctcgt gggtgggggt ccatctttgg 8100
gaccactgtc ggtagaggca tcttgaacga tagcctttcc tttatcgcaa tgatggcatt 8160
tgtaggagcc accttccttt tccactatct tcacaataaa gtgacagata gctgggcaat 8220
ggaatccgag gaggtttccg gatattaccc tttgttgaaa agtctcaatt gcccttggt 8280 cttctgagac tgtatctttg atatttttgg agtagacaag tgtgtcgtgc tccaccatgt 8340
tatcacatca atccacttgc tttgaagacg tggttggaac gtcttctttt tccacgatgc 8400
tcctcgtggg tggggtcca tctttgggac cactgtcggc agaggcatct tcaacgatgg 8460
cctttccttt atcgcaatga tggcatttgt aggagccacc ttccttttcc actatcttca 8520
caataaagtg acagatagct gggcaatgga atccgaggag gtttccggat tacccttt 8580 gttgaaaagt ctcaattgcc ctttggtctt ctgagactgt atctttgata tttttgagt 8640 agacaagtgt gtcgtgctcc accatgttga cctgcaggtc gacacctggc acatcgtatc 8700
ttatctcttt tgtcgtttcc aacacaccac aacacaccta caaacgtgtc aattcacact 8760
tcaccaattt catttccttt tagtcaatca tattaaaagt agtagccccc acccccattt 8820
gttacctacc atttcccact ttaataatca cccacgctat gtccacttgt acttttgttt 8880
gcacacaact cttcccataa aatatcaaac caaatttttt ttagtggaaa acaaattccc 8940
caaatagaat actaacgaaa ttcatcgcat cagaatacac tcatctctga acagtggcga 9000
agcttgacgt tttcgacggg gggtcggaaa acgtatgtac ccgaaatttc tatagaatcg 9060
gggggtcgaa aacgtatata cccaaaattt ctatacgaaa actacatata taacactact 9120
gagcaaaaag ttcgggggtt cgggcgcccc tcccggcccc ttcaaagctt cgccaatgtc 9180
tctgaaccga agaaaaccct cactcgtcta ctagccaatg aatcctcacc agggaaaacc 9240
ctcactcgtc ttactggact attggcgctt ccaaatggac tacttgcgaa attcaccaca 9300
ttgggataca ctcgtctact gcggtgaggt aaaacccgct tggttcaagg atcgaactag 9360
cgattgctgc ctactcgcct aatctcccat catcaacagg tgccgccgaa acaaaatgct 9420
gggggcggga gttgaaccta ggtccagtga cgcacccatg aatttttttt ctagggatgc 9480
gaacgagtgg tttaaccata cttttaagag gtgcgatcgg aaattttacc tataaaatac 9540
actaaaaaag ttccaagggt ccacccaccc cttaacctaa gtccgccttt gtctggatca 9600
cgtgaaacat caggtctctc ccttaccagt ccagctacga ctcattgaca aaatatcaaa 9660
accatatgat tttgagtttt atctcaaccg aaagtgacat catgacagag aatcgacata 9720
accaaaacgt gtaaacgtac aactcaccat tgcgttgaaa aggacaaaac aggtaggatt 9780
cttgtcaaat tcaacgcgta cacctgtgct tcatctaaac cccatacttt taagaacctt 9840
tataaagacc actcactata tatacacata tataatatca cttatcaaac cctcggatcc 9900
accatgtctc ttcaacaagt aacaaccacc aggaagaacc gaaacgaggg gcggagacga 9960
tttaccgaca aacaaataag tttcctagag tacatgtttg agacacagtc gagacccgag 10020
ttaaggatga aacaccagtt ggcacataaa ctcgggcttc atcctcgtca agtggcgata 10080
tggttccaga acaaacgcgc gcgatcaaag tcgaggcaga ttgagcaaga gtataacgcg 10140
ctaaagcata actacgagac gcttgcgtct aaatccgagt ctctaaagaa agagaatcag 10200
gccctactca atcaattgga ggtgctgaga aatgtagccg aaaagcatca agagaaaact 10260
agtagtagtg gcagcggtga agaatcggat gatcggttta cgaactctcc ggacgtttatg 10320 tttggtcaag aaatgaatgt tccgttttgc gacggttttg cgtaccttga agaaggaaac 10380 agttgttgg agattgaaga acaactgcca gaccttcaaa agtggtggga gttctaagag 10440
ctcgaatttc cccgatcgtt caaacatttg gcaataaagt ttcttaagat tgaatcctgt 10500
tgccggtctt gcgatgatta tcatataatt tctgttgaat tacgttaagc atgtaataat 10560
taacatgtaa tgcatgacgt tatttatgag atgggttttt atgattagag tcccgcaatt 10620
atacatttaa tacgcgatag aaaacaaaat atagcgcgca aactaggata aattatcgcg 10680
cgcggtgtca tctatgttac tagatcggga attcgtaatc atgtcatagc tgtttcctgt 10740
gtgaaattgt tatccgctca caattccaca caacatacga gccggaagca taagtgtaa 10800 agcctggggt gcctaatgag tgagctaact cacattaatt gcgttgcgct cactgcccgc 10860
tttccagtcg ggaaacctgt cgtgccagct gcattaatga atcggccaac gcgcggggag 10920
aggcggtttg cgtattggag cttgagcttg gatcagattg tcgtttcccg ccttcagttt 10980
aaactatcag tgtttgacag gatatattgg cgggtaaacc taagagaaaa gagcgtttat 11040
tagaataatc ggatatttaa aagggcgtga aaaggtttat ccgttcgtcc atttgtatgt 11100
gcatgccaac cacagggttc ccctcgggat caa 11133

SEQUENCE LISTING

<160> NUMBER OF SEQ ID NOS: 43

<210> SEQ ID NO 1
<211> LENGTH: 4623
<212> TYPE: DNA
<213> ORGANISM: Artificial Sequence
<220> FEATURE:
<223> OTHER INFORMATION: Insert and flanking regions

<400> SEQUENCE: 1

```
tggcaggata tattgtggtg taaacaaatt gacgcttaga caacttaata acacattgcg    60
gacgttttta atgtactgaa ttaacgccga attgctctag cattcgccat tcaggctgcg   120
caactgttgg gaagggcgat cggtgcgggc ctcttcgcta ttacgccagc tggcgaaagg   180
gggatgtgct gcaaggcgat taagttgggt aacgccaggg ttttcccagt cacgacgttg   240
taaaacgacg gccagtgcca agctaattcg cttcaagacg tgctcaaatc actatttcca   300 caccccctata tttctattgc actccctttt aactgttttt tattacaaaa atgccctgga   360
aaatgcactc cctttttgtg tttgtttttt tgtgaaacga tgttgtcagg taatttattt   420
gtcagtctac tatggtggcc cattatatta atagcaactg tcggtccaat agacgacgtc   480
gattttctgc atttgtttaa ccacgtggat tttatgacat tttatattag ttaatttgta   540
aaacctaccc aattaaagac ctcatatgtt ctaaagacta atacttaatg ataacaattt   600
tcttttagtg aagaaaggga taattagtaa atatggaaca agggcagaag atttattaaa   660
gccgcggtaa gagacaacaa gtaggtacgt ggagtgtctt aggtgactta cccacataac   720
ataaagtgac attaacaaac atagctaatg ctcctatttg aatagtgcat atcagcatac   780
cttattacat atagatagga gcaaactcta gctagattgt tgagcagatc tcggtgacgg   840
gcaggaccgg acggggcggt accggcaggc tgaagtccag ctgccagaaa cccacgtcat   900
gccagttccc gtgcttgaag ccggccgccc gcagcatgcc gcgggggca tatccgagcg    960 cctcgtgcat gcgcacgctc gggtcgttgg gcagcccgat gacagcgacc acgtctcttga  1020 agccctgtgc ctccagggac ttcagcaggt gggtgtagag cgtggagccc agtcccgtcc  1080
gctggtggcg gggggagacg tacacggtcg actcggccgt ccagtcgtag gcgttgcgtg  1140
ccttccaggg gcccgcgtag gcgatgccgg cgacctcgcc gtccacctcg gcgacgagcc  1200
agggatagcg ctcccgcaga cggacgaggt cgtccgtcca ctcctgcggt tcctgcggct  1260
cggtacggaa gttgaccgtg cttgtctcga tgtagtggtt gacgatggtg cagaccgccg  1320
gcatgtccgc ctcggtggca cggcggatgt cggccgggcg tcgttctggg ctcatggtag  1380
atcccccgtt cgtaaatggt gaaaattttc agaaaattgc ttttgcttta aaagaaatga  1440
tttaaattgc tgcaatagaa gtagaatgct tgattgcttg agattcgttt gttttgtata  1500
tgttgtgttg agaattaatt ctcgaggtcc tctccaaatg aaatgaactt ccttatatag  1560
aggaagggtc ttgcgaagga tagtgggatt gtgcgtcatc ccttacgtca gtggagatat  1620
cacatcaatc cacttgcttt gaagacgtgg ttggaacgtc ttcttttttcc acgatgctcc  1680 tcgtgggtgg gggtccatct ttgggaccac tgtcggtaga ggcatcttga acgatagcct  1740
ttcctttatc gcaatgatgg catttgtagg agccaccttc cttttccact atcttcacaa  1800
taaagtgaca gatagctggg caatggaatc cgaggaggtt tccggatatt acccttttgtt 1860 gaaaagtctc aattgccctt tggtcttctg agactgtatc tttgatattt ttggagtaga  1920
caagtgtgtc gtgctccacc atgttatcac atcaatccac ttgctttgaa gacgtggttg   1980
gaacgtcttc ttttttccacg atgctcctcg tgggtgggggg tccatctttg gaccactgt   2040 cggcagaggc atcttcaacg atggcctttc ctttatcgca atgatggcat ttgtaggagc   2100
caccttcctt ttccactatc ttcacaataa agtgacagat agctgggcaa tggaatccga   2160 ggaggttttcc ggatattacc ctttgttgaa aagtctcaat tgccctttgg tcttctgaga   2220
ctgtatcttt gatattttttg gagtagacaa gtgtgtcgtg ctccaccatg ttgacctgca   2280
```

```
ggtcgacacc tggcacatcg tatcttatct cttttgtcgt ttccaacaca ccacaacaca    2340
cctacaaacg tgtcaattca cacttcacca atttcatttc cttttagtca atcatattaa    2400
aagtagtagc ccccaccccc atttgttacc taccatttcc cactttaata atcacccacg    2460
ctatgtccac ttgtactttt gtttgcacac aactcttccc ataaaatatc aaaccaaatt    2520
ttttttagtg gaaaacaaat tccccaaata gaatactaac gaaattcatc gcatcagaat    2580
acactcatct ctgaacagtg gcgaagcttg acgttttcga cgggggtcg gaaaacgtat     2640 gtacccgaaa tttctataga atcgggggt cgaaaacgta tatacccaaa atttctatac     2700
gaaaactaca tatataacac tactgagcaa aaagttcggg ggttcgggcg ccctcccgg     2760 cccccttcaaa gcttcgccaa tgtctctgaa ccgaagaaaa ccctcactcg tctactagcc   2820
aatgaatcct caccagggaa acccctcact cgtcttactg gactattggc gcttccaaat    2880
ggactacttg cgaaattcac cacattggga tacactcgtc tactgcggtg aggtaaaacc    2940
cgcttggttc aaggatcgaa ctagcgattg ctgcctactc gcctaatctc ccatcatcaa    3000
caggtgccgc cgaaacaaaa tgctgggggc gggagttgaa cctaggtcca gtgacgcacc    3060
catgaatttt ttttctaggg atgcgaacga gtggtttaac catacttta agaggtgcga     3120 tcggaaattt tacctataaa atacactaaa aaagttccaa gggtccaccc acccttaac    3180 ctaagtccgc ctttgtctgg atcacgtgaa acatcaggtc tctcccttac cagtccagct    3240
acgactcatt gacaaaatat caaaaccata tgattttgag ttttatctca accgaaagtg    3300
acatcatgac agagaatcga cataaccaaa acgtgtaaac gtacaactca ccattgcgtt    3360
gaaaaggaca aaacaggtag gattcttgtc aaattcaacg cgtacacctg tgcttcatct    3420
aaaccccata cttttaagaa cctttataaa gaccactcac tatatataca catatataat    3480
atcacttatc aaaccctcgg atccaccatg tctcttcaac aagtaacaac caccaggaag    3540
aaccgaaacg aggggcggag acgatttacc gacaaacaaa taagtttcct agagtacatg    3600
tttgagacac agtcgagacc cgagttaagg atgaaacacc agttggcaca taaactcggg    3660
cttcatcctc gtcaagtggc gatatggttc cagaacaaac gcgcgcgatc aaagtcgagg    3720
cagattgagc aagagtataa cgcgctaaag cataactacg agacgcttgc gtctaaatcc    3780
gagtctctaa agaaagagaa tcaggcccta ctcaatcaat tggaggtgct gagaaatgta    3840
gccgaaaagc atcaagagaa aactagtagt agtggcagcg gtgaagaatc ggatgatcgg    3900
tttacgaact ctccggacgt tatgtttggt caagaaatga atgttccgtt ttgcgacggt    3960
tttgcgtacc ttgaagaagg aaacagtttg ttggagattg aagaacaact gccagacctt    4020
caaaagtggt gggagttcta agagctcgaa ttttccccgat cgttcaaaca tttggcaata   4080
aagtttctta agattgaatc ctgttgccgg tcttgcgatg attatcatat aatttctgtt    4140
gaattacgtt aagcatgtaa taattaacat gtaatgcatg acgttattta tgagatgggt    4200
ttttatgatt agagtcccgc aattatacat ttaatacgcg atagaaaaca aaatatagcg    4260
cgcaaactag gataaattat cgcgcgcggt gtcatctatg ttactagatc gggaattcgt    4320
aatcatgtca tagctgtttc ctgtgtgaaa ttgttatccg ctcacaattc cacacaacat    4380
acgagccgga agcataaagt gtaaagcctg gggtgcctaa tgagtgagct aactcacatt    4440
aattgcgttg cgctcactgc ccgctttcca gtcgggaaac ctgtcgtgcc agctgcatta    4500
atgaatcggc caacgcgcgg ggagaggcgg tttgcgtatt ggagcttgag cttggatcag    4560
attgtcgttt cccgccttca gtttaaacta tcagtgtttg acaggatata ttggcgggta    4620
aac                                                                  4623
```

```
<210> SEQ ID NO 2
<211> LENGTH: 139
<212> TYPE: DNA
<213> ORGANISM: Artificial Sequence
<220> FEATURE:
<223> OTHER INFORMATION: Right Junction Sequence

<400> SEQUENCE: 2
tgacaggata tattggcggg taaacctaag agaaagagc gtttattaga ataatcggat      60
atttaaaagg gcgtgaaaag gtttatccgt tcgtccattt gtatgtgcat gccaaccaca     120
gggttcccct cgggatcaa                                                  139

<210> SEQ ID NO 3
<211> LENGTH: 268
<212> TYPE: DNA
<213> ORGANISM: Artificial Sequence
<220> FEATURE:
<223> OTHER INFORMATION: Left Junction Sequence

<400> SEQUENCE: 3
cgaattgatc acaggcagca acgctctgtc atcgttacaa tcaacatgct accctccgcg      60
agatcatccg tgtttcaaac ccggcagctt agttgccgtt cttccgaata gcatcggtaa     120
catgagcaaa gtctgccgcc ttacaacggc tctcccgctg acgccgtccc ggactgatgg     180
gctgcctgta tcgagtggtg attttgtgcc gagctgccgg tcggggagct gttggctggc     240
tggtggcagg atatattgtg gtgtaaac                                        268

<210> SEQ ID NO 4
<211> LENGTH: 4573
<212> TYPE: DNA
<213> ORGANISM: Artificial Sequence
<220> FEATURE:
<223> OTHER INFORMATION: Insert Sequence

<400> SEQUENCE: 4
aaattgacgc ttagacaact taataacaca ttgcggacgt ttttaatgta ctgaattaac      60
gccgaattgc tctagcattc gccattcagg ctgcgcaact gttgggaagg gcgatcggtg     120
cgggcctctt cgctattacg ccagctggcg aaagggggat gtgctgcaag gcgattaagt     180
tgggtaacgc cagggttttc ccagtcacga cgttgtaaaa cgacggccag tgccaagcta     240
attcgcttca agacgtgctc aaatcactat ttccacaccc ctatatttct attgcactcc     300
cttttaactg tttttttatta caaaaatgcc ctggaaaatg cactcccttt tgtgtttgt     360 tttttttgtga acgatgttg tcaggtaatt tatttgtcag tctactatgg tggcccatta     420
tattaatagc aactgtcggt ccaatagacg acgtcgattt tctgcatttg tttaaccacg     480
tggattttat gacattttat attagttaat ttgtaaaacc tacccaatta aagacctcat     540
atgttctaaa gactaatact taatgataac aattttcttt tagtgaagaa agggataatt     600
agtaaatatg gaacaagggc agaagattta ttaaagccgc ggtaagagac aacaagtagg     660
tacgtggagt gtcttaggtg acttacccac ataacataaa gtgacattaa caaacatagc     720
taatgctcct atttgaatag tgcatatcag catacctttat tacatataga taggagcaaa     780
ctctagctag attgttgagc agatctcggt gacgggcagg accggacggg gcggtaccgg     840
caggctgaag tccagctgcc agaaacccac gtcatgccag ttcccgtgct tgaagccggc     900
cgcccgcagc atgccgcggg gggcatatcc gagcgcctcg tgcatgcgca cgctcgggtc     960
```

```
gttgggcagc cgatgacag cgaccacgct cttgaagccc tgtgcctcca gggacttcag    1020
caggtgggtg tagagcgtgg agcccagtcc cgtccgctgg tggcggggggg agacgtacac    1080 ggtcgactcg gccgtccagt cgtaggcgtt gcgtgccttc caggggcccg cgtaggcgat    1140
gccggcgacc tcgccgtcca cctcggcgac gagccaggga tagcgctccc gcagacggac    1200
gaggtcgtcc gtccactcct gcggttcctg cggctcggta cggaagttga ccgtgcttgt    1260
ctcgatgtag tggttgacga tggtgcagac cgccggcatg tccgcctcgg tggcacggcg    1320
gatgtcggcc gggcgtcgtt ctgggctcat ggtagatccc ccgttcgtaa atggtgaaaa    1380
ttttcagaaa attgcttttg ctttaaaaga aatgatttaa attgctgcaa tagaagtaga    1440
atgcttgatt gcttgagatt cgtttgtttt gtatatgttg tgttgagaat taattctcga    1500
ggtcctctcc aaatgaaatg aacttcctta tatagaggaa gggtcttgcg aaggatagtg    1560
ggattgtgcg tcatccctta cgtcagtgga gatatcacat caatccactt gctttgaaga    1620
cgtggttgga acgtcttctt tttccacgat gctcctcgtg ggtggggtc catctttggg    1680 accactgtcg gtagaggcat cttgaacgat agcctttcct ttatcgcaat gatggcattt    1740
gtaggagcca ccttcctttt ccactatctt cacaataaag tgacagatag ctgggcaatg    1800
gaatccgagg aggtttccgg atattaccct ttgttgaaaa gtctcaattg ccctttggtc    1860
ttctgagact gtatctttga tatttttgga gtagacaagt gtgtcgtgct ccaccatgtt    1920
atcacatcaa tccacttgct ttgaagacgt ggttggaacg tcttcttttt ccacgatgct    1980
cctcgtgggt gggggtccat ctttgggacc actgtcggca gaggcatctt caacgatggc    2040 cttccctttta tcgcaatgat ggcatttgta ggagccacct tccttttcca ctatcttcac    2100
aataaagtga cagatagctg gcaatggaa tccgaggagg tttccggata ttacccttg    2160 ttgaaaagtc tcaattgccc tttggtcttc tgagactgta tctttgatat ttttggagta    2220
gacaagtgtg tcgtgctcca ccatgttgac ctgcaggtcg acacctggca catcgtatct    2280
tatctctttt gtcgtttcca acacaccaca acacacctac aaacgtgtca attcacactt    2340
caccaatttc atttccttt agtcaatcat attaaaagta gtagccccca cccccatttg    2400
ttacctacca tttcccactt taataatcac ccacgctatg tccacttgta cttttgtttg    2460
cacacaactc ttcccataaa atatcaaacc aaatttttt tagtggaaaa caaattcccc    2520
aaatagaata ctaacgaaat tcatcgcatc agaatacact catctctgaa cagtggcgaa    2580
gcttgacgtt ttcgacgggg ggtcggaaaa cgtatgtacc cgaaatttct atagaatcgg    2640
ggggtcgaaa acgtatatac ccaaaatttc tatacgaaaa ctacatatat aacactactg    2700
agcaaaaagt tcgggggttc gggcgcccct cccggcccct tcaaagcttc gccaatgtct    2760
ctgaaccgaa gaaaaccctc actcgtctac tagccaatga atcctcacca gggaaaaccc    2820
tcactcgtct tactggacta ttggcgcttc caaatggact acttgcgaaa ttcaccacat    2880
tgggatacac tcgtctactg cggtgaggta aaacccgctt ggttcaagga tcgaactagc    2940
gattgctgcc tactcgccta atctcccatc atcaacaggt gccgcgaaa caaaatgctg    3000 ggggcgggag ttgaacctag gtccagtgac gcacccatga atttttttc tagggatgcg    3060 aacgagtggt ttaaccatac ttttaagagg tgcgatcgga aattttacct ataaaataca    3120
ctaaaaaagt tccaagggtc cacccacccc ttaacctaag tccgcctttg tctggatcac    3180
gtgaaacatc aggtctctcc cttaccagtc cagctacgac tcattgacaa aatatcaaaa    3240
ccatatgatt ttgagtttta tctcaaccga aagtgacatc atgacagaga atcgacataa    3300
ccaaaacgtg taaacgtaca actcaccatt gcgttgaaaa ggacaaaaca ggtaggattc    3360
```

```
ttgtcaaatt caacgcgtac acctgtgctt catctaaacc ccatactttt aagaaccttt    3420
ataaagacca ctcactatat atacacatat ataatatcac ttatcaaacc ctcggatcca    3480
ccatgtctct tcaacaagta acaaccacca ggaagaaccg aaacgagggg cggagacgat    3540
ttaccgacaa acaaataagt ttcctagagt acatgtttga cacacagtcg agacccgagt    3600
taaggatgaa acaccagttg gcacataaac tcgggcttca tcctcgtcaa gtggcgatat    3660
ggttccagaa caaacgcgcg cgatcaaagt cgaggcagat tgagcaagag tataacgcgc    3720
taaagcataa ctacgagacg cttgcgtcta aatccgagtc tctaaagaaa gagaatcagg    3780
ccctactcaa tcaattggag gtgctgagaa atgtagccga aaagcatcaa gagaaaacta    3840
gtagtagtgg cagcggtgaa gaatcggatg atcggtttac gaactctccg gacgttatgt    3900
ttggtcaaga aatgaatgtt ccgttttgcg acggttttgc gtaccttgaa gaaggaaaca    3960
gtttgttgga gattgaagaa caactgccag accttcaaaa gtggtgggag ttctaagagc    4020
tcgaatttcc ccgatcgttc aaacatttgg caataaagtt tcttaagatt gaatcctgtt    4080
gccggtcttg cgatgattat catataattt ctgttgaatt acgttaagca tgtaataatt    4140
aacatgtaat gcatgacgtt atttatgaga tgggttttta tgattagagt cccgcaatta    4200
tacatttaat acgcgataga aaacaaaata tagcgcgcaa actaggataa attatcgcgc    4260
gcggtgtcat ctatgttact agatcgggaa ttcgtaatca tgtcatagct gtttcctgtg    4320
tgaaattgtt atccgctcac aattccacac aacatacgag ccggaagcat aaagtgtaaa    4380
gcctggggtg cctaatgagt gagctaactc acattaattg cgttgcgctc actgcccgct    4440
ttccagtcgg gaaacctgtc gtgccagctg cattaatgaa tcggccaacg cgcggggaga    4500
ggcggtttgc gtattggagc ttgagcttgg atcagattgt cgtttcccgc cttcagttta    4560
aactatcagt gtt                                                      4573

<210> SEQ ID NO 5
<211> LENGTH: 20
<212> TYPE: DNA
<213> ORGANISM: Artificial Sequence
<220> FEATURE:
<223> OTHER INFORMATION: Primer 750

<400> SEQUENCE: 5
acgcaactga actcagacca                                               20

<210> SEQ ID NO 6
<211> LENGTH: 20
<212> TYPE: DNA
<213> ORGANISM: Artificial Sequence
<220> FEATURE:
<223> OTHER INFORMATION: Primer 751

<400> SEQUENCE: 6
aagtggcgat atggttccag                                               20

<210> SEQ ID NO 7
<211> LENGTH: 20
<212> TYPE: DNA
<213> ORGANISM: Artificial Sequence
<220> FEATURE:
<223> OTHER INFORMATION: Primer 752

<400> SEQUENCE: 7
ggctgcaagt tttggtcaat                                               20
```

```
<210> SEQ ID NO 8
<211> LENGTH: 20
<212> TYPE: DNA
<213> ORGANISM: Artificial Sequence
<220> FEATURE:
<223> OTHER INFORMATION: Primer 753

<400> SEQUENCE: 8
ttcggctaca tttctcagca                                                   20

<210> SEQ ID NO 9
<211> LENGTH: 20
<212> TYPE: DNA
<213> ORGANISM: Artificial Sequence
<220> FEATURE:
<223> OTHER INFORMATION: Primer 754

<400> SEQUENCE: 9
agccaatgaa tcctcaccag                                                   20

<210> SEQ ID NO 10
<211> LENGTH: 20
<212> TYPE: DNA
<213> ORGANISM: Artificial Sequence
<220> FEATURE:
<223> OTHER INFORMATION: Primer 755

<400> SEQUENCE: 10
attaggcgag taggcagcaa                                                   20

<210> SEQ ID NO 11
<211> LENGTH: 22
<212> TYPE: DNA
<213> ORGANISM: Artificial Sequence
<220> FEATURE:
<223> OTHER INFORMATION: Primer 756

<400> SEQUENCE: 11
caacacacct acaaacgtgt ca                                                22

<210> SEQ ID NO 12
<211> LENGTH: 20
<212> TYPE: DNA
<213> ORGANISM: Artificial Sequence
<220> FEATURE:
<223> OTHER INFORMATION: Primer 757

<400> SEQUENCE: 12
gggtgggggc tactactttt                                                   20

<210> SEQ ID NO 13
<211> LENGTH: 21
<212> TYPE: DNA
<213> ORGANISM: Artificial Sequence
<220> FEATURE:
<223> OTHER INFORMATION: Primer 758

<400> SEQUENCE: 13
cttcagcagg tgggtgtaga g                                                 21

<210> SEQ ID NO 14
<211> LENGTH: 20
<212> TYPE: DNA
<213> ORGANISM: Artificial Sequence
<220> FEATURE:
<223> OTHER INFORMATION: Primer 759
```

```
<400> SEQUENCE: 14
agtcgaccgt gtacgtctcc                                                    20

<210> SEQ ID NO 15
<211> LENGTH: 20
<212> TYPE: DNA
<213> ORGANISM: Artificial Sequence
<220> FEATURE:
<223> OTHER INFORMATION: Primer 760

<400> SEQUENCE: 15
gttgggtcag cctgagtgat                                                    20

<210> SEQ ID NO 16
<211> LENGTH: 24
<212> TYPE: DNA
<213> ORGANISM: Artificial Sequence
<220> FEATURE:
<223> OTHER INFORMATION: Primer 2527

<400> SEQUENCE: 16
cgcttgcgtc taaatccgag tctc                                               24

<210> SEQ ID NO 17
<211> LENGTH: 20
<212> TYPE: DNA
<213> ORGANISM: Artificial Sequence
<220> FEATURE:
<223> OTHER INFORMATION: Primer 203

<400> SEQUENCE: 17
caagaccggc aacaggattc                                                    20

<210> SEQ ID NO 18
<211> LENGTH: 20
<212> TYPE: DNA
<213> ORGANISM: Artificial Sequence
<220> FEATURE:
<223> OTHER INFORMATION: Primer 378

<400> SEQUENCE: 18
atatggcgct gatctctgct                                                    20

<210> SEQ ID NO 19
<211> LENGTH: 20
<212> TYPE: DNA
<213> ORGANISM: Artificial Sequence
<220> FEATURE:
<223> OTHER INFORMATION: Primer 1970

<400> SEQUENCE: 19
ggcggtctgc accatcgtca                                                    20

<210> SEQ ID NO 20
<211> LENGTH: 24
<212> TYPE: DNA
<213> ORGANISM: Artificial Sequence
<220> FEATURE:
<223> OTHER INFORMATION: Primer 1747

<400> SEQUENCE: 20
aagacgacca tcgcaaccca tcta                                               24

<210> SEQ ID NO 21
```

```
<211> LENGTH: 24
<212> TYPE: DNA
<213> ORGANISM: Artificial Sequence
<220> FEATURE:
<223> OTHER INFORMATION: Primer 1748

<400> SEQUENCE: 21
tagccttcca tccgtgacct caat                                          24

<210> SEQ ID NO 22
<211> LENGTH: 24
<212> TYPE: DNA
<213> ORGANISM: Artificial Sequence
<220> FEATURE:
<223> OTHER INFORMATION: Primer 1745

<400> SEQUENCE: 22
agctgattgg atgtaccgcg agat                                          24

<210> SEQ ID NO 23
<211> LENGTH: 24
<212> TYPE: DNA
<213> ORGANISM: Artificial Sequence
<220> FEATURE:
<223> OTHER INFORMATION: Primer 1746

<400> SEQUENCE: 23
ttcaaatcgt actccggcag gtca                                          24

<210> SEQ ID NO 24
<211> LENGTH: 24
<212> TYPE: DNA
<213> ORGANISM: Artificial Sequence
<220> FEATURE:
<223> OTHER INFORMATION: Primer 822

<400> SEQUENCE: 24
atcaaacatc gacccacggc gtaa                                          24

<210> SEQ ID NO 25
<211> LENGTH: 24
<212> TYPE: DNA
<213> ORGANISM: Artificial Sequence
<220> FEATURE:
<223> OTHER INFORMATION: Primer 1127

<400> SEQUENCE: 25
gatcaattcg ggcacgaacc cagt                                          24

<210> SEQ ID NO 26
<211> LENGTH: 21
<212> TYPE: DNA
<213> ORGANISM: Artificial Sequence
<220> FEATURE:
<223> OTHER INFORMATION: Primer 817

<400> SEQUENCE: 26
gcaactgaac tcagaccact g                                             21

<210> SEQ ID NO 27
<211> LENGTH: 20
<212> TYPE: DNA
<213> ORGANISM: Artificial Sequence
<220> FEATURE:
<223> OTHER INFORMATION: Primer 27
```

```
<400> SEQUENCE: 27
gagcttgagc ttggatcaga                                            20

<210> SEQ ID NO 28
<211> LENGTH: 25
<212> TYPE: DNA
<213> ORGANISM: Artificial Sequence
<220> FEATURE:
<223> OTHER INFORMATION: Probe 819

<400> SEQUENCE: 28
ttgtcgtttc ccgccttcag tttaa                                      25

<210> SEQ ID NO 29
<211> LENGTH: 23
<212> TYPE: DNA
<213> ORGANISM: Artificial Sequence
<220> FEATURE:
<223> OTHER INFORMATION: Primer 868

<400> SEQUENCE: 29
ccgcaatgtg ttattaagtt gtc                                        23

<210> SEQ ID NO 30
<211> LENGTH: 20
<212> TYPE: DNA
<213> ORGANISM: Artificial Sequence
<220> FEATURE:
<223> OTHER INFORMATION: Primer 752

<400> SEQUENCE: 30
ggctgcaagt tttggtcaat                                            20

<210> SEQ ID NO 31
<211> LENGTH: 19
<212> TYPE: DNA
<213> ORGANISM: Artificial Sequence
<220> FEATURE:
<223> OTHER INFORMATION: Primer 530

<400> SEQUENCE: 31
cgccacttga cgaggatga                                             19

<210> SEQ ID NO 32
<211> LENGTH: 24
<212> TYPE: DNA
<213> ORGANISM: Artificial Sequence
<220> FEATURE:
<223> OTHER INFORMATION: Primer 531

<400> SEQUENCE: 32
cgagacccga gttaaggatg aaac                                       24

<210> SEQ ID NO 33
<211> LENGTH: 25
<212> TYPE: DNA
<213> ORGANISM: Artificial Sequence
<220> FEATURE:
<223> OTHER INFORMATION: Probe 532

<400> SEQUENCE: 33
agcccgagtt tatgtgccaa ctggt                                      25

<210> SEQ ID NO 34
```

```
<211> LENGTH: 22
<212> TYPE: DNA
<213> ORGANISM: Artificial Sequence
<220> FEATURE:
<223> OTHER INFORMATION: Primer 527

<400> SEQUENCE: 34
ctgcaccatc gtcaaccact ac                                                  22

<210> SEQ ID NO 35
<211> LENGTH: 19
<212> TYPE: DNA
<213> ORGANISM: Artificial Sequence
<220> FEATURE:
<223> OTHER INFORMATION: Primer 528

<400> SEQUENCE: 35
ggtcgtccgt ccactcctg                                                      19

<210> SEQ ID NO 36
<211> LENGTH: 24
<212> TYPE: DNA
<213> ORGANISM: Artificial Sequence
<220> FEATURE:
<223> OTHER INFORMATION: Probe 529

<400> SEQUENCE: 36
tcgagacaag cacggtcaac ttcc                                                24

<210> SEQ ID NO 37
<211> LENGTH: 20
<212> TYPE: DNA
<213> ORGANISM: Artificial Sequence
<220> FEATURE:
<223> OTHER INFORMATION: Primer 718

<400> SEQUENCE: 37
ctactgacca gcaaggcaaa                                                     20

<210> SEQ ID NO 38
<211> LENGTH: 20
<212> TYPE: DNA
<213> ORGANISM: Artificial Sequence
<220> FEATURE:
<223> OTHER INFORMATION: Primer 719

<400> SEQUENCE: 38
tcacaatagc gtctccttgg                                                     20

<210> SEQ ID NO 39
<211> LENGTH: 21
<212> TYPE: DNA
<213> ORGANISM: Artificial Sequence
<220> FEATURE:
<223> OTHER INFORMATION: Probe 720

<400> SEQUENCE: 39
tcgtgccgaa gcaaccaaac a                                                   21

<210> SEQ ID NO 40
<211> LENGTH: 23
<212> TYPE: DNA
<213> ORGANISM: Artificial Sequence
<220> FEATURE:
<223> OTHER INFORMATION: Primer 934
```

```
<400> SEQUENCE: 40
agaccactga aatagagaga aag                                             23

<210> SEQ ID NO 41
<211> LENGTH: 24
<212> TYPE: DNA
<213> ORGANISM: Artificial Sequence
<220> FEATURE:
<223> OTHER INFORMATION: Primer 935

<400> SEQUENCE: 41
ggagttctga taattgttat cgtc                                            24

<210> SEQ ID NO 42
<211> LENGTH: 24
<212> TYPE: DNA
<213> ORGANISM: Artificial Sequence
<220> FEATURE:
<223> OTHER INFORMATION: Probe 936

<400> SEQUENCE: 42
tgaagtgaga tgattgaggg tggg                                            24

<210> SEQ ID NO 43
<211> LENGTH: 11133
<212> TYPE: DNA
<213> ORGANISM: Artificial Sequence
<220> FEATURE:
<223> OTHER INFORMATION: DNA plasmid

<400> SEQUENCE: 43
agtactttga tccaacccct ccgctgctat agtgcagtcg gcttctgacg ttcagtgcag     60
ccgtcttctg aaaacgacat gtcgcacaag tcctaagtta cgcgacaggc tgccgccctg    120 ccctttttcct ggcgttttct tgtcgcgtgt tttagtcgca taaagtagaa tacttgcgac   180
tagaaccgga gacattacgc catgaacaag agcgccgccg ctggcctgct gggctatgcc    240
cgcgtcagca ccgacgacca ggacttgacc aaccaacggg ccgaactgca cgcggccggc    300
tgcaccaagc tgtttttccga agatcacc ggcaccaggc gcgaccgccc ggagctggcc    360
aggatgcttg accacctacg ccctggcgac gttgtgacag tgaccaggct agaccgcctg    420
gcccgcagca cccgcgacct actggacatt gccgagcgca tccaggaggc cggcgcgggc    480
ctgcgtagcc tggcagagcc gtgggccgac accaccacgc cggccggccg catggtgttg    540
accgtgttcg ccggcattgc cgagttcgag cgttccctaa tcatcgaccg cacccggagc    600
gggcgcgagg ccgccaaggc ccgaggcgtg aagtttggcc ccgccctac cctcaccccg     660 gcacagatcg cgcacgcccg cgagctgatc gaccaggaag gccgcaccgt gaaagaggcg    720
gctgcactgc ttggcgtgca tcgctcgacc ctgtaccgcg cacttgagcg cagcgaggaa    780
gtgacgccca ccgaggccag gcggcgcggt gccttccgtg aggacgcatt gaccgaggcc    840
gacgccctgg cggccgccga gaatgaacgc caagaggaac aagcatgaaa ccgcaccagg    900
acggccagga cgaaccgttt ttcattaccg aagagatcga ggcggagatg atcgcggccg    960
ggtacgtgtt cgagccgccc gcgcacgtct caaccgtgcg gctgcatgaa atcctggccg   1020
gtttgtctga tgccaagctg gcggcctggc cggccagctt ggccgctgaa gaaaccgagc   1080
gccgccgtct aaaaaggtga tgtgtatttg agtaaaacag cttgcgtcat gcggtcgctg   1140
cgtatatgat gcgatgagta aataaacaaa tacgcaaggg gaacgcatga aggttatcgc   1200
```

-continued

```
tgtacttaac cagaaaggcg ggtcaggcaa gacgaccatc gcaacccatc tagcccgcgc   1260
cctgcaactc gccggggccg atgttctgtt agtcgattcc gatccccagg gcagtgcccg   1320
cgattgggcg gccgtgcggg aagatcaacc gctaaccgtt gtcggcatcg accgcccgac   1380
gattgaccgc gacgtgaagg ccatcggccg gcgcgacttc gtagtgatcg acggagcgcc   1440
ccaggcggcg gacttggctg tgtccgcgat caaggcagcc gacttcgtgc tgattccggt   1500
gcagccaagc ccttacgaca tatgggccac cgccgacctg gtggagctgg ttaagcagcg   1560
cattgaggtc acggatggaa ggctacaagc ggcctttgtc gtgtcgcggg cgatcaaagg   1620
cacgcgcatc ggcggtgagg ttgccgaggc gctggccggg tacgagctgc ccattcttga   1680
gtcccgtatc acgcagcgcg tgagctaccc aggcactgcc gccgccggca aaccgttct    1740
tgaatcagaa cccgagggcg acgctgcccg cgaggtccag gcgctggccg ctgaaattaa   1800
atcaaaactc atttgagtta atgaggtaaa gagaaaatga gcaaaagcac aaacacgcta   1860
agtgccggcc gtccgagcgc acgcagcagc aaggctgcaa cgttggccag cctggcagac   1920
acgccagcca tgaagcgggt caactttcag ttgccggcgg aggatcacac caagctgaag   1980
atgtacgcgg tacgccaagg caagaccatt accgagctgc tatctgaata catcgcgcag   2040
ctaccagagt aaatgagcaa atgaataaat gagtagatga ttttagcgg ctaaaggagg    2100
cggcatggaa aatcaagaac aaccaggcac cgacgccgtg gaatgcccca tgtgtggagg   2160
aacgggcggt tggccaggcg taagcggctg ggttgtctgc cggccctgca atggcactgg   2220
aacccccaag cccgaggaat cggcgtgagc ggtcgcaaac catccggccc ggtacaaatc   2280
ggcgcggcgc tgggtgatga cctggtggag aagttgaagg ccgcgcaggc cgcccagcgg   2340
caacgcatcg aggcagaagc acgcccggt gaatcgtggc aagcggccgc tgatcgaatc     2400
cgcaaagaat cccggcaacc gccggcagcc ggtgcgccgt cgattaggaa gccgcccaag   2460
ggcgacgagc aaccagattt tttcgttccg atgctctatg acgtgggcac ccgcgatagt   2520
cgcagcatca tggacgtggc cgttttccgt ctgtcgaagc gtgaccgacg agctggcgag   2580
gtgatccgct acgagcttcc agacgggcac gtagaggttt ccgcagggcc ggccggcatg   2640
gccagtgtgt gggattacga cctggtactg atggcggttt cccatctaac cgaatccatg   2700
aaccgatacc gggaagggaa gggagacaag cccggccgcg tgttccgtcc acacgttgcg   2760
gacgtactca agttctgccg gcgagccgat ggcggaaagc agaaagacga cctggtagaa   2820
acctgcattc ggttaaacac cacgcacgtt gccatgcagc gtacgaagaa ggccaagaac   2880
ggccgcctgg tgacggtatc cgagggtgaa gccttgatta ccgctacaa gatcgtaaag     2940
agcgaaaccg gcggccgga gtacatcgag atcgagctag ctgattggat gtaccgcgag    3000
atcacagaag gcaagaaccc ggacgtgctg acggttcacc ccgattactt tttgatcgat   3060
cccggcatcg gccgttttct ctaccgcctg gcacgccgcg ccgcaggcaa ggcagaagcc   3120
agatggttgt tcaagacgat ctacgaacgc agtggcagcg ccggagagtt caagaagttc   3180
tgtttcaccg tgcgcaagct gatcgggtca aatgacctgc cggagtacga tttgaaggag   3240
gaggcgggc aggctggccc gatcctagtc atgcgctacc gcaacctgat cgagggcgaa    3300
gcatccgccg gttcctaatg tacgagcag atgctagggc aaattgccct agcagggaa      3360
aaaggtcgaa aaggtctctt tcctgtggat agcacgtaca ttgggaaccc aaagccgtac   3420
attgggaacc ggaacccgta cattgggaac ccaaagccgt acattgggaa ccggtcacac   3480
atgtaagtga ctgatataaa agagaaaaaa ggcgatttt ccgcctaaaa ctctttaaaa     3540
cttattaaaa ctcttaaaac ccgcctggcc tgtgcataac tgtctggcca gcgcacagcc   3600
```

```
gaagagctgc aaaaagcgcc taccettcgg tcgctgcgct ccctacgccc cgccgcttcg   3660
cgtcggccta tcgcggccgc tggccgctca aaaatggctg gcctacggcc aggcaatcta   3720
ccagggcgcg acaagccgc gccgtcgcca ctcgaccgcc ggcgcccaca tcaaggcacc    3780
ctgcctcgcg cgtttcggtg atgacggtga aaacctctga cacatgcagc tcccggagac   3840
ggtcacagct tgtctgtaag cggatgccgg gagcagacaa gcccgtcagg gcgcgtcagc   3900
gggtgttggc gggtgtcggg gcgcagccat gacccagtca cgtagcgata gcggagtgta   3960
tactggctta actatgcggc atcagagcag attgtactga gagtgcacca tatgcggtgt   4020
gaaataccgc acagatgcgt aaggagaaaa taccgcatca ggcgctcttc cgcttcctcg   4080
ctcactgact cgctgcgctc ggtcgttcgg ctgcggcgag cggtatcagc tcactcaaag   4140
gcggtaatac ggttatccac agaatcaggg gataacgcag gaaagaacat gtgagcaaaa   4200
ggccagcaaa aggccaggaa ccgtaaaaag gccgcgttgc tggcgttttt ccataggctc   4260
cgcccccctg acgagcatca caaaaatcga cgctcaagtc agaggtggcg aaacccgaca   4320
ggactataaa gataccaggc gtttccccct ggaagctccc tcgtgcgctc tcctgttccg   4380
accctgccgc ttaccggata cctgtccgcc tttctccctt cgggaagcgt ggcgctttct   4440
catagctcac gctgtaggta tctcagttcg gtgtaggtcg ttcgctccaa gctgggctgt   4500
gtgcacgaac ccccgttca gcccgaccgc tgcgccttat ccggtaacta tcgtcttgag   4560
tccaacccgg taagacacga cttatcgcca ctggcagcag ccactggtaa caggattagc   4620
agagcgaggt atgtaggcgg tgctacagag ttcttgaagt ggtggcctaa ctacggctac   4680
actagaagga cagtatttgg tatctgcgct ctgctgaagc cagttacctt cggaaaaaga   4740
gttggtagct cttgatccgg caaacaaacc accgctggta gcggtggttt ttttgtttgc   4800
aagcagcaga ttacgcgcag aaaaaaagga tctcaagaag atcctttgat cttttctacg   4860
gggtctgacg ctcagtggaa cgaaaactca cgttaaggga ttttggtcat gcatgatata   4920
tctcccaatt tgtgtagggc ttattatgca cgcttaaaaa taataaaagc agacttgacc   4980
tgatagtttg gctgtgagca attatgtgct tagtgcatct aacgcttgag ttaagccgcg   5040
ccgcgaagcg gcgtcggctt gaacgaattt ctagctagac attatttgcc gactaccttg   5100
gtgatctcgc cttttcacgta gtggacaaat tcttccaact gatctgcgcg cgaggccaag   5160
cgatcttctt cttgtccaag ataagcctgt ctagcttcaa gtatgacggg ctgatactgg   5220
gccggcaggc gctccattgc ccagtcggca gcgacatcct tcggcgcgat tttgccggtt   5280
actgcgctgt accaaatgcg ggacaacgta agcactacat ttcgctcatc gccagcccag   5340
tcgggcggcg agttccatag cgttaaggtt tcatttagcg cctcaaatag atcctgttca   5400
ggaaccggat caaagagttc ctccgccgct ggacctacca aggcaacgct atgttctctt   5460
gcttttgtca gcaagatagc cagatcaatg tcgatcgtgg ctggctcgaa gatacctgca   5520
agaatgtcat tgcgctgcca ttctccaaat tgcagttcgc gcttagctgg ataacgccac   5580
ggaatgatgt cgtcgtgcac aacaatggtg acttctacag cgcggagaat ctcgctctct   5640
ccaggggaag ccgaagtttc caaaaggtcg ttgatcaaag ctcgccgcgt tgtttcatca   5700
agccttacgg tcaccgtaac cagcaaatca atatcactgt gtggcttcag gccgccatcc   5760
actgcggagc cgtacaaatg tacggccagc aacgtcggtt cgagatggcg ctcgatgacg   5820
ccaactacct ctgatagttg agtcgatact tcggcgatca ccgcttcccc catgatgttt   5880
aactttgttt tagggcgact gccctgctgc gtaacatcgt tgctgctcca taacatcaaa   5940
```

```
catcgaccca cggcgtaacg cgcttgctgc ttggatgccc gaggcataga ctgtacccca    6000
aaaaaacagt cataacaagc catgaaaacc gccactgcgc cgttaccacc gctgcgttcg    6060
gtcaaggttc tggaccagtt gcgtgacggc agttacgcta cttgcattac agcttacgaa    6120
ccgaacgagg cttatgtcca ctgggttcgt gcccgaattg atcacaggca gcaacgctct    6180
gtcatcgtta caatcaacat gctaccctcc gcgagatcat ccgtgtttca aacccggcag    6240
cttagttgcc gttcttccga atagcatcgg taacatgagc aaagtctgcc gccttacaac    6300
ggctctcccg ctgacgccgt cccggactga tgggctgcct gtatcgagtg gtgattttgt    6360
gccgagctgc cggtcgggga gctgttggct ggctggtggc aggatatatt gtggtgtaaa    6420
caaattgacg cttagacaac ttaataacac attgcggacg tttttaatgt actgaattaa    6480
cgccgaattg ctctagcatt cgccattcag gctgcgcaac tgttgggaag gcgatcggt    6540
gcgggcctct tcgctattac gccagctggc gaaaggggga tgtgctgcaa ggcgattaag    6600
ttgggtaacg ccagggtttt cccagtcacg acgttgtaaa acgacggcca gtgccaagct    6660
aattcgcttc aagacgtgct caaatcacta tttccacacc cctatatttc tattgcactc    6720
cctttaact gttttttatt acaaaaatgc cctggaaaat gcactccctt tttgtgtttg    6780
ttttttttgtg aaacgatgtt gtcaggtaat ttatttgtca gtctactatg gtggcccatt    6840
atattaatag caactgtcgg tccaatagac gacgtcgatt ttctgcattt gtttaaccac    6900
gtggatttta tgacatttta tattagttaa tttgtaaaac ctacccaatt aaagacctca    6960
tatgttctaa agactaatac ttaatgataa caattttctt ttagtgaaga aagggataat    7020
tagtaaatat ggaacaaggg cagaagattt attaaagccg cggtaagaga caacaagtag    7080
gtacgtggag tgtcttaggt gacttaccca cataacataa agtgacatta acaaacatag    7140
ctaatgctcc tatttgaata gtgcatatca gcataccta ttacatatag ataggagcaa    7200
actctagcta gattgttgag cagatctcgg tgacgggcag gaccggacgg ggcggtaccg    7260
gcaggctgaa gtccagctgc cagaaaccca cgtcatgcca gttcccgtgc ttgaagccgg    7320
ccgcccgcag catgccgcgg ggggcatatc cgagcgcctc gtgcatgcgc acgctcgggt    7380
cgttgggcag cccgatgaca gcgaccacgc tcttgaagcc ctgtgcctcc agggacttca    7440
gcaggtgggt gtagagcgtg gagcccagtc ccgtccgctg gtggcggggg gagacgtaca    7500
cggtcgactc ggccgtccag tcgtaggcgt tgcgtgcctt ccaggggccc gcgtaggcga    7560
tgccggcgac ctcgccgtcc acctcggcga cgagccaggg atagcgctcc cgcagacgga    7620
cgaggtcgtc cgtccactcc tgcggttcct gcggctcggt acggaagttg accgtgcttg    7680
tctcgatgta gtggttgacg atggtgcaga ccgccggcat gtccgcctcg gtggcacggc    7740
ggatgtcggc cgggcgtcgt tctgggctca tggtagatcc cccgttcgta aatggtgaaa    7800
attttcagaa aattgctttt gctttaaaag aaatgattta aattgctgca atagaagtag    7860
aatgcttgat tgcttgagat tcgtttgttt tgtatatgtt gtgttgagaa ttaattctcg    7920
aggtcctctc caaatgaaat gaacttcctt atatagagga agggtcttgc gaaggatagt    7980
gggattgtgc gtcatccctt acgtcagtgg agatatcaca tcaatccact tgctttgaag    8040
acgtggtttgg aacgtcttct ttttccacga tgctcctcgt gggtgggggt ccatctttgg    8100
gaccactgtc ggtagaggca tcttgaacga tagcctttcc tttatcgcaa tgatggcatt    8160
tgtaggagcc accttccttt tccactatct tcacaataaa gtgacagata gctgggcaat    8220
ggaatccgag gaggtttccg gatattaccc tttgttgaaa agtctcaatt gccctttggt    8280
cttctgagac tgtatctttg atattttttgg agtagacaag tgtgtcgtgc tccaccatgt    8340
```

```
tatcacatca atccacttgc tttgaagacg tggttggaac gtcttctttt tccacgatgc    8400
tcctcgtggg tgggggtcca tctttgggac cactgtcggc agaggcatct tcaacgatgg    8460
cctttccttt atcgcaatga tggcatttgt aggagccacc ttccttttcc actatcttca    8520
caataaagtg acagatagct gggcaatgga atccgaggag gtttccggat attacccttt    8580
gttgaaaagt ctcaattgcc ctttggtctt ctgagactgt atctttgata ttttttggagt   8640 agacaagtgt gtcgtgctcc accatgttga cctgcaggtc gacacctggc acatcgtatc    8700
ttatctcttt tgtcgtttcc aacacaccac aacacaccta caaacgtgtc aattcacact    8760
tcaccaattt catttccttt tagtcaatca tattaaaagt agtagccccc acccccattt    8820
gttacctacc atttcccact ttaataatca cccacgctat gtccacttgt acttttgttt    8880
gcacacaact cttcccataa aatatcaaac caaattttttt ttagtggaaa acaaattccc    8940
caaatagaat actaacgaaa ttcatcgcat cagaatacac tcatctctga acagtggcga    9000
agcttgacgt tttcgacggg gggtcggaaa acgtatgtac ccgaaatttc tatagaatcg    9060
gggggtcgaa aacgtatata cccaaaattt ctatacgaaa actacatata taacactact    9120
gagcaaaaag ttcgggggtt cgggcgcccc tcccggcccc ttcaaagctt cgccaatgtc    9180
tctgaaccga agaaaaccct cactcgtcta ctagccaatg aatcctcacc agggaaaacc    9240
ctcactcgtc ttactggact attggcgctt ccaaatggac tacttgcgaa attcaccaca    9300
ttgggataca ctcgtctact gcggtgaggt aaaacccgct tggttcaagg atcgaactag    9360
cgattgctgc ctactcgcct aatctcccat catcaacagg tgccgccgaa acaaaatgct    9420
gggggcggga gttgaaccta ggtccagtga cgcacccatg aattttttttt ctagggatgc    9480 gaacgagtgg tttaaccata cttttaagag gtgcgatcgg aaattttacc tataaaatac    9540
actaaaaaag ttccaagggt ccacccaccc cttaacctaa gtccgccttt gtctggatca    9600
cgtgaaacat caggtctctc ccttaccagt ccagctacga ctcattgaca aaatatcaaa    9660
accatatgat tttgagtttt atctcaaccg aaagtgacat catgacagag aatcgacata    9720
accaaaacgt gtaaacgtac aactcaccat tgcgttgaaa aggacaaaac aggtaggatt    9780
cttgtcaaat tcaacgcgta cacctgtgct tcatctaaac cccatacttt taagaacctt    9840
tataaagacc actcactata tatacacata tataatatca cttatcaaac cctcggatcc    9900
accatgtctc ttcaacaagt aacaaccacc aggaagaacc gaaacgaggg gcggagacga    9960
tttaccgaca aacaaataag tttcctagag tacatgtttg agacacagtc gagacccgag   10020
ttaaggatga aacaccagtt ggcacataaa ctcgggcttc atcctcgtca agtggcgata   10080
tggttccaga acaaacgcgc gcgatcaaag tcgaggcaga ttgagcaaga gtataacgcg   10140
ctaaagcata actacgagac gcttgcgtct aaatccgagt tctaaagaa agagaatcag    10200 gccctactca atcaattgga ggtgctgaga aatgtagccg aaaagcatca agagaaaact   10260
agtagtagtg gcagcggtga agaatcggat gatcggttta cgaactctcc ggacgttatg   10320
tttggtcaag aaatgaatgt tccgttttgc gacggttttg cgtaccttga agaaggaaac   10380
agtttgttgg agattgaaga acaactgcca gaccttcaaa agtggtggga gttctaagag   10440
ctcgaatttc cccgatcgtt caaacatttg gcaataaagt ttcttaagat tgaatcctgt   10500
tgccggtctt gcgatgatta tcatataatt tctgttgaat tacgttaagc atgtaataat   10560
taacatgtaa tgcatgacgt tatttatgag atgggttttt atgattagag tcccgcaatt   10620
atacatttaa tacgcgatag aaaacaaaat atagcgcgca aactaggata aattatcgcg   10680
```

```
cgcggtgtca tctatgttac tagatcggga attcgtaatc atgtcatagc tgtttcctgt   10740
gtgaaattgt tatccgctca caattccaca caacatacga gccggaagca taaagtgtaa   10800
agcctggggt gcctaatgag tgagctaact cacattaatt gcgttgcgct cactgcccgc   10860
tttccagtcg ggaaacctgt cgtgccagct gcattaatga atcggccaac gcgcggggag   10920
aggcggtttg cgtattggag cttgagcttg gatcagattg tcgtttcccg ccttcagttt   10980
aaactatcag tgtttgacag gatatattgg cgggtaaacc taagagaaaa gagcgtttat   11040
tagaataatc ggatatttaa aagggcgtga aaaggtttat ccgttcgtcc atttgtatgt   11100
gcatgccaac cacagggttc ccctcgggat caa                                11133
```

Having especially described and determined the nature of the present invention and how to reduce it to practice, we claim the exclusive property right on:

1. A recombinant DNA molecule for improving the yield of a transformed soybean plant under abiotic stress conditions, comprising the sequence of SEQ ID NO: 1.

2. An expression vector functional in plants comprising the sequence of SEQ ID NO: 43.

3. A nonliving plant material comprising the recombinant DNA molecule according to claim 1.

* * * * *